(12) United States Patent
Allefs et al.

(10) Patent No.: US 7,485,773 B2
(45) Date of Patent: Feb. 3, 2009

(54) ISOLATED NUCLEIC ACIDS ENCODING RESISTANCE POLYPEPTIDES AND USES THEREOF

(75) Inventors: Josephus Jacobus H. M. Allefs, Emmeloord (NL); Edwin Andries G. van der Vossen, Utrecht (NL)

(73) Assignee: Kweek-en Researchbedrijf Agrico B.V. (NL)

( * ) Notice: Subject to any disclaimer, the term of this patent is extended or adjusted under 35 U.S.C. 154(b) by 989 days.

(21) Appl. No.: 10/360,522

(22) Filed: Feb. 7, 2003

(65) Prior Publication Data

US 2003/0221215 A1 Nov. 27, 2003

(30) Foreign Application Priority Data

Feb. 8, 2002 (EP) .................................. 02075565

(51) Int. Cl.
*C12N 15/29* (2006.01)
*C12N 15/82* (2006.01)
*A01H 5/00* (2006.01)
*A01H 5/10* (2006.01)

(52) U.S. Cl. ....................... 800/279; 800/278; 800/298; 800/295; 800/317.2; 800/317.4; 536/23.6; 435/320.1; 435/468; 435/419

(58) Field of Classification Search ................. 800/278, 800/279, 317, 298; 435/320.1, 468
See application file for complete search history.

(56) References Cited

U.S. PATENT DOCUMENTS 6,074,638 A * 6/2000 Anderson et al. ......... 424/93.43
6,100,449 A * 8/2000 Fluhr et al. ................. 800/279

OTHER PUBLICATIONS

Masuelli et al. Theor Appl Genet (1995) 91:401-408.*
van der Biezen, E.A. and J.D.G. Jones. "The NB-ARC domain: a novel signalling motif shared by plant resistance gene products and regulators of cell death in animals", *Current Biology*, 1998, 8(7): pp. R226-R227.
van der Biezen, E.A. and J.D.G. Jones. "Plant disease-resistance proteins and the gene-for-gene concept", *TIBS* 23, 1998, pp. 454-456.
Leister, D. et al. "A PCR-based approach for isolating pathogen resistance resistance genes from potato with potential for wide application in plants", *Nature Genetics*, 1996, 14: 421-429.
Ellis, J. et al. "Structure, function and evolution of plant disease resistance genes", *Biotic Interactions*, 2000, pp. 278-284.
Dong, F. et al. "Development and applications of a set of chromosome-specific cytogenetic DNA markers in potato", *Theor. Appl. Genet.*, 2000, 101: 1001-1007.
Pan, Q. et al. "Comparative Genetics of Nucleotide Binding Site-Leucine Rich Repeat Resistance Genes Homologues in the Genomes of Two Dicotyledons: Tomato and Arabidopsis", *Genetics*, 2000, 155:309-322.
Young, Nevin Dale. "The genetic architecture of resistance", *Biotic Interactions*, 2000, pp. 285-290.
Thieme, R. et al. "Production of somatic hybrids between *S. tuberosum* L. and late blight resistant Mexican wild potato species", *Euphytica*, 1997, 97: 189-200.
Oberhafemann, P. et al. "A genetic analysis of quantitative resistance to late blight in potato: towards marker-assisted selection", *Molecular Breeding*, 1999, 5: 399-415.
Pan, Q. et al. "Comparative genetics of nucleotide binding site-leucine rich repeat resistance gene homologs in the genomes of two dicotyledons: tomato and arabidopsis." *Genetics* 2000, 155(1): 309-322. Sequence listing; Submitted to the EMBL/GenBank/DDBJ databases, Aug. 2001, XP-2206417.
van der Hoeven, R. et al. "Generations of ESTs from dormant potato tubers." Unpublished. Sequence listing library, created Jun. 2001, The Institute for Genomic Research. XP-2206419.
Sasaki, T., et al. "Oryza sativa nipponbare (GA3) genomic DNA, chromosome 1, PAC clone: p0702B09." Sequence listing; Submitted to the EMBL/GenBank.DDBJ databases, Dec. 2000. XP-2206418.

* cited by examiner

*Primary Examiner*—Medina A Ibrahim
(74) *Attorney, Agent, or Firm*—Connolly Bove Lodge & Hutz LLP

(57) ABSTRACT

The invention provides isolated nucleic acids from potato encoding LRR polypeptides that confer late blight disease resistance in plants of the Solanaceae family and vectors and transgenic plants comprising the nucleic acids. The invention also provides a method for providing a plant or its progeny with resistance against an oomycete infection by transforming the nucleic acids or the vectors.

32 Claims, 35 Drawing Sheets

Figure 6A

```
   1  ATGGCTGAAGCTTTCATTCAAGTTCTGCTAGACAATCTCACTTCTTTCCT
  51  CAAAGGGGAACTTGTATTGCTTTTCGGTTTTCAAGATGAGTTCCAAAGGC
 101  TTTCAAGCATGTTTTCTACAATTCAACCCCTCCTTCAAGATGCTCAGGAG
 151  AAGCAACTCAACAACAAGCCTCTAGAAAATTGGTTGCAAAAACTCAATGC
 201  TGCTACATATGAAGTCGATGACATCTTGGATGAATATAAAACCAAGGCCA
 251  CAAGATTCTCCCAGTCTGAATATGGCCGTTATCATCCAAAGCTTATCCCT
 301  TTCCGTCACAAGGTCGGGAAAAGGATGCACCAAGTGATGAAAAACTAAA
 351  GGCAATTGCTGAGGAAAGAAAGAATTTTCATTTGCACGAAAAAATTGTAG
 401  AGAGACAAGCTGTTACACCCCAAACACCTCTGTATTAACCGAACCGCAG
 451  GTTTATGGAAGAGACAAAGAGAAAGATGAGATAGTGAAAATCCTAATAAA
 501  CAATGTTAGTGATGCCCAACACCTTTCAGTCCTCCCAATACTTGGTATGG
 551  CCCCATTACCAAAAACGACTCTTGCCCAAATGGTCTTCAATGACCAGAGA
 601  GTTACTGAGCATTTCCATTCCAAAATATGGATTTGTGTCTCGGAAGATTT
 651  TGATGAGAAGAGGTTAATAAAGGCAATTGTAGAATCTATTGAAGGAAGGC
 701  CACTACTTGGTCAGATGCACTTGGCTCCACTTCAAAAGAAGCTTCAGGAG
 751  TTGCTGAATGGAAAAGATACTTGCTTGTCTTAGATGATGTTTGGAATGA
 801  AGATCAACAGAAGTGGGCTAATTTAAGAGCAGTCTTCAAGGTTGGAGCAA
 851  CTCCTCCTTCTGTTCTAACCACTACTCGTCTTGAAAAGGTTGGATCAATT
 901  ATGGGAACATTGCAACCATATGAACTGTCAAATCTGTCTCAAGAACATTC
 951  TTGGTTGTTGTTCATGCAACGTGCATTTGGACACCAAGAAGAAATAAATC
1001  CAAACCTTGTGGCAATCGCAAACCAGATTGTGAAAAAAGTGGTGGTGTG
```

Figure 6A (Continued)

```
1101  AAGAGCATGGGAACATGTGAGAGACAGTCCGATTTGGAATTTGCCTCAAG
1151  ATGAAAGTTCTATTCTCCCTCCCTGAGGCTTAGTTACCATCAACTTCCA
1201  CTTGATTTGAAACAATGCTTTGCGTATTGTGCGGTGTTCCCAAAGGATGC
1251  CAAAATGGAAAAGAAAGCTAATCTCTCTCTGGATGGCGCATGGTTTC
1301  TTTTATCAAAGGAAACATGGAGCTAGAGGATGTGGGCGATGAAGTATGG
1351  AAAGAATTATACTTGAGGTCTTTTTCCAAGAGATTGAAGTTAAAGATGG
1401  TAAAACTTATTTCAAGATGCATGATCTCATCCATGATTTGGCAACATCTC
1451  TGTTTTCAGCAAACACATCAAGCAGCAATATCCGTGAAATAAATAAACAC
1501  AGTTACACATATGATGTCCATTGGTTTCGCCGAAGTGGTGTTTTTTTA
1551  CACTCTTCCCCCCTTGGAAAAGTTTATCTCGTTAAGAGTGCTTAATCTAG
1601  GTGATTCGACATTTAATAAGTTACCATCTTCCATTGGAGATCTAGTACAT
1651  TTAAGATACTTGAACCTGTATGGCAGTCCATCCCTACTCTTCCAAAGCA
1701  GTTATGCAAGCTTCAAAATCTGCAAACTCTTGATCTACAATATTGCACCA
1751  AGCTTTGTTGTTTGCCAAAAGAAACAAGTAAACTTGGTAGTCTCCGAAAT
1801  CTTTTACTTGATGGTAGCCAGTCATTCACTTCTATCCACCAAGGATAGG
1851  ATCATTGACATGCCTTAAGACTCTAGGTCAATTTGTTGTTGGAAGGAAGA
1901  AAGGTTATCAACTTGGTGAACTAGGAAACCTAAATCTCTATGGCTCAATT
1951  AAAATCTCGCATCTTGAGAGAGTGAACAATCATAACCACGCAAAAGAAGC
2001  CAATTTATCTGCAAAAGGGAATCTGCATTCTTTAAGCATGAGTTGGAATA
2051  ACTTTGGACCACATATATGAATCAGAAGAAGTTAAAGTGCTTGAAGCC
2101  CTCAAACCACACTCCAATCTGACTTCTTTAAAAATCTATGGCTTCAGAGG
2151  AATCCATCTCCCAGAGTGGATGAATCACTCAGTATTGAAAAATATTGTCT
2201  CTATTCTAATTAGCAACTTCAGAAACTGCTCATGCTTACCACCCTTTGGT
```

Figure 6A (Continued)

```
2251    GATCTGCCTTGTCTAGAAAGTCTAGAGTTACACTGGGGGTCTGCGGATGT
2301    GGAGTATGTTGAAGAAGTGGATATTGATGTTCATTCTGGATTCCCCACAA
2351    GAATAAGGTTTCCATCCTTGAGGAAACTTGATATATCGCACTTTGGTAGT
2401    CTGAAAGGATTGCTGAAAAAGGAAGGAGAAGAGCAATTCCCTGTGCTTGA
2451    AGAGATGATAATTCACGAGTGCCCTTTTCTGACCCTTTCTTCTAATCTTA
2501    GGGCTCTTACTTCCCTCAGAATTTGCTATAATAAACTACCTACTTCATTC
2551    CCAGAAGAGATGTTCAAAAACCTTGCAAATCTCAAATACTTGACAATCTC
2601    TCGGTGCAATAATCTCAAAGAGCTGCCTACCAGCTTGGCTAGTCTGAATG
2651    CTTTGAAAACTCTAAAAATTCAATTGTGTTGCGCACTAGAGAGTCTCCCT
2701    GAGGAAGGGCTGGAAGGTTTATCTTCACTCACAGAGTTATTTGTTGAACA
2751    CTGTAACATGCTAAAATGTTTACCAGAGGGATTGCAGCACCTAACAACCC
2801    TCACAAGTTTAAAAATTCGGGATGTCCACAACTCATCAACCGGTGTGAG
2851    AAGGGAATAGGAGAAGACTGGCACAAAATTTCTCACATTCCTAATGTGAA
2901    TATATATATTTAA
```

Figure 6B

```
   1  ATGCCTGAACCTTTCATTCAAGTTCTGCTAGACAATCTCACTTCTTTCCT
  51  CAAAGGGGAACTTGTATTGCTTTTCGTTTTCAACATCACTTCCAAAGGC
 101  TTTCAAGCATGTTTTCTACAATTCAAGCCGTCCTTGAAGATGCTCAGGAG
 151  AAGCAACTCAACAACAAGCCTCTAGAAAATTGGTTGCAAAAACTCAATGC
 201  TCCTACATATGAAGTCGATGACATCTTGGATGAATATAAAACCAAGGCCA
 251  CAAGATTCTCCCAGTCTGAATATGGCCGTTATCATCCAAACGTTATCCCT
 301  TTCCGTCACAAGGTCGGGAAAAGGATGGACCAAGTGATGAAAAACTAAA
 351  GGCAATTGCTGAGGAAAGAAAGAATTTTCATTTGCACGAAAAAATTGTAG
 401  ACACACAAGCTGTTACACGGGAAACAGGTACTCATCTTAAATTAGTATTA
 451  CAACAACTAAGTTTATATTCATTTTTTTGGCAATTATCAAATTCAGAAAA
 501  GGGTTAAATATACTCATGTCCTATCGTAAATAGTGTATATATACCTCTCG
 551  TTGTACTTTCGATCTGAATATACTTGTCAAATCTGGCAAGCTCAGAATCA
 601  AATTATCCACCCCAACTTTTAAATACTCGATATCTTTAGAAATCCACCTG
 651  TCTAACTCATCCACTACCCATTCCCTTTGCTTTCAATTCTTTTCTTTACC
 701  TATAAACTTGGAACACTCGATCCGTTTTGCTTTTCTTAACAAAGCAGCTC
 751  AGAGAAAAGAGGTTTTCTTCTATTCTGTTTCTCTGTGTGCTGCACTTGGG
 801  TCCTTAATCCCATTAAAAACAGGGCATGTTAATCCCAACGACGGTAGCCT
 851  TTCCTGACAGCTGACTGTAAATTTTGTCTAACAAAGAAAAAAAAGATTA
 901  GACATGTTTTCCTTGTCATTGATTAGGCTGGATTTCTTTCAGAGTGGAA
 951  CATAGGGGATATATTGGACCAAAAGTAGAATGGGTATATATTTAAAGTAT
1001  TTCTGATAGAACAGGAGTATATTGTGCGAAAATATCCTCTATTTTCTGTT
1051  GTCTCCTAATGAGTTTGAATGTAATAATATTCTCATGTGGACATTGCTTG
1101  CACCAGGTTCTGTATTAACCGAACCGCAGGTTTATGGAAGAGACAAAGAG
1151  AAAGATGAGATAGTGAAAATCCTAATAAACAATGTTAGTGATGCCCAACA
1201  CCTTTCAGTCCTCCCAATACTTGGTATGGGGGGATTAGGAAAAACGACTC
1251  TTGCCCAAATGCTCTTCAATGACCAGAGAGTTACTGAGCATTTCCATTCC
1301  AAAATATGGATTTGTGTCTCGGAAGATTTTGATGAAGAGGTTAATAAA
1351  GGCAATTGTAGAATCTATTGAAGGAAGGCCACTACTTGGTGAGATGGACT
1401  TGCCTCCACTTCAAAAGAAGCTTCAGGAGTTGCTGAATGGAAAAAGATAC
```

Figure 6B (Continued)

```
1451    TTGCTTGTCTTAGATGATGTTTGGAATGAAGATCAACAGAAGTGGGCTAA
1501    TTTAAGAGCAGTCTTGAAGGTTGGAGCAAGTGGTGCTTCTGTTCTAACCA
1551    CTACTCGTCTTGAAAAGGTTGGATCAATTATGGGAACATTGCAACCATAT
1601    GAACTGTCAAATCTGTCTCAAGAACATTGTTGGTTGTTCTTCATGCAACG
1651    TGCATTTGGACACCAAGAAGAAATAAATCCAAACCTTGTGGCAATCGGAA
1701    AGGAGATTGTGAAAAAAGTGGTGGTGTGCCTCTAGCAGCCAAAACTCTT
1751    GGAGGTATTTTGTGCTTCAAGAGAGAAGAAAGAGCATGGGAACATGTGAG
1801    AGACAGTCCGATTTGGAATTTGCCTCAAGATGAAACTTCTATTCTGCCTG
1851    CCCTGAGGCTTAGTTACCATCAACTTCCACTTGATTTGAAACAATGCTTT
1901    GCGTATTGTGCGGTGTTCCCAAAGGATGCCAAAATGGAAAAAGAAAAGCT
1951    AATCTCTCTCTGCATGGCGCATGGTTTTCTTTTATCAAAAGGAAACATGG
2001    AGCTAGAGGATGTGGGCGATGAACTATCGAAACAATTATACTTGAGGTCT
2051    TTTTTCCAAGAGATTGAAGTTAAAGATGGTAAAACTTATTTCAAGATGCA
2101    TGATCTCATCCATGATTTGGCAACATCTCTGTTTTCAGCAAACACATCAA
2151    GCAGCAATATCCGTGAAATAAATAAACACAGTTACACACATATGATGTCC
2201    ATTGGTTTCGCCGAAGTGGTGTTTTTTTACACTCTTCCCCCCTTGGAAAA
2251    GTTTATCTCGTTAAGAGTGCTTAATCTAGGTGATTCGACATTTAATAAGT
2301    TACCATCTTCCATTGGAGATCTAGTACATTTAAGATACTTGAACCTGTAT
2351    GGCAGTGGCATGCGTAGTCTTCCAAAGCAGTTATGCAAGCTTCAAAAATCT
2401    GCAAACTCTTCATCTACAATATTCCACCAAGCTTTGTTGTTTGCCAAAAG
2451    AAACAAGTAAACTTGGTAGTCTCCGAAATCTTTTACTTGATGGTACCCAC
2501    TCATTGACTTGTATGCCACCAAGGATAGGATCATTGACATGCCTTAAGAC
2551    TCTAGGTCAATTTGTTGTTGGAAGGAAGAAAGGTTATCAACTTGGTGAAC
2601    TAGGAAACCTAAATCTCTATCCCTCAATTAAAATCTCGCATCTTGAGAGA
2651    GTGAAGAATGATAAGGACGCAAAAGAAGCCAATTTATCTGCAAAAGGGAA
2701    TCTGCATTCTTTAAGCATGAGTTGGAATAACTTTGGACCACATATATATG
2751    AATCAGAAGAAGTTAAAGTGCTTGAAGCCCTCAAACCACACTCCAATCTG
2801    ACTTCTTTAAAAATCTATCGCTTCACACCAATCCATCTCCCAGAGTGGAT
2851    GAATCACTCAGTATTGAAAAATATTGTCTCTATTCTAATTAGCAACTTCA
2901    GAAACTGCTCATGCTTACCACCCTTTGGTGATCTGCCTTGTCTAGAAAGT
2951    CTAGAGTTACACTGGGGGTCTGCGGATGTGGAGTATGTTGAAGAAGTGGA
3001    TATTGATGTTCATTCTGGATTCCCCACAAGAATAAGGTTTCCATCCTTCA
```

Figure 6B (Continued)

```
3051  GGAAACTTGATATATGGGACTTTCGTAGTCTGAAAGGATTGCTGAAAAAG
3101  GAAGGAGAAGAGCAATTCCCTGTGCTTGAAGAGATGATAATTCACCAGTG
3151  CCCTTTTCTGACCCTTTCTTCTAATCTTAGGGCTCTTACTTCCCTCAGAA
3201  TTTGCTATAATAAAGTAGCTACTTCATTCCCAGAAGAGATGTTCAAAAAC
3251  CTTGCAAATCTCAAATACTTGACAATCTCTCGGTGCAATAATCTCAAAGA
3301  GCTGCCTACCAGCTTGGCTAGTCTGAATGCTTTGAAAAGTCTAAAAATTC
3351  AATTGTGTTGCGCACTAGAGAGTCTCCCTGAGGAAGGGCTGGAAGGTTTA
3401  TCTTCACTCACAGAGTTATTTGTTGAACACTGTAACATGCTAAAATGTTT
3451  ACCAGAGGGATTGCAGCACCTAACAACCCTCACAAGTTTAAAAATTCGGG
3501  GATGTCCACAACTGATCAAGCGGTGTGAGAAGGGAATAGGAGAACACTCC
3551  CACAAATTTCTCACATTCCTAATGTGAATATATATATTTAA
```

Figure 6C

```
   1   AGTACTCCATCCGTTCACTTTGATTTGTCATGTTGCACTTTTCGAAAGTC
  51   AATTTGACTAATTTTTAAAGCTAAATTAGATTACACTAATTCAATATTTT
 101   AAACAGAAAAATTAGATATTCAAAAACTATACAAAAAATATTATACATTG
 151   CAATTTTTTGCATATCAATATGATAAAAAATATATCGTAAAATATTAGT
 201   CAAAATTTTTATAATTTGACTCAAATCATGAAAAGTATAATAATTAATAG
 251   TGGACGGAGGAAGTATTGTCTTTCCACATTTCTCCCCATTTTTGGTCCAA
 301   GGGCCATTAGCAGTTCTCTTCATTTCTACTTCTGTCTCATATTAGATGG
 351   GCATCTTACTAAAATATTTGTCTCATATTACTTGATTATTTATTAAATC
 401   AAAAAGAATTAATTAATTTTTTCTCATTTTACCCCTACAATTAATATAGT
 451   TTTAAAAGTTTTAAACAAATTTTGAACAATCAAAATTTCTTTTGCAAGAG
 501   ACTTATTAATATAAACAAAGGATAAAATAATAAAAGCTGTCAATTTATTG
 551   ACCATCACTTAATAATATATAAAATACAAACTGCTGATCTAATATGAGAC
 601   GGACAAAATATATTCTAAAATATTTTCGGACAGATATGTGATATTCTAAC
 651   CATTCACTACACTATATTATGCATTTTATCCGCCAATGACTTATTTCAGC
 701   TTTAATTAATTAGGAAAGAGGAAACTGCCAATGAGGAAGAGTAGGGGCGT
 751   AGTTGCTGTCGACGAAAAAAGATAATACTCACTCTTTTCGATTTTTATT
 801   TTTATTTATCACTTTTAACCTATCATGTAAAAAGATAATTATTTTTTTCA
 851   TGCTTTATCCTTAGTATTAAACAATTTAATACCCATTATTTTGTAAAATA
 901   TTTATATGAATAATTGTTTTCGTAATGAATTTGTCCGGTCAAACAATGAT
 951   AAATAAAATGAATGAAGAGAGTAGAAAAACAAAACAAAAGAACAAGTTGA
1001   CAACTTGAGAGATTAAAAGGGTCCAAAACGCCTTGGATTTTGAGATTCCA
1051   TATGTGAAATTTCCATCAAATAATTCAATTTGTACTATTACAAGTCAAAC
1101   TTTCCATTTCATTCCAACTAGCCATCTTGGCTTCAAAATTACACATTCAT
1151   TCATTCACAGATCTAATATTCTTAATAGTGACTTCCACATATGGCTGAAG
1201   CTTTCATTCAAGTTCTGCTAGACAATCTCACTTCTTTCCTCAAAGGGGAA
1251   CTTGTATTCCTTTTCCGTTTTCAAGATGAGTTCCAAAGGCTTTCAAGCAT
1301   GTTTTCTACAATTCAAGCCGTCCTTGAAGATGCTCAGGAGAAGCAACTCA
1351   ACAACAAGCCTCTAGAAAATTGGTTGCAAAAACTCAATGCTGCTACATAT
1401   CAAGTCGATGACATCTTGGATGAATATAAAACCAAGGCCACAAGATTCTC
```

Figure 6C (Continued)

```
1451  CCAGTCTGAATATGGCCGTTATCATCCAAAGGTTATCCCTTTCCGTCACA
1501  ACGTCGGGAAAAGGATGGACCAAGTGATGAAAAAACTAAAGGCAATTGCT
1551  GAGGAAAGAAAGAACTTTCATTTGCACGAAAAAATTGTAGAGAGACAAGC
1601  TGTTAGACGGGAAACAGGTACTCATCTCAAATTAGTATTACAACAACTAA
1651  GTTTATATTCATTTTTTTGGCAATTATCAAATTCAGAAAAGGGTTAAATA
1701  TACTCATGTCCTATCGTAAATAGTGTATATATACCTCTCGTTGTACTTTC
1751  GATCTGAATATACTTGTCAAATCTGGCAAGCTCAGAATCAAATTATCCAC
1801  CCCAACTTTTAAATACTCGATATCTTTAGAAATCCACCTGTCTAACTCAT
1851  CCACTACCCATTCCCTTTGCTTTGAATTCTTTTCTTTACCTATAAACTTG
1901  GAACACTCGATCCGTTTTGCTTTTCTTAACAAAGCAGCTCAGAGAAAAGA
1951  GGTTTTCTTCTATTCTGTTTCTCTCTCCTCCACTTGGGTCCTTAATCC
2001  CATTAAAAACAGGGCATGTTAATCCCAACGACGGTAGCCTTTCCTGACAG
2051  CTGACTGTAAATTTTGTCTAACAAAGAAAAAAAAGATTAGACATGTTTT
2101  TCCTTGTCATTGATTAGGCTGGATTTCTTTCAGAGTGGAACATAGGGGAT
2151  ATATTGGACCAAAACTACAATCCCTATATATTTAAAGTATTTCTGATAGA
2201  ACAGGAGTATATTGTGCGAAAATATCCTCTATTTTCTGTTGTCTCCTAAT
2251  GAGTTTGAATGTAATAATATTCTCATGTGGACATTGCTTGCACCAGGTTC
2301  TGTATTAACCGAACCGCAGGTTTATGGAAGAGACAAAGAGAAAGATGAGA
2351  TACTCAAAATCCTAATAAACAATGTTAGTGATGCCCAACACCTTTCAGTC
2401  CTCCCAAAACTTGGTATCGGGGCATTACCAAAAACGACTCTTGCCCAAAT
2451  GGTCTTCAATGACCAGAGAGTTACTGAGCATTTCCATTCCAAAATATGGA
2501  TTTGTGTCTCGGAAGATTTTGATGAGAAGAGGTTAATAAAGGCAATTGTA
2551  GAATCTATTGAAGGAAGGCCACTACTTCCTCAGACCGACTTGGCTCCACT
2601  TCAAAAGAAGCTTCAGGAGTTGCTGAATGGAAAAAGATACTTGCTTGTCT
2651  TAGATGATGTTTGGAATGAAGATCAACAGAAGTGGGCTAATTTAAGAGCA
2701  GTCTTGAAGGTTGGAGCAAGTGGTGCTTCTGTTCTAACCACTACTCGTCT
2751  TGAAAAGGTTGGATCAATTATCCGAACATTGCAACCATATGAACTGTCAA
2801  ATCTGTCTCAAGAAGATTGTTGGTTGTTGTTCATGCAACGTGCATTGGA
2851  CACCAAGAAGAAATAAATCCAAACCTTGTGGCAATCGGAAGGAGATTGT
2901  GAAAAAAGTGGTGGTGTGCCTCTAGCAGCCAAAACTCTTGGAGGTATTT
2951  TCTGCTTCAACACAGAAGAAAGAGCATCCCAACATGTCACAGACAGTCCG
3001  ATTTGGAATTTGCCTCAAGATGAAAGTTCTATTCTGCCTGCCCTGAGGCT
```

Figure 6C (Continued)

```
3051  TAGTTACCATCAACTTCCACTTGATTTGAAACAATGCTTTGCGTATTGTG
3101  CGGTGTTCCCAAAGGATGCCAAAATGGAAAAAGAAAAGCTAATCTCTCTC
3151  TGGATGGCGCATGCTTTTCTTTTATCAAAAGGAAACATGGAGCTAGAGGA
3201  TGTGGGCGATGAAGTATGGAAAGAATTATACTTGAGGTCTTTTTTCCAAG
3251  AGATTGAAGTTAAAGATGGTAAAACTTATTTCAAGATGCATGATCTCATC
3301  CATGATTTGGCAACATCTCTGTTTTCAGCAAACACATCAAGCAGCAATAT
3351  CCGTGAAATAAATAAACACAGTTACACACATATGATGTCCATTGGTTTCG
3401  CCGAAGTGGTGTTTTTTTACACTCTTCCCCCCTTGGAAAAGTTTATCTCC
3451  TTAAGAGTGCTTAATCTAGGTGATTCGACATTTAATAAGTTACCATCTTC
3501  CATTGGAGATCTAGTACATTTAAGATACTTGAACCTGTATGGCAGTGGCA
3551  TGCGTAGTCTTCCAAACCACTTATGCAAGCTTCAAAATCTGCAAACTCTT
3601  GATCTACAATATTGCACCAAGCTTTGTTGTTTGCCAAAAGAAACAACTAA
3651  ACTTGGTACTCTCCGAAATCTTTTACTTGATGGTAGCCAGTCATTGACTT
3701  GTATGCCACCAAGGATAGGATCATTGACATGCCTTAAGACTCTAGGTCAA
3751  TTTGTTCTTCCAACCAACAAAGGTTATCAACTTGGTGAACTAGGAAAGCT
3801  AAATCTCTATGGCTCAATTAAAATCTCGCATCTTGAGAGAGTGAAGAATG
3851  ATAAGGACGCAAAAGAAGCCAATTTATCTGCAAAAGGGAATCTGCATTCT
3901  TTAAGCATGAGTTGGAATAACTTTGGACCACATATATATGAATCAGAAGA
3951  ACTTAAAGTGCTTGAAGCCCTCAAACCACACTCCAATCTGACTTCTTTAA
4001  AAATCTATGGCTTCAGAGGAATCCATCTCCCAGAGTGGATGAATCACTCA
4051  GTATTGAAAAATATTGTCTCTATTCTAATTAGCAACTTCAGAAACTGCTC
4101  ATGCTTACCACCCTTTGGTGATCTGCCTTGTCTAGAAAGTCTAGAGTTAC
4151  ACTGGGGGTCTCCGCATCTGCACTATCTTGAAGAAGTGGATATTGATGTT
4201  CATTCTGGATTCCCCACAAGAATAAGGTTTCCATCCTTGAGGAAACTTCA
4251  TATATGGACTTTGGTAGTCTGAAAGGATTGCTGAAAAAGGAAGGAGAAG
4301  AGCAATTCCCTGTGCTTGAAGAGATGATAATTCACGAGTGCCCTTTTCTG
4351  ACCCTTTCTTCTAATCTTAGGGCTCTTACTTCCCTCAGAATTTGCTATAA
4401  TAAAGTAGCTACTTCATTCCCAGAAGAGATGTTCAAAAACCTTGCAAATC
4451  TCAAATACTTGACAATCTCTCGGTGCAATAATCTCAAAGAGCTGCCTACC
4501  AGCTTGGCTAGTCTGAATGCTTTGAAAAGTCTAAAAATTCAATTGTGTTG
4551  CGCACTAGAGAGTCTCCCTCACCAACGGCTGGAAGGTTTATCTTCACTCA
4601  CAGAGTTATTTGTTGAACACTGTAACATGCTAAAATGTTTACCAGAGGGA
```

Figure 6C (Continued)

```
4651  TTGCAGCACCTAACAACCCTCACAAGTTTAAAAATTCGGGCATGTCCACA
4701  ACTGATCAAGCGGTGTGAGAAGGGAATAGGAGAAGACTGGCACAAAATTT
4751  CTCACATTCCTAATGTGAATATATATATTAAGTTATTTGCTATTGTTTC
4801  TTTGTTTGTGAGTCTTTTTGGTTCCTGCCATTGTGATTGCATGTAATTTT
4851  TTTCTAGGGTTGTTTCTTTATGAGTCTCTCTCCATTGGATGTAATTTTC
4901  TTTTGGAAACAAATCTGTCAATTGATTTGTATTATACGCTTTCAGAATCT
4951  ATTACTTATTTGTAATTGTTTCTTTGTTTGTAAATTGTGAGTATCTTATT
5001  TTATGGAATTTTCTGATTTTATTTTGAAAACAAATCAATGATTTCTAACA
5051  TCCATCTGTATTATACTCCCTTCGTCTCATTTTATGTGTCACCTGTCGGA
5101  TTTCGAGATTCAAACAAATCTATCTTTGATCGTAAATTTTTAATAGATCT
5151  TTTAAACATTTTGAATTATCAATTATTGTGACTTTAGTACT
```

Figure 6D

```
   1  ATGGCTGAAGCTTTCCTTCAAGTTCTGCTAGATAATCTCACTTTTTTCAT
  51  CCAAGGGGAACTTGGATTGGTTTTTGGTTTCGAGAAGGAGTTTAAAAAAC
 101  TTTCAAGTATGTTTTCAATGATCCAAGCTGTGCTAGAAGATGCTCAAGAG
 151  AACCAACTCAACTACAAGGCAATAAAGAACTGGTTACAGAAACTCAATGT
 201  TGCTGCATATGAAGTTGATGACATCTTCCATCACTGTAAAACTGAGGCAG
 251  CAAGATTCAAGCAGGCTGTATTGGGGCGTTATCATCCACGGACCATCACT
 301  TTCTGTTACAAGGTGGGAAAAGAATGAAAGAAATGATGGAAAAACTAGA
 351  TGCAATTGCAGAGGAACGGAGGAATTTTCATTTAGATGAAAGGATTATAG
 401  AGAGACAAGCTGCTAGACGGCAAACAGGTGCTCATCTTAATTTTATTTTA
 451  AAACAAATAAGTATTACAAATTGCAGAGAAACGAAGGAATTTATATTCAT
 501  TTTTATTTTTGGCAATTATCAAAGTCATTTGTGTTTTAAGCTGGGGGA
 551  AGTTTCAAATATTTTCTCTAGTCTTAATGTTTGTCTCACTCACTCAGCAT
 601  GATTTTCTCAATCCTTCACTTCAACTCCCCCCTACTGTGCAAATATCTTC
 651  TCTATTTCTGTTGACTCCTAATGAGCTTGAATGTAACAACATTCTTGTT
 701  TGGAGCAGCTTTGTTTTAACTGAGCCAAAAGTTTATGGAAGGGAAAAAG
 751  AGGAGGATGAGATAGTGAAAATCTTGATAAACAATGTTAGTTATTCCGAA
 801  GAAGTTCCAGTACTCCCAATACTTGGTATGGGGGACTAGCAAAGACGAC
 851  TCTAGCCCAAATGGTCTTCAATGATCAAAGAATTACTGAGCATTTCAATC
 901  TAAAGATATGGGTTTGTGTCTCAGATGATTTTGATGAGAAGAGGTTGATT
 951  AAGGCAATTGTAGAATCTATTGAAGGAAAGTCACTGGGTGACATGGACTT
1001  GGCTCCCCTCCAGAAAAGCTTCAGGAGTTCTTGAATGGAAAAGATACT
1051  TTCTTGTTTTGGATGATGTTTGGAATGAAGATCAAGAAAGTCGGATAAT
1101  CTTAGAGCAGTATTGAAGATTGGAGCTAGTGGTGCTTCAATTCTAATTAC
1151  TACTCGTCTTGAAAAAATTGGATCAATTATGGGAACTTTGCAACTATATC
1201  AGTTATCAAATTTGTCTCAAGAAGATTGTTGGTTGTTGTTCAAGCAACGT
1251  GCATTTTGCCACCAAACCGAAACAAGTCCTAAACTTATGGAAATCGGAAA
1301  GGAGATTGTGAAGAAATGTGGGGGTGTGCCTCTAGCAGCCAAAACTCTTG
1351  GAGGCCTTTTACTCTTCAAGAGGGAAGAAAGTGAATGGGAACATGTGACA
1401  GATAGTGAGATTTGGAATTTACCTCAAGATGAAAATTCTGTTTTGCCTGC
```

Figure 6D (Continued)

```
1451  CCTGAGGCTGAGTTATCATCATCTTCCACTTGATTTCAGACAATGTTTTG
1501  CATATTGCGCAGTATTCCCAAAGGACACCAAAATAGAAAAGGAATATCTC
1551  ATCGCTCTCTGGATGGCACACAGTTTTCTTTTATCAAAAGGAAACATGGA
1601  GCTAGAGGATGTGGGCAATGAAGTATGGAATGAATTATACTTGAGGTCTT
1651  TTTTCCAAGACATTGAACTTAAATCTGGTAAAACTTATTTCAAGATGCAT
1701  GATCTCATCCATGATTTGGCTACATCTATCTTTTCAGCAAGCGCATCAAG
1751  CAGAAGTATACGCAAATAAATGTAAAAGATGATGAAGATATGATGTTCA
1801  TTGTAACAAATTATAAAGATATGATGTCCATTGGTTTCTCCGAAGTGGTG
1851  TCTTCTTACTCTCCTTCGCTCTTTAAAAGGTTTGTCTCGTTAAGGGTGCT
1901  TAATCTAAGTAACTCAGAATTTGAACAGTTACCGTCTTCCGTTGGAGATC
1951  TAGTACATTTAAGATACCTTGACCTGTCTGGTAATAAAATTTGTAGTCTT
2001  CCAAAGAGGTTGTGCAAGCTTCAAAATCTCCACACTCTTGATCTATATAA
2051  TTGCCAGTCACTTTCTTGTTTGCCGAAACAAACAAGTAAGCTTTGTAGTC
2101  TCCGGAATCTTGTACTTGATCACTGTCCATTGACTTCTATGCCACCAAGA
2151  ATAGGATTGTTGACATGCCTTAAGACACTAGGTTACTTTGTTGTAGGCGA
2201  GAGCAAACCTTATCAACTTGGTGAACTACGAAATTTAAACCTCCGTGGTG
2251  CAATTTCAATCACACATCTTGAGAGACTCAAAAATGATATGGAGGCAAAA
2301  GAAGCCAATTTATCTGCAAAAGCAAATCTACACTCTTTAAGCATCACTTG
2351  GGATAGACCAAACAGATATGAATCGAAGAAGTTAAAGTGCTTGAAGCCC
2401  TCAAACCACATCCCAATCTGAAATATTTAGAAATCATTGACTTCTGTGGA
2451  TTCTCTCTCCCTGACTGGATGAATCACTCAGTTTTGAAAAATGTTGTCTC
2501  TATTCTAATTAGCGGTTCTCAAAACTGCTCGTGCTTACCACCCTTTGGTG
2551  AGCTGCCTTGTCTAGAAAGTCTGGAGTTACAAGACGGGTCTGTCCAGGTG
2601  GAGTATGTTGAAGATTCTGGATTCCTGACAAGAAGAAGATTTCCATCCCT
2651  GAGAAACTTCATATAGGTGGCTTTTGTAATCTGAAAGGATTGCAGAGAA
2701  TGAAAGGAGCAGAGCAATTCCCCGTGCTTGAAGAGATGAAGATTTCGGAT
2751  TCCCTATGTTTGTTTTTCCGACCCTTTCTTCTGTCAAGAAATTAGAAAT
2801  TTGGGGGGAGGCAGATGCAGGAGGTTTCACCTCCATATCTAATCTCAGCA
2851  CTCTTACATCCTCAAGATTTTCAGTAACCACACAGTGACTTCACTACTG
2901  GAAGAGATGTTCAAAAACCTTGAAAATCTCATATACTTGAGTGTCTCTTT
2951  CTTGGAGAATCTCAAAGAGCTGCCTACCAGCCTGGCTAGTCTCAACAATT
3001  TGAAGTGTCTGGATATTCGTTATTGTTACGCACTAGAGAGTCTCCCCGAG
```

Figure 6D (Continued)

```
3051  GAAGGGCTGGAAGGTTTATCTTCACTCACAGAGTTATTTGTTGAACACTG
3101  TAACATGCTAAAATGTTTACCAGAGGGATTGCAGCACCTAACAACCCTCA
3151  CAAGTTTAAAAATTCGGGGATGTCCACAACTGATCAAGCGGTGTGAGAAG
3201  CCAATACCACAAGACTGCACAAAATTTCTCACATTCCTAATGTGAATAT
3251  ATATATTTAA
```

Figure 6E

| | |
|---|---|
| 1 | ATGGCTGAAGCTTTCATTCAAGTTGTGCTAGACAATCTCACTTCTTTCCT |
| 51 | CAAAGGGGAACTTGTATTGCTTTTCGGTTTTCAAGATGAGTTCCAAACCC |
| 101 | TTTCAAGCATGTTTTCTACAATCCAAGCCGTCCTTGAAGATGCTCAAGAG |
| 151 | AAGCAACTCAACGACAAGCCTCTAGAAAATTGGTTGCAAAAACTCAATGC |
| 201 | TGCTACATATGAAGTCGATGACATCTTGGATGAATATAAAACTAAGGCCA |
| 251 | CAAGATTCTTGCAGTCTGAATATGCCCGTTATCATCCAAAGGTTATCCCT |
| 301 | TTCCGTCACAAGGTTGGGAAAAGGATGGACCAAGTGATGAAAAACTGAA |
| 351 | TGCAATTGCTGAGGAACGAAAGAATTTTCATTTGCAAGAAAAGATTATAC |
| 401 | AGAGACAAGCTGCTACACGGGAAACAGGTACTCATCTTAAATTAGTATTA |
| 451 | CAACTTAGTTTATATTCATTTGTTTTGGGCAATGATCAAATTATGTAAAG |
| 501 | GTCAAATATACTCATGTACTACTGAAAATAGTTTAAATATACCTCTAGTT |
| 551 | ATACTATTAGTACGAACATACTCCTCCCATATACTTTGGAACAAATATTC |
| 601 | CCTTAACGAAATAAGACACGTGAAAGTTCAGATTCAAATTATCCACCCT |
| 651 | CAATTTAAGATCTGATTTCTTTAGGAAACCACTCATCTCCTCCGTTTG |
| 701 | AGTTCTTAACGAAGCAGCTCAGAGAAAAGAGGTTTTCTTCTGTTCTGTTT |
| 751 | CTGCTGCATTTGTGTCTTAATCCAATAACAAACAATACAAATTAATATTA |
| 801 | TGTTCACGATGAGGGTAGTCTTTCTAGCTAGACATGAACTGAGTGTAAAT |
| 851 | TTTGTTTTAAGGAAGAAAAGAAATGATTAGGCTGGATTTCTTTCAGAGT |
| 901 | GGAATATAGGGGATAAAGTTGGAGCATAGAGTTCCATCGTTTATTTCTT |
| 951 | TCCTTAAAGTAACAAGTTCAACAAAATGATATCAAGGTACGGTAATGCAA |
| 1001 | AATTATTAGACACGTCTAAACTACAAAAATGGAATAGAAACTTAAATTAT |
| 1051 | CAGTGACAATATCATCCTTTAATAAAGCTACCAAATTAAATCATGATAC |
| 1101 | AGAGAAGAAACCAAAAAAATTAGGGGTGAATTATTTGATTCTATGCTTAT |
| 1151 | CACATGTCTTCCCATCAACATCAAAGGAAAAATTGTGCCAAAGTATAAAC |
| 1201 | GGTGCGGTATATTTGGATTGAAAGTAAAACAGGAGGATACATTTGGACTA |
| 1251 | AAAGTATAACAATAAGTATATTTGATCATTTTATGTATCAAATTCATGTG |
| 1301 | GTTTTTGGGGAGAAGGGAAGTTTCAATGTTTTCAATCTGCTCCTCATCTC |
| 1351 | ATCCATATCTCTTTATTGTGCAAAACCCTTCTCTATTTAACTATTTTCTG |
| 1401 | CCGACTCCTAATGAGCTTGAATGTAACAATATTCTCATCTGCACATTGCT |

Figure 6E (Continued)

```
1451  TGCACCAGGTTCTGTGTTAACTGAACCACAAGTTTATGGAAGGGACAAAG
1501  AAAAAGATGAGATAGTGAAAATCCTAATAAACAATGTTAGTCATCCCCAA
1551  AAACTCTCAGTCCTCCCAATACTTGGTATGGGGGGACTAGGAAAGACAAC
1601  TCTTTCCCAAATGGTCTTCAATGATCAGAGAGTAACTGAGCGTTTCTATC
1651  CCAAAATATGGATTTGCGTCTCGGATGATTTTGATGAGAAGAGGTTGATA
1701  AAGGCAATAGTAGAATCTATTGAAGGGAAGTCCCTCAGTGACATGGACTT
1751  GGCTCCACTTCAAAACAACCTTCAAGAGTTGCTGAATGGAAAAAGATACT
1801  TCCTTGTCTTAGATGATGTTTGGAATGAAGATCAACATAAGTCGCTAAT
1851  TTAAGAGCAGTCTTGAAGGTTGGAGCAAGTGGTGCATTTGTTCTAACTAC
1901  TACTCGTCTTGAAAAGGTTGGATCAATTATGGAACATTGCAACCATATG
1951  AATTGTCAAATCTGTCTCCAGAGGATTGTTGGTTTTTGTTCATGCAGCGT
2001  GCATTTGGACACCAAGAAGAAATAAATCCAAACCTTGTGGCAATCGGAAA
2051  GGAGATTGTGAAAAATCTCCTGGTGTGCCTCTAGCAGCCAAGACTCTTG
2101  GAGGTATTTTGCGCTTCAAGAGAGAAGAAAGAGAATGGGAACATGTGAGA
2151  GACAGTCCGATTTGGAATTTGCCTCAAGATGAAAGTTCTATTCTGCCTGC
2201  CCTGAGGCTTAGTTACCATCATCTTCCACTTGATTTGAGACAATGCTTTG
2251  TGTATTGTGCGGTATTCCCAAAGGACACCAAAATGGCAAAGGAAAATCTT
2301  ATCGCTTTTTCCATCGCACATGGTTTTCTTTTATCGAAAGGAAATTTGGA
2351  GCTAGAGGATGTAGGTAATGAAGTATGCAATGAATTATACTTGAGGTCTT
2401  TCTTCCAAGAGATTGAAGTTGAATCTGGTAAAACTTATTTCAAGATGCAT
2451  GACCTCATCCATGATTTGGCTACATCTCTGTTTTCAGCAAACACATCAAG
2501  CAGCAATATTCGTGAAATAAATGCTAATTATGATGGATATATGATGTCGA
2551  TTGGTTTTGCTGAAGTGGTATCTTCTTACTCTCCTTCACTCTTGCAAAAG
2601  TTTGTCTCATTAACGCTCCTTAATCTAAGAAACTCGAACCTAAATCAATT
2651  ACCATCTTCCATTGGAGATCTAGTACATTAAGATACCTGGACTTCTCTC
2701  GCAATTTTAGAATTCGTAATCTTCCAAAGAGATTATGCAGGCTTCAAAAT
2751  CTGCAGACTCTTGATCTACATTATTGCGACTCTCTTTCTTGTTTGCCAAA
2801  ACAAACAAGTAAACTTGGTAGTCTCCGAAATCTTTTACTTGATGGCTGTT
2851  CATTCACGTCAACGCCACCAAGGATAGGATTGTTGACATGCCTTAAGTCT
2901  CTAAGTTGCTTTGTTATTGGCAACAGAAAAGGTTATCAACTTCCTGAACT
2951  AAAAAACCTAAATCTCTATGGCTCAATTTCAATCACAAAACTTGACAGAG
3001  TGAAGAAGATAGCGATGCAAAAGAAGCTAATTTATCTGCTAAAGCAAAT
```

Figure 6E (Continued)

```
3051  CTGCACTCTTTATGCCTGAGTTGGGACCTTGATGGAAAACATAGATATCA
3101  TTCAGAAGTTCTTGAAGCCCTCAAACCACACTCCAATCTGAAATATTTAG
3151  AAATCAATGGCTTCGGAGGAATCCGTCTCCCAGATTGGATGAATCAATCA
3201  GTTTTCAAAATGTTGTCTCTATTAGAATTAGAGGTTGTGAAAACTGCTC
3251  ATGCTTACCACCCTTTGGTGAGCTCCCTCTCTAGAAAGTCTAGAGTTAC
3301  ACACCGGGTCAGCAGATGTGGAGTATGTTGAAGATAATCTTCATCCTGGA
3351  AGGTTTCCATCCTTGAGGAAACTTGTTATATGGGACTTTAGTAATCTAAA
3401  AGGATTGCTGAAAAGGAAGGAGAAAAGCAATTCCCTGTGCTTGAAGAGA
3451  TGACATTTTACTGGTGCCCTATGTTTGTTATTCCGACCCTTTCTTCTGTC
3501  AAGACATTGAAACTTATTGCGACAGATGCAACAGTTTTGAGGTCCATATC
3551  TAATCTTAGGGCTCTTACTTCCCTTGACATTACCAATAACGTAGAAGCTA
3601  CTTCACTCCCAGAAGAGATGTTCAAAAGCCTTGCAAATCTCAAATACTTG
3651  AATATCTCTTTCTTTAGGAATCTCAAAGAGTTGCCTACCAGCCTGGCTAG
3701  TCTCAATGCTTTGAAGAGTCTCAAATTTGAATTTTGTAACGCACTAGAGA
3751  GTCTCCAGAGGAAGGGGTGAAAGGTTTAACTTCACTCACCGAGTTGTCT
3801  GTCAGTAACTGTATGATCCTAAATCTTTACCGGAGGGATTGCAGCACCT
3851  AACAGCCCTCACAACTTTAACAATTACTCAATGTCCAATACTATTCAAGC
3901  GGTGTGAGAGAGGAATAGGAGAAGACTGGCACAAAATTGCTCACATTCCA
3951  TATTTGACTCTATATGAGTGA
```

Figure 6F

```
1     ATGGCGGAAGCTTTTCTTCAAGTTCTGCTAGAAAATCTCACTTCTTCAT
51    CCGAGATAAACTTGTATTGATTTTCGGTTTCGAAAAGGAATGTGAAAAGC
101   TGTCGAGTCTGTTTTCCACAATTCAAGCTGTGCTTCAAGATGCTCAGGAG
151   AAGCAATTGAAGGACAAGGCAATTGAGAATTGCTTGCAGAAACTCAATTC
201   TGCTTCTTATGAAGTTGATGATATATTGGGCGAATGTAAAAATCAGGCAA
251   TAAGATTTGAGCAGTCTCGATTAGGGTTTTATCACCCAGGGATTATCAAT
301   TTCCGTCACAAAATTGGGAGAAGGATGAAAGAGATAATGGAGAAACTAGA
351   TGCAATATCTGAGGAAAGAAGGAAGTTTCATTTCCTTGAAAAAATTACAG
401   AGAGACAAGCTGCCGCTGCTACGCCTGAAACAGGTGTGAGTACTGAGTAA
451   TTGTAGCTTAGTTAATATTCAATTTGTTACCACATCATGTGTTCACCGTG
501   ATCTCTACAGTAGGATGGCAATGGGGCTGGGCGAGGTTGGACGTGTGCAG
551   GTGTGTGGCGCAACCCCAACTTTGAGTCTACATAAGTAGGTACTTAAATT
601   TCTATAGAGTTGAACAAGTACAAACGCCTCCTACTTGGTGTCCTTATGCG
651   TATTATGTCACTTAGGATCCATCTGTCTACTTGTTCAACTTTATATGAGT
701   TTAAGTTCTACTTGTGCACACCCAAAGTTGGAGCCCCTAGATGTCAGTTG
751   ATACCAAGTTAAAAAGGCATATTTATGAATTATGCCTTTAAATTATGATT
801   CAATTTTGTATCAGTCTGTCCAAAATATGTTCTAGTGAAAGTGTTAAACT
851   TAGTCTGGATCTGCTATTGAAAGTGAATTTTGTGGCACTAAACAATGCA
901   ATGGGTCTGGATTCATTTTTGCATTAACTTTTGTTTAGACGATTTTCTTT
951   ATCGAATTTTACTGTCTAAAATGCAAAAACCAAAGAAATAAGAAGTATAC
1001  AGAGGCTGACTTCTTCATAGTATCTATCATATAAAAAAAAGCATTGATTA
1051  CTAGGATATGGGTTCTTTTAAATTACAAATTTGTGAGTTAAAACAGTTCT
1101  GTTGGGAAGGATTTAGATACACGTGGATAGTATCTAGAAGTTTTTTAAAT
1151  AAAAAATTAGCAAATTATGCGGGCTGGGCGGGTTGAAAACAGCAAACTT
1201  TGCAAGGCTGGCGGGTCGAAATCTTTGCAAGTTTGTGTGGGTTTGCCCT
1251  GCACCACCCAATCTGCCATTCCTGTCTAAATGTTTGTTTGTCTATAATT
1301  CTTGCTGACTCATTCTAATGAGCTCAATTGTAACAAATTCTTTGTGTCCA
1351  CACTACTTGGAACAGGTTTTGTGTTAACTGAACCAAAAGTCTACGGAAGG
1401  CACAAAGAGGAGGATGAGATAGTGAAAATTCTGATAAACAATGTTAATGT
```

Figure 6F (Continued)

```
1451    TGCCGAAGAACTTCCAGTCTTCCCTATAATTCCTATGGGGGACTAGGAA
1501    AGACGACACTTGCCCAAATGATCTTCAACGATGAGAGAGTAACTAAGCAT
1551    TTCAATCCCAAAATATGGGTTTGTGTCTCAGATGATTTTGATGAGAAGAG
1601    GTTAATTAAGACAATTATAGGAAATATTGAAAGAAGTTCTCCTCATGTTG
1651    AGCACTTCCCTTCATTTCAGAAGAAGCTCCAGGAGTTATTGAATGGAAAA
1701    CGATACTTGCTTGTCTTAGATGATCTTTGGAATGATGATCTAGAAAAGTG
1751    GGCTAAGTTAAGAGCAGTCTTAACTGTTGGAGCAAGAGGTGCTTCTATTC
1801    TAGCTACTACTCGTCTTGAAAGGTTGGATCAATTATGGGAACGTTGCAA
1851    CCATATCATTTGTCAAATTGTCTCCACATGATAGTTTACTTTTGTTTAT
1901    GCAACGCGCATTGGGCAACAAAAAGAAGCAAATCCTAATCTAGTGGCCA
1951    TTGGAAAGCACATTCTCAACAAATGTGGTGGTGTGCCTTTAGCAGCCAAG
2001    ACTCTTGGTGGTCTTTACGCTTCAAGACACAAGAGTGAATGGGAACA
2051    TGTGAGAGATAATGAGATTTGGAGTCTGCCTCAAGATGAAAGTTCTATTT
2101    TGCCTGCTCTAAGACTGAGTTATCATCACCTTCCACTTGATTTGAGACAA
2151    TGCTTTGCGTATTGTGCAGTATTCCCAAAGGACACCAAAATGATAAAGGA
2201    AAATCTCATTACTCTCTGGATGGCGCATGGTTTTCTTTTATCAAAGGGAA
2251    ACTTGGAGCTAGAGGATGTGCCTAATGAAGTATGGAATGAATTATACTTG
2301    AGGTCTTTCTTCCAAGAAATTGAAGCTAAATCGGGTAATACTTATTTCAA
2351    GATACATGATCTAATCCATGATTTGGCTACATCTCTGTTTTCGGCAAGCG
2401    CATCATGCGGCAATATCCGCGAAATAAATGTCAAAGATTATAAGCATACA
2451    GTGTCCATTGGTTTCGCTGCAGTGGTGTCTTCTTACTCTCCTTCGCTCTT
2501    GAAAAACTTTCTCTCCTTAAGGGTGCTTAATCTAAGTTACTCAAAACTTG
2551    AGCAATTACCGTCTTCCATTGGAGATCTATTACATTTAAGATACCTGGAC
2601    CTGTCTTGCAATAACTTCCGTAGTCTTCCAGAGAGGTTGTGCAACCTTCA
2651    AAATCTTCAGACTCTTGATGTACATAATTGCTACTCACTTAATTGTTTGC
2701    CAAAACAAACAAGTAAACTTAGTAGTCTCCGACATCTTGTTGTTGATGGC
2751    TGTCCATTGACTTCTACTCCACCAAGGATAGGATTGTTGACATGCCTTAA
2801    GACTCTAGGTTTCTTTATTGTGGGAACCAACAAAGGTTATCAACTTGGTG
2851    AACTGAAAAACCTAAATCTCTGCGGCTCAATTTCAATCACACACCTTCAG
2901    AGAGTGAAGAACGATACGGATGCAGAAGCCAATTTATCTGCAAAAGCAAA
2951    TCTGCAATCTTTAAGCATGAGTTGGGATAACGATGGACCAAACAGATATG
3001    AATCCAAAGAACTTAAAGTCCTTGAAGCACTCAAACCACACCCCAATCTG
```

Figure 6F (Continued)

```
3051  AAATATTTACAGATCATTGCCTTCGGAGGATTCCGTTTTCCAAGCTGGAT
3101  AAATCACTCAGTTTTGGAGAAGGTCATCTCTCTTACAATTAAAAGCTGCA
3151  AAAACTGCTTGTGCTTACCACCCTTTGGGGAGCTTCCTTGTCTACAAAAT
3201  CTAGAGTTACAAAACGGATCTGCGGAGGTGGAGTATGTTGAAGAGGATGA
3251  TGTCCATTCTAGATTCTCCACAAGAAGAAGCTTTCCATCCCTGAAAAAAC
3301  TTCGTATATGGTTCTTTCGCAGTTTGAAAGGGCTGATGAAAGAGGAAGGA
3351  GAAGAAATTCCCCATGCTTGAAGAGATCGCGATTTTATATTGCCCTCT
3401  GTTTGTTTTTCCAACCCTTTCTTCTGTCAAGAAATTAGAAGTTCACGCCA
3451  ACACAAACACTAGAGGTTTGAGCTCCATATCTAATCTTAGCACTCTTACT
3501  TCCCTCCGCATTGGTGCTAACTACAGAGCGACTTCACTCCCAGAAGAGAT
3551  GTTCACAAGTCTTACAAATCTCGAATTCTTGAGTTTCTTTGACTTCAAGA
3601  ATCTCAAACATCTGCCTACCAGCCTGACTAGTCTCAATGCTTTGAAGCGT
3651  CTCCAAATTGAAAGTTGTGACTCACTAGAGAGTTTCCCTGAACAAGGCT
3701  AGAAGGTTTAACTTCACTCACACAGTTGTTTGTTAAATACTGTAAGATGC
3751  TAAAATGTTTACCCGAGGGATTGCAGCACCTAACAGCCCTCACAAATTTA
3801  GGAGTTTCTGGTTGTCCAGAAGTGGAAAAGCGCTGTGATAAGGAAATAGG
3851  AGAAGACTGGCACAAAATTGCTCACATTCCAAATCTGGATATTCATTAG
```

|   |   |   |
|---|---|---|
| A | MAEAFIQVLLDNLTSFLKGELVLLFGFQDEFQRLSSMFSTIQAVLEDAQEKQLNN | 55 |
|   | KPIENWLQKLNAATYEVDDILDEYKTKATRFSQSEYGRYHPKVIPFRHKVGKRMD | 110 |
|   | QVMKKLKAIAEERKNFH.HEKTVERQAVRRETGSV..FPQVYGRDKEKDETVKTL | 165 |
| B | INNVSDAQHLSVLpilgmgglgkttlaQMVFNDQRVTEHFHSKIWICVSEDFDEK | 220 |
|   | RLIKAIVESTEGRFLLGEMDLAPLQKKLQELLNGkryllvlddvwNEDQQKWANL | 275 |
|   | RAVLKVGASGAsvltttrLEKVGSIMGTIQPYELSNLSQEDCWLLFMQRAFGHQE | 330 |
|   | EINPNLVAIGKEIVKKSGGVPLAANTLGGILCFKREERAWEHVRDSPIWNLPQDE | 385 |
|   | SSILPALRLSYHQLPLDLKQCFAYCAVFPKDAKMEKEKLISLWMAHGFLLSKGNM | 440 |
|   | ELEDVGDEVWKELYLRSFFQEIEVKDGKTYFKmhdllhdlatSLFSANTSSSNIR | 495 |
|   | EINKHS | 501 |
| C | YTHMMEIGFAEVVFFYTLPPLEK | 524 |
|   | FISLRVLNLGDST.FNKLPSSIGD | 547 |
|   | LVHLRYLNLYGSG.MRSLPKQLCK | 570 |
|   | LQNLQTLDLQYCTKLCCLPKETSK | 594 |
|   | LCSLRNLLLDGSQSLTCMPPRIGS | 618 |
|   | LTCLKTLGQFVVGRKKGYQ | 637 |
|   | LCELCNLNLYCSIKISHLERVKNDKDAKEANLSA | 671 |
|   | KGNLHSLSMSWNNFGPHIYESEEVKVLEALKP | 703 |
|   | HSNLTSLKIYCFRCIH.LPEWMNESV | 728 |
|   | LKNIVSILISNFRNCSCLPPFGD | 751 |
|   | LPCLESLELIWGSAD | 766 |
|   | VEYVEEVDIDVHSGFPTRIR | 786 |
|   | FPSLRKLDIWDFCBLKCLLKKECEEQ | 812 |
|   | FPVLEEMIIHECPFLT.LSSN | 832 |
|   | LRALTSLRICYNKVATSFPEEMFKN | 857 |
|   | LANLKYLTISRCNNLKELPTSLAS | 881 |
|   | LNALKSLKIQLCCALESLPEEGLEG | 906 |
|   | LSSLTELFVEHCNMLKCLPEGLOH | 930 |
|   | LTTLTSLKIRGCPQLIKRCEKGIGEDWHK | 959 |
|   | ISHIPNVNIYI | 970 |

```
L..L..L.L..C..α...αP..   LRR consensus
     N
   S
```

```
Rpi-blb    RGIHLPEWMNHSVLKNIVSILISNFRNCSCLPPFGDLPCLFSLRLHWGSADVEYVEEVCI    775
RGC3-blb   G   R  D   Q      V   R  RCCE        E         T          DN--    769
RGC1-blb   C   FC D          V      GCE         E          QD VE     DS--    779
RGC4-blb   G   FRF S C       EKVI VR KSCK   L.  R     N    QN    E    D--    824

Rpi-blb    DVHSGEPTRIRFPSLRKLDIWDFGSLKGLLKKEGEEQFPVLEEMIIHECPFLTLS-----   830
RGC3-blb   -   P  -----        V   SN            K           TPYW    MPVIPTLDDV   823
RGC1 blb   ----    L  R        H GG CN    QRYX A          K  SU      MFVNPTLSSV   835
RGC4-blb         R S  RS     K  R  F R       M E    K  Y     A LY    LFVFPTISSV   884

Rpi-blb    ---------------SNLKALTSLRICYNKVATSFEEEMFKNLANLKYLTISRCHNLK    873
RGC3-blb   KTLKVI-ATDATVLRST          D  SV UR    L       S      N   PER    882
RGC1-blb   KKLEIWCEADAGGLSSI     ST      K FS HTV LL          E  I   SV FLE   895
RGC4-blb   KKLEVHGNTNTRGLSSI     ST      GA YR    L           TS T   EF SFPDRK  944

Rpi-blb    ELFTSLASLNALKSLRIQLCCALESLPEEGLEGLSSLTELFVEHCNMLKCLPEGLQRLTT   933
RGC3-blb                   FEF N           VK  T        S  SN M              A    942
RGC1-blb              N    C D RY  Y                                               950
RGC4-blb   D      I        R Q ES DS    F Q        T    Q   KY K              A   1004

Rpi blb    LTSLKIRGCPQLIKECEKGIGEDWHKISHIPNVNIYI                         970
RGC3-blb      T  T TQ  IVF     R             A       YLTL E                979
RGC1-blb                                                                    999
RGC4-blb               N GVS    EVE     D E             A     LD H-        1040
```

```
B149-blb         S              N  N           G  S              N       486
SH20-tub         RR L           RN Q N            RY N                   483
T118-tar         RR L           N  N              RY N                   483
RGA4-blb            L           N  N           A S N     I               533

Rpi-blb    ANTSSSNIREINKM----------G TRNTSIGFASVVFFYTLPPLBKFISLRVINLQDS   536
RGA3-blb         AN------YDGY           SS SPSL Q  V          RN         535
SH10-tub   S     VK----------Q P X    T SS SPSLSQ  V          ANL        537
RGA1-blb   SR RS Q VKDDEDMMFIVIN KD    S SS SPSLVKR Y          SN         545
B149-blb   SA RS Q VKDDEDMMFIVIN KD    S SS SPSLFKR V          SN         545
SH20-tub         VE----------          R SS SPSL O  V          SY        534
T118-tar         VE----------          G GG GPGL Q  V          GY        534
RGA6-blb   SA CG VK----------D K TV   A SS SPSL K  V          SY         549

Rpi-blb    TPSRLPSSIGDLVRLRYLNLYG SGNRDLPKQLOKLQNLQTLDLQVCTKLCCLPKSTCKL   605
RGA3-blb   NL Q            D S NFRL N    K K           R DS G       Q    595
SH10-tub   K EE S          N C D SEN I                 JRN YS S     P    597
RGA1-blb   E EQ   V          D S -NKIC     R           YN QS S         Q 604
B149-blb   E EQ   V          D S -NKIC     K     K     YN QS S         Q 604
SH20-tub   K EE             NG SNFIRI                    R            Q  594
T118-tar   K EE             NG SDNIRI                    R            Q  594
RGA4-blb   KLEQ      L       G SC-NMP     ER           VRN YS N       Q  649

Rpi-blb    CSLRNLLIDGSQSLTNMPPRIGSLTFCTKTT CQRVKCPKKRYQL GRIGNLNLYGSIKIEHL 665
RGA3-blb            -C    BT      L     S SG  I KR         K       D TK  654
SH10-tub           FFW CDE NS         F     ENICE I       K RDV     N T  656
RGA1-blb   C        V N-CP  S        L       Y     ER      R     R A S T 663
B149-blb   C        V DH CD  S        L       Y     ER      R     R A S T 663
SH20-tub            N CRR  RT                      S K              S    654
T118-tar            N CRR  RT                                       S    654
RGA4-blb   G      H VV   CP  GT       L       F I  G       K    C   S T  707

Rpi-blb    ERVFMDYDASKANLSAVGNLESLGMSWNNFGPHIVESEBVKVLSACKPHSNLTSLKIVGP   735
RGA3-blb   D     K S          A     CL  DSD K R D  ---E         KN M     721
SH10-tub         VN                I N SRKG           R I       P CT S   716
RGA1-blb         MR              A         D--R  R             P  KY E ID 721
B149-blb         MQ              A         D  R NR              P  KY E ID 719
SH20-tub         E               E        K DDDE  R         E      C S   713
T118-tar         R               E        K DDDE  R         E      C T G 713
RGA4-blb         T              A Q       D G NR    K          D  KY E IA 766

Rpi-blb    RGIHLPEWMDHSVLKNIVSILISNFRNCSCLPPFGDLPCLESLELHWGSADHEYVEEVDI   775
RGA3-blb   G  R D  Q       V   R RGCS       E            T          DN-- 769
SH10-tub     FRF            V   E  GCK       E    KR   QK  E        D--- 774
RGA1-blb   C FC D            V      GCE       E           QD VE      DS--  779
B149-blb   C FC D            V      GCE       E           QD VE      D--- 770
SH20-tub     R D            L E GCK                        YR        --  775
T118-tar     R D            L E GCK                      Q YR        --  773
RGA4-blb   G RRF G I     SKUI VR KGFK   L      R       M  QN  P       D--  824

Rpi-blb    EVHSGPPTRIRFPSLRKLDINDFGSLKGILKKKEGERQFPVLKKNH IRKCPYUTLS-----   850
RGA3-blb   -- F -----          V   SN             K          FYW KFVIPTLSSV 823
SH10-tub   ---  R              P GD PN              R G DY IDSPVNTTL --  820
RGA1-blb   ---  L  K           H GG LN    QRMK   K         K SD KFVKPPLSSV 825
B149-blb   ---  L  R           H GG CN    QRMK   A         K SD KFVFPTLSSV 832
SH20-tub   D     L             C CK DN            G         E RY ID ----- 827
T118-tar   D                   C CK DN     V      G         E RY IP ----- 828
RGA4-blb        RS R8    K  R F R       M E      K  M    A LY LFVPPTLSSV  864

Rpi-blb    ---------------ENLRALTGLRIOVNKVATGFREMDFRNLANLRYLTISRGNRLN   873
RGA3-blb   KTLSVI-AIDDATVLRSI    D EN VE   L       S        N  FFN     892
SH10-tub   ------------------ F      H SH NS    L  I  SF         K  LFY  869
RGA1-blb   MKLDTKGRADAGGLSSI    ST    K PD HTV   LL         S  I  SV PLS  895
B149-blb   KKLEIKGRADAGGLSSI    ST    K MR HIV   LL         S  I  SV RLS  892
SH20-tub   -----------------P K      N SD E         S           N HFK    866
T118-tar   -----------------  K      M SD E        KS           N HPK    869
RGA4-blb   RNLEVHGNTNTRGLSSI    ST    GA YR    L      TS T    EF SFFPFK   944

Rpi-blb    ELPTSIABYNALKSLKIQLCCALESLPRRGLRGLSSITRLRVRECNMLKOLDRGLQHY.FT 933
RGA3-blb            DBP N             VK  T      D SN M                A  942
SH10-tub    S   C       T E HS  S           VK  T      TU E    F       A  929
RGA1-blb           N C D RY Y                                              955
B149-blb           N C D RY Y                                              952
SH20-tub                 W         NS K  VK  T      I NFSSV        N R    921
T118-tar                 W         I     VK  T      I KF  K                A 929
```

Figure 10B (Continued)

```
RGA4-blb    D     T          K Q ES DS    P   Q       T   Q   KY K              A   1004

Rpi-blb     LPSLKIRGCPQLIKRCEKGIGEDWHKISHIPNVNIYI                                    970
RGA3-blb         T T TQ  YVF        R          A    YLIL K                           979
SH10-tub              L R                 --------------------                       948
RGA1-blb                                                                             992
B1tb-blb                                  -------------.                             871
SH20-tub    R     W                       ----------------------                     947
T11B-car    RV    W                       ----------------------                     948
RGA4-blb    N GVS      SVS     J R            A       LD H                          1040
```

ISOLATED NUCLEIC ACIDS ENCODING RESISTANCE POLYPEPTIDES AND USES THEREOF

RELATED APPLICATIONS

The present application claims benefit to European application EP 02075565.8 filed Feb. 8, 2002.

FIELD OF THE INVENTION

The invention relates to the field of plant diseases.

BACKGROUND OF THE INVENTION

Late blight, caused by the oomycete pathogen *Phytophthora infestans* is world-wide the most destructive disease for potato cultivation. The disease also threatens the tomato crop. The urgency of obtaining resistant cultivars has intensified as more virulent, crop-specialised and pesticide resistant strains of the pathogen are rapidly emerging.

A way to prevent crop failures or reduced yields is the application of fungicides that prevent or cure an infection by *P. infestans*. However, the application of crop protectants is widely considered to be a burden for the environment. Thus, in several Western countries, legislation is becoming more restrictive and partly prohibitive to the application of specific fungicides, making chemical control of the disease more difficult. An alternative approach is the use of cultivars that harbour partial or complete resistance to late blight. Two types of resistance to late blight have been described and used in potato breeding. One kind is conferred by a series of major, dominant genes that render the host incompatible with specific races of the pathogen (race specific resistance). Eleven such R genes (R1–R11) have been identified and are believed to have originated in the wild potato species *Solanum demissum*, which is native to Mexico, where the greatest genetic variation of the pathogen is found. Several of these R genes have been mapped on the genetic map of potato (reviewed in Gebhardt and Valkonen, 2001 Annu. Rev. Phytopathol. 39: 79–102). R1 and R2 are located on chromosomes 5 and 4, respectively. R3, R6 and R7 are located on chromosome 11. Unknown R genes conferring race specific resistance to late blight have also been described in *S. tuberosum* ssp. andigena and *S. berthaultii* (Ewing et al., 2000 Mol. Breeding 6: 25–36). Because of the high level of resistance and ease of transfer, many cultivars contain *S. demissum* derived resistance. Unfortunately, *S. demissum* derived race specific resistance, although nearly complete, is not durable. Once newly bred cultivars are grown on larger scale in commercial fields, new virulences emerge in *P. infestans* that render the pathogen able to overcome the introgressed resistance. The second type of resistance, termed field resistance and often quantitative in nature, is thought to be race non-specific and more durable. Field resistance to late blight can be found in several Mexican and Middle and South American *Solanum* species (Rossi et al., 1986 PNAS 95:9750–9754).

Diploid *S. bulbocastanum* from Mexico and Guatemala is one of the tuber bearing species that is known for its high levels of field resistance to late blight (Niederhauser and Mills, 1953 Phytopathology 43: 456–457). Despite differences in endosperm balance numbers, introgression of the *S. bulbocastanum* resistance trait has been successful. Ploidy manipulations and a series of tedious bridge crosses has resulted in *S. bulbocastanum* derived, *P. infestans* resistant germplasm (Hermsen and Ramanna, 1969 Euphytica 18:27–35; 1973 Euphytica 22:457–466; Ramanna and Hermsen, 1971 Euphytica 20:470–481; Hermsen and De Boer, 1971 Euphytica 20:171–180). However, almost 40 years after the first crosses and intense and continuous breeding efforts by potato breeders in the Netherlands with this germplasm, late blight resistant cultivars still remain to be introduced on the market. Successful production of somatic hybrids of *S. bulbocastanum* and *S. tuberosum* has also been reported (Thieme et al., 1997 Euphytica 97(2):189–200; Helgeson et al., 1998 Theor Appl. Genet 96:738–742). Some of these hybrids and backcrossed germplasm were found to be highly resistant to late blight, even under extreme disease pressure. Despite reports of suppression of recombination, resistance in the backcrossed material appeared to be on chromosome 8 within an approximately 6 cM interval between the RFLP markers CP53 and CT64 (Naess et al., 2000 Theor. Appl Genet 101: 697–704). A CAPS marker derived from the tomato RFLP probe CT88 cosegregated with resistance. Suppression of recombination between the *S. bulbocastanum* and *S. tuberosum* chromosomes forms a potential obstacle for successful reconstitution of the recurrent cultivated potato germplasm to a level that could meet the standards for newly bred potato cultivars. Isolation of the genes that code for resistance found in *S. bulbocastanum* and subsequent transformation of existing cultivars with these genes, would be a much more straight forward and quicker approach when compared to introgression breeding.

The cloning and molecular characterisation of numerous plant R genes conferring disease resistance to bacteria, fungi, viruses, nematodes, and insects has identified several structural features characteristic to plant R genes (reviewed in Dangl and Jones, 2001 Nature 411, 826–833). The majority are members of tightly linked multigene families and all R genes characterised so far, with the exception of Pto, encode leucine-rich repeats (LRRs), structures shown to be involved in protein-protein interactions. LRR containing R genes can be divided into two classes based on the presence of a putative tripartite nucleotide-binding site (NBS). R genes of the NBS-LRR class comprise motifs that are shared with animal apoptosis regulatory proteins (van der Biezen et al., 1998 Curr. Biol. 8, 226–227; Aravind et al., 1999 Trends Biochem. Sci. 24, 47–53) and can be subdivided into two subgroups based on their N-terminal domain, which either exhibits sequence similarity to the *Drosophila* Toll protein and the mammalian interleukin-1 receptor domain (TIR-NBS-LRR), or contains a potential leucine zipper or coiled-coil domain (CC-NBS-LRR; Pan et al., 2000 Genetics. 155:309–22). LRR R genes without an NBS encode transmembrane proteins, whose extracellular N-terminal region is composed of LRRs (Jones et al., 1994 Adv. Bot. Res.24, 89–167). These genes can be divided into two subgroups based on the presence of a cytosolic serine/threonine kinase domain (Song et al., 1995 Science, 270, 1804–1806). Four R genes have currently been cloned from potato. All four, including the *S. demissum* derived R1 gene conferring race specific resistance to late blight, belong to the CC-NBS-LRR class of plant R genes (Bendahmane et al., 1999 Plant Cell 11, 781–791; Bendahmane et al., 2000 Plant J. 21, 73–81; van der Vossen et al., 2000 Plant Journal 23, 567–576; Ballvora et al., 2002 Plant Journal 30, 361–371).

The invention provides an isolated or recombinant nucleic acid comprising a nucleic acid coding for the amino acid sequence of FIG. 8 (SEQ ID NO: 54) or a functional fragment or a homologue thereof. The protein coded by said amino acid has been detected as being member of a cluster of genes identifiable by phylogenetic tree analysis, which thus far consists of the proteins Rpi-blb, RGC1-blb, RGC3-blb and RGC4-blb (herein also called the Rpi-blb gene cluster) of FIG. 9.

Phylogenetic tree analysis is carried out as follows. First a multiple sequence alignment is made of the nucleic acid sequences and/or preferably of the deduced amino acid sequences of the genes to be analysed using CLUSTALW, which is in standard use in the art. ClustalW produces a .dnd file, which can be read by TREEVIEW. The phylogenetic tree depicted in FIG. 9A is a phylogram.

Phylogenetic studies of the deduced amino acid sequences of Rpi-blb, RGC1-blb, RGC3-blb, RGC4-blb and those of the most similar genes from the art (as defined by the BLASTX) derived from diverse species, using the Neighbour-Joining method of Saitou and Nei (1987 Molecular Biology and Evolution 4, 406–425), shows that corresponding genes or functional fragments thereof of the Rpi-blb gene cluster can be placed in a separate branch (FIG. 9A).

Sequence comparisons between the four members of the Rpi-blb gene cluster identified on 8005-8 BAC clone SPB4 show that sequence homology within the Rpi-blb gene cluster varies between 70% and 81% at the amino acid sequence level. The deduced amino acid sequence of Rpi-blb shares the highest overall homology with RGC3-blb (81% amino-acid sequence identity; Table 4). When the different domains are compared it is clear that the effector domains present in the N-terminal halves of the proteins (coiled-coil and NBS-ARC domains) share a higher degree of homology (91% sequence identity) than the C-terminal halves of these proteins which are thought to contain the recognition domains (LRRs; 71% amino acid sequence identity). Comparison of all four aminoacid sequences revealed a total of 104 Rpi-blb specific amino acid residues (FIG. 10). The majority of these are located in the LRR region (80/104). Within the latter region, these specific residues are concentrated in the LRR subdomain xxLx-Lxxxx (SEQ ID NO: 1). The relative frequency of these specific amino-acid residues within this LRR subdomain is more than two times higher (28.3%) than that observed in the rest of the LRR domain (12.3%). The residues positioned around the two conserved leucine residues in the consensus xxLxxLxxxx (SEQ ID NO: 2) are thought to be solvent exposed and are therefore likely to be involved in creating/maintaining recognition specificity of the resistance protein.

Sequences of additional members of the Rpi-blb gene cluster can be obtained by screening genomic DNA or insert libraries, e.g. BAC libraries with primers based on signature sequences of the Rpi-blb gene. Screening of various *Solanum* BAC libraries with primer sets A and/or B (Table 2 and FIG. 7) identified numerous Rpi-blb homologues derived from different *Solanum* species. Alignment of these additional sequences with those presented in FIG. 10 will help identify additional members of the Rpi-blb gene cluster and specific amino acid residues therein responsible for *P. infestans* resistance specificity. Furthermore, testing additional sequences in the above described phylogenetic tree analyses, e.g. using the Neighbour-Joining method of Saitou and Nei (1987 Molecular Biology and Evolution 4, 406–425), provides additional identification of genes belonging to the Rpi-blb gene cluster.

The invention provides the development of an intraspecific mapping population of *S. bulbocastanum* that segregated for race non-specific resistance to late blight. The resistance was mapped on chromosome 8, in a region located 0.3 cM distal from CT88. Due to the race non-specific nature of the resistance, *S. bulbocastanum* late blight resistance has always been thought to be R gene independent. However, with the current invention we demonstrate for the first time that *S. bulbocastanum* race non-specific resistance is in fact conferred by a gene bearing similarity to an R gene of the NBS-LRR type.

The invention further provides the molecular analysis of this genomic region and the isolation by map based cloning of a DNA-fragment of the resistant parent that harbours an R gene, designated Rpi-blb. This DNA-fragment was subcloned from an approximately 80 kb bacterial artificial chromosome (BAC) clone which contained four complete R gene-like sequences in a cluster-like arrangement. Transformation of a susceptible potato cultivar by *Agrobacterium tumefaciens* revealed that one of the four R gene-like sequences corresponds to Rpi-blb that provides the race non-specific resistance to late blight. Characterisation of the Rpi-blb gene showed that it is a member of the NBS-LRR class of plant R genes. The closest functionally characterised sequences of the prior art are members of the I2 resistance gene family in tomato. These sequences have an overall amino acid sequence identity of approximately 32% with that of Rpi-blb.

Thus, in a first embodiment, the invention provides an isolated or recombinant nucleic acid, said nucleic acid encoding a gene product having the sequence of Rpi-blb or a functional fragment thereof that is capable of providing a member of the Solanaceae family with race non-specific resistance against an oomycete pathogen.

Isolation of the gene as provided here that codes for the desired resistance trait against late blight and subsequent transformation of existing potato and tomato cultivars with this gene now provides a much more straightforward and quicker approach when compared to introgression breeding. The results provided here offer possibilities to further study the molecular basis of the plant pathogen interaction, the ecological role of R genes in a wild Mexican potato species and are useful for development of resistant potato or tomato cultivars by means of genetic modification.

In contrast to the R genes cloned and described so far, the gene we provide here is the first isolated R gene from a *Solanum* species that provides race non-specific resistance against an oomycete pathogen. Notably, the invention provides here a nucleic acid wherein said *Solanum* species that is provided with the desired resistance comprises *S. tuberosum*. In particular, it is the first gene that has been isolated from a phylogenetically distinct relative of cultivated potato, *S. bulbocastanum*, for which it was shown by complementation assays, that it is functional in *S. tuberosum*. These data imply that the gene Rpi-blb can easily be applied in potato production without a need for time-consuming and complex introgression breeding.

The following definitions are provided for terms used in the description and examples that follow.

Nucleic acid: a double or single stranded DNA or RNA molecule.

Oligonucleotide: a short single-stranded nucleic acid molecule.

Primer the term primer refers to an oligonucleotide that can prime the synthesis of nucleic acid.

Homology: homology is the term used for the similarity or identity of biological sequence information. Homology may be found at the nucleotide sequence and/or encoded amino acid sequence level. For calculation of precentage identity the BLAST algorithm can be used (Altschul et al., 1997 Nucl. Acids Res. 25:3389–3402) using default parameters or, alternatively, the GAP algorithm (Needleman and Wunsch, 1970 J. Mol. Biol. 48:443–453), using default parameters, which both are included in the Wisconsin Genetics Software Package, Genetics Computer Group (GCG), 575 Science Dr., Madison, Wis., USA. BLAST searches assume that proteins can be modelled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, 1993 Comput. Chem. 17:149–163) and XNU (Claverie and States, 1993 Comput. Chem. 17:191–201) low-complexity filters can be employed alone or in combination. As used herein, 'sequence identity' or 'identity' in the context of two protein sequences (or nucleotide sequences) includes reference to the residues in the two sequences which are the same when aligned for maximum correspondence over a specified comparison window. When percentage of sequence identity is used in reference to proteins it is recognised that residue positions which are not identical often differ by conservative amino acid substitutions, where amino acids are substituted for other amino acid residues with similar chemical properties (e.g. charge or hydrophobicity) and therefore do not change the functional properties of the molecule. Where sequences differ in conservative substitutions, the percentage sequence identity may be adjusted upwards to correct for the conservative nature of the substitutions. Sequences, which differ by such conservative substitutions are said to have 'sequence similarity' or 'similarity'. Means for making these adjustments are well known to persons skilled in the art. Typically this involves scoring a conservative substitution as a partial rather than a full mismatch, thereby increasing the percentage sequence identity. Thus, for example, where an identical amino acid is given a score of 1 and a non-conservative substitution is give a score of zero, a conservative substitution is given a score between 0 and 1. The scoring of conservative substitutions is calculated, e.g. according to the algorithm of Meyers and Miller (Computer Applic. Biol. Sci. 4:11–17, 1988).

As used herein, 'percentage of sequence identity' means the value determined by comparing two optimally aligned sequences over a comparison window, wherein the portion of the amino acid sequence or nucleotide sequence in the comparison window may comprise additions or deletions (i.e., gaps) as compared to the reference sequence for optimal alignment of the two sequences. The percentage is calculated by determining the number of positions at which the identical amino acid or nucleic acid base residue occurs in both sequences to yield the number of matched positions, dividing the number of matched positions by the total number of positions in the window of comparison and multiplying the result by 100 to yield the percentage of sequence identity. Preferably the amino acid sequence of the protein of the invention shares at least 82% or higher homology with the sequence as depicted in FIG. 8. As shown in Table 4, the closest functionally characterised sequence of the prior art (members of the 12 Fusarium resistance gene cluster in tomato) has a much lower level of amino acid sequence identity than this (32% with respect to that of Rpi-blb). Homology within the gene cluster of the present invention varies between 70% and 81% at the amino acid sequence level.

Homologous nucleic acid sequences are nucleic acid sequences coding for a homologous protein defined as above. One example of such a nucleic acid is the sequence as provided in FIG. 6A. However, there are many sequences which code for a protein which is 100% identical to the protein as depicted in FIG. 8. This is due to the 'wobble' in the nucleotide triplets, where more than one triplet can code for one and the same amino acid. Thus, even without having an effect on the amino acid sequence of the protein the nucleotide sequence coding for this protein can be varied substantially. It is acknowledged that nucleotide sequences coding for amino acid sequences that are not 100% identical to said protein can contain even more variations. Therefore, the percentage identity on nucleic acid sequence level can vary within wider limits, without departing from the invention.

Promoter. the term "promoter" is intended to mean a short DNA sequence to which RNA polymerase and/or other transcription initiation factors bind prior to transcription of the DNA to which the promoter is functionally connected, allowing transcription to take place. The promoter is usually situated upstream (5') of the coding sequence. In its broader scope, the term "promoter" includes the RNA polymerase binding site as well as regulatory sequence elements located within several hundreds of base pairs, occasionally even further away, from the transcription start site. Such regulatory sequences are, e.g., sequences that are involved in the binding of protein factors that control the effectiveness of transcription initiation in response to physiological conditions. The promoter region should be functional in the host cell and preferably corresponds to the natural promoter region of the Rpi-blb resistance gene. However, any heterologous promoter region can be used as long as it is functional in the host cell where expression is desired. The heterologous promoter can be either constitutive or regulatable, tissue specific or not specific. A constitutive promoter such as the CaMV 35S promoter or T-DNA promoters, all well known to those skilled in the art, is a promoter which is subjected to substantially no regulation such as induction or repression, but which allows for a steady and substantially unchanged transcription of the DNA sequence to which it is functionally bound in all active cells of the organism provided that other requirements for the transcription to take place is fulfilled. It is possible to use a tissue-specific promoter, which is driving expression in those parts of the plant which are prone to pathogen infection. In the case of *Phytophthora* a promoter which drives expression in the leaves, such as the ferredoxin promoter, can be used. A regulatable promoter is a promoter of which the function is regulated by one or more factors. These factors may either be such which by their presence ensure expression of the relevant DNA sequence or may, alternatively, be such which suppress the expression of the DNA sequence so that their absence causes the DNA sequence to be expressed. Thus, the promoter and optionally its associated regulatory sequence may be activated by the presence or absence of one or more factors to affect transcription of the DNA sequences of the genetic construct of the invention. Suitable promoter sequences and means for obtaining an increased transcription and expression are known to those skilled in the art.

Terminator: the transcription terminator serves to terminate the transcription of the DNA into RNA and is preferably selected from the group consisting of plant transcription terminator sequences, bacterial transcription terminator sequences and plant virus terminator sequences known to those skilled in the art.

Gene: the term "gene" is used to indicate a DNA sequence which is involved in producing a polypeptide chain and which includes regions preceding and following the coding region (5'-upstream and 3'-downstream sequences) as well as intervening sequences, the so-called introns, which are placed between individual coding segments (so-called exons) or in the 5'-upstream or 3'-downstream region. The 5'-upstream region may comprise a regulatory sequence that controls the expression of the gene, typically a promoter. The 3'-downstream region may comprise sequences which are involved in termination of transcription of the gene and optionally sequences responsible for polyadenylation of the transcript and the 3' untranslated region. The term "resistance gene" is an isolated nucleic acid according to the invention said nucleic acid encoding a gene product that is capable of providing a plant with resistance against a pathogen, more specifically said plant being a member of the Solanaceae family, more preferably potato or tomato, said pathogen more specifically being an oomycete pathogen, more specifically *Phytophthora*, more specifically *Phytophthora infestans*, said nucleic acid preferably comprising a sequence as depicted in FIG. 8 or part thereof, or a homologous sequence with essentially similar functional and structural characteristics. A functionally equivalent fragment of such a resistance gene or nucleic acid as provided by the invention encodes a fragment of a polypeptide having an amino acid sequence as depicted in FIG. 8 or part thereof, or a homologous and/or functionally equivalent polypeptide, said fragment exhibiting the characteristic of providing at least partial resistance to an oomycete infection such as caused by *P. infestans* when incorporated and expressed in a plant or plant cell.

Resistance gene product: a polypeptide having an amino acid sequence as depicted in FIG. 8 or part thereof, or a homologous and/or functionally equivalent polypeptide exhibiting the characteristic of providing at least partial resistance to an oomycete infection such as caused by *P. infestans* when incorporated and expressed in a plant or plant cell.

Functionally equivalents of the protein of the invention are proteins that are homologous to and are obtained from the protein depicted in FIG. 8 by replacing, adding and/or deleting one or more amino acids, while still retaining their pathogen resistance activity. Such equivalents can readily be made by protein engineering in vivo, e.g. by changing the open reading frame capable of encoding the protein so that the amino acid sequence is thereby affected. As long as the changes in the amino acid sequences do not altogether abolish the activity of the protein such equivalents are embraced in the present invention. Further, it should be understood that equivalents should be derivable from the protein depicted in FIG. 8 while retaining biological activity, i.e. all, or a great part of the intermediates between the equivalent protein and the protein depicted in FIG. 8 should have pathogen resistance activity. A great part would mean 30% or more of the intermediates, preferably 40% or more, more preferably 50% or more, more preferably 60% or more, more preferably 70% or more, more preferably 80% or more, more preferably 90% or more, more preferably 95% or more, more preferably 99% or more.

Preferred equivalents are equivalents in which the leucine rich repeat region is highly homologous to the LRR region as depicted in FIG. 8. Other preferred equivalents are equivalents wherein the N-terminal effector domain is essential the same as the effector domain of Rpi-blb.

The protein of the invention comprises a distinct N-terminal effector domain and a leucine rich repeat domain. It is believed that conservation of these regions is essential for the function of the protein, although some variation is allowable. However, the other parts of the protein are less important for the function and may be more susceptible to change.

In order to provide a quick and simple test if the modified proteins and/or the gene constructs capable of expressing said modified proteins which are described here or any new constructs which are obvious to the person skilled in the art after reading this application indeed can yield a resistance response the person skilled in the art can perform a rapid transient expression test known under the name of ATTA (*Agrobacterium tumefaciens* Transient expression Assay). In this assay (of which a detailed description can be found in Van den Ackerveken, G., et al., Cell 87, 1307–1316, 1996) the nucleotide sequence coding for the modified protein which is to be tested is placed under control of the CaMV 35S promoter and introduced into an *Agrobacterium* strain which is also used in protocols for stable transformation. After incubation of the bacteria with acetosyringon or any other phenolic compound which is known to enhance *Agrobacterium* T-DNA transfer, 1 ml of the *Agrobacterium* culture is infiltrated into an in situ plant leaf (from e.g. a tobacco or potato or tomato plant) by injection after which the plants are placed in a greenhouse and infected with a pathogen, preferably *P. infestans*. After 2–5 days the leaves can be scored for occurrence of resistance symptoms.

In the present invention we have identified and isolated the resistance gene Rpi-blb, which confers race non-specific resistance to *Phytophthora infestans*. The gene was cloned from a *Solanum bulbocastanum* genotype that is resistant to *P. infestans*. The isolated resistance gene according to the invention can be transferred to a susceptible host plant using *Agrobacterium* mediated transformation or any other known transformation method, and is involved in conferring the host plant resistant to plant pathogens, especially *P. infestans*. The host plant can be potato, tomato or any other plant, in particular a member of the Solanaceae family that may be infected by such a plant pathogen. The present invention provides also a nucleic acid sequence coding for this protein or a functional equivalent thereof, preferably comprising the Rpi-blb gene, which is depicted in FIG. 6 (SEQ ID NOs: 48, 49, 50, 51, 52 and 53).

With the Rpi-blb resistance protein or functionally equivalent fragment thereof according to the invention, one has an effective means of control against plant pathogens, since the gene coding for the protein can be used for transforming susceptible plant genotypes thereby producing genetically transformed plants having a reduced susceptibility or being preferably resistant to a plant pathogen. In particular, a plant genetically transformed with the Rpi-blb resistance gene according to the invention has a reduced susceptibility to *P. infestans*.

In a preferred embodiment the Rpi-blb resistance gene comprises the coding sequence provided in FIG. 6A or any homologous sequence or part thereof preceded by a promoter region and/or followed by a terminator region. The promoter region should be functional in plant cells, and preferably correspond to the native promoter region of the Rpi-blb gene. However, a heterologous promoter region that is functional in plant cells can be used in conjunction with the coding sequences.

In addition the invention relates to the Rpi-blb resistance protein which is encoded by the Rpi-blb gene according to the invention and which has an amino acid sequence provided in FIG. 8, or a functional equivalent thereof.

The signal that triggers the expression of the resistance gene in the wild-type *S. bulbocastanum* or in the transgenic plants of the invention is probably caused by the presence of a pathogen, more specifically the pathogen *P. infestans*. Such systems are known for other pathogen-plant interactions (Klement, Z., In: Phytopathogenic Prokaryotes, Vol. 2, eds.: Mount, M. S. and Lacy, G. H., New York, Academic Press, 1982, pp. 149–177), and use of this system can be made to increase the applicability of the resistance protein resulting in a resistance to more pathogens (see EP 474 857). This system makes use of the elicitor compound derived from the pathogen and the corresponding resistance gene, wherein the resistance gene when activated by the presence of the elicitor would lead to local cell death (hypersensitive reaction). In case of the present resistance gene, the corresponding elicitor component has not yet been disclosed, but it is believed that this is achievable by a person skilled in the art. Once the elicitor component is isolated it will be possible to transform the gene coding for said elicitor together with the gene coding for the resistance protein into plant, whereby one of the genes is under control of a pathogen-inducible promoter. These promoters are well known in the art (e.g. prp1, Fis1, Bet v 1, Vst1, gstA1, and sesquiterpene cyclase, but any pathogen-inducible promoter which is switched on after pathogen infection can be used). If the transgenic plant contains such a system, then pathogen attack which is able to trigger the pathogen-inducible promoter will cause production of the component which is under control of said promoter, and this, in connection with the other component being expressed constitutively, will cause the resistance reaction to occur.

It will also be possible to mutate the resistance protein causing it to be in an active state (see EP1060257). Since this would permanently result in the resistance reaction to occur, which ultimately leads to local cell death, care should be taken not to constitutively express the resistance protein. This can be accomplished by placing the mutated resistance protein under control of a pathogen-inducible promoter, which not only would allow for expression of the active resistance protein only at times of pathogen attack, but would also allow a broader pathogen range to induce the hypersensitive reaction. Mutation of threonine and serine residues to aspartic acid and glutamic acid residues frequently leads to activation, as was shown in many proteins of which the activity is modulated by phosphorylation, e.g. in a MAPK-activated protein (Engel et al., 1995, J. Biol. Chem. 270, 27213–27221), and in a MAP-kinase-kinase protein (Huang et al., 1995 Mol. Biol. Cell 6, 237–245). Also C- and N-terminal as well as internal deletion mutants of these proteins can be tested for suitable mutants.

A more undirected way of identifying interesting mutants of which constitutive activity is induced is through propagation of the protein-encoding DNA in so-called *E. coli* 'mutator' strains.

A rapid way of testing all made mutants for their suitability to elicit a hypersensitive response is through a so-called ATTA assay (Van den Ackerveken, G., et al., Cell 87, 1307–1316, 1996). Many mutants can be screened with low effort to identify those that will elicit an HR upon expression.

The invention also provides a vector comprising a nucleic acid as provided herein, said nucleic acid encoding a gene product that is capable of providing a member of the Solanaceae family with resistance against an oomycete pathogen, or a functionally equivalent isolated or recombinant nucleic acid in particular wherein said member comprises *S. tuberosum* or *Lycopersicon esculentum*.

The invention also provides a host cell comprising a nucleic acid or a vector according to the invention. An example of said host cell is provided in the detailed description herein. In a particular embodiment, said host cell comprises a plant cell. As a plant cell a cell derived from a member of the Solanaceae family is preferred, in particular wherein said member comprises *S. tuberosum* or *Lycopersicon esculentum*. From such a cell, or protoplast, a transgenic plant, such as transgenic potato plant or tomato plant with resistance against an oomycete infection can arise. The invention thus also provides a plant, or tuber root, fruit or seed or part or progeny derived thereof comprising a cell according to the invention.

Furthermore, the invention provides a proteinaceous substance, exhibiting the characteristic of providing at least partial resistance to an oomycete infection such as caused by *P. infestans* when incorporated and expressed in a plant or plant cell. In particular such a proteinaceous substance is provided that is encoded by a nucleic acid according to the invention. In a preferred embodiment, the invention provides a proteinaceous substance comprising an amino acid sequence as depicted in FIG. 8 or a functional equivalent thereof. Preferably, such a functional equivalent will comprise one or more sequences which are relatively unique to Rp1-blb in comparison to RGC3-blb, RGC-blb and RGC4-blb. Such sequences can be spotted in the alignment (see FIG. 10A) and would be the sequences RPLLGEM (SEQ ID NO:3), AKMEKEKLIS (SEQ ID NO: 4), KHSYTHMM (SEQ ID NO: 5), FFYTLPPLEKFI (SEQ ID No: 6), GDSTFNK (SEQ ID NO: 7), NLYGSGMRS (SEQ ID NO: 8), LQYCTKLC (SEQ ID NO: 9), GSQSLTCM (SEQ ID NO: 10), NNFGPHI (SEQ ID NO: 11), TSLKIYGFRGIH (SEQ ID NO: 12), IIHECPFLTLS (SEQ ID NO: 13), RICYNKVA (SEQ ID NO: 14), and KYLTISRCN (SEQ ID NO: 15). It is believed that one or more of these sequences provide the functional characteristics of the protein Rp1-blb.

Furthermore, the invention provides a binding molecule directed at a nucleic acid according to the invention. For example, the Rpi-blb gene can be used for the design of oligonucleotides complementary to one strand of the DNA sequence as depicted in FIG. 7 and Table 2. Such oligonucleotides as provided herein are useful as probes for library screening, hybridisation probes for Southern/Northern analysis, primers for PCR, for use in a diagnostic kit for the detection of disease resistance and so on. Such oligonucleotides are useful fragments of an isolated or recombinant nucleic acid as provided herein, said nucleic acid encoding a gene product that is capable of providing a member of the Solanaceae family with resistance against an oomycete fungus, or a functionally equivalent isolated or recombinant nucleic acid, in particular wherein said member comprises *S. tuberosum* or *Lycopersicon esculentum*. They can be easily selected from a sequence as depicted in FIG. 6 or part thereof. A particular point of recognition comprises the LRR domain as identified herein. Such a binding molecule according to the invention is used as a probe or primer, for example provided with a label, in particular wherein said label comprises an excitable moiety which makes it useful to detect the presence of said binding molecule.

The invention furthermore provides a method for selecting a plant or plant material or progeny thereof for its susceptibility or resistance to an oomycete infection comprising testing at least part of said plant or plant material or progeny thereof for the presence or absence of a nucleic acid, said nucleic acid encoding a gene product that is capable of providing a member of the Solanaceae family with resistance against an oomycete fungus, or for the presence of said gene product, said method preferably comprising contacting at least part of said plant or plant material or progeny thereof with a binding molecule according the invention and determining the binding of said molecule to said part. Said method is particularly useful wherein said oomycete comprises *P. infestans*, allowing to select plants or planting material for resistance against late blight, for example wherein said plant or material comprises *S. tuberosum*. It is believed that by the phylogenetic tree analysis as discussed above, proteins that are highly homologous to Rpi-blb and which would yield resistance against plant pathogens could be easily idientified. An example for this is the detection of the three highly homologous proteins RGC1-blb, RGC3-blb and RGC4-blb, which have not yet been shown to yield resistance to *P.*

*infestans*, but which are nevertheless believed to be involved in pathogen resistance in plants.

Also, the invention provides use of a nucleic acid or a vector or a cell or a substance or a binding molecule according to the invention in a method for providing a plant or its progeny with at least partial resistance against an oomycete infection, in particular wherein said oomycete comprises *P. infestans* especially wherein said plant comprises *S. tuberosum*, said method for providing a plant or its progeny with at least partial resistance against an oomycete infection comprising providing said plant or part thereof with a gene coding for a resistance protein or functional fragment thereof comprising a nucleic acid, said resistance protein being capable of providing a member of the Solanaceae family with resistance against an oomycete fungus, or providing said plant or part thereof with a nucleic acid or a vector or a cell or a substance according to the invention.

Furthermore, the invention provides an isolated *S. bulbocastanum*, or part thereof, such as a tuber or seed, susceptible to an oomycete infection caused by *P. infestans*.

The invention is further described in the detailed description below.

DESCRIPTION OF THE FIGURES

FIG. 6. Nucleic acid sequences of the Rpi-blb gene cluster members. A. Coding nucleic acid sequence of the Rpi-blb gene (SEQ ID NO: 48). B. Coding nucleic acid sequence of the Rpi-blb gene including the intron sequence (position 428–1106) (SEQ ID NO: 49). C. Sequence of the 5.2 kb ScaI genomic DNA fragment of *S. bulbocastanum* BAC SPB4 (SEQ ID NO: 50) present in pRGC2-blb, the genetic construct used for genetic complementation for late blight resistance. The genomic fragment harbours the Rpi-blb gene including natural regulatory elements necessary for correct expression of the gene. The initiation codon (ATG position 1191–1193) and the termination codon (TAA position 4781–4783) are underlined. D. Coding nucleic acid sequence of RGC3-blb including the intron sequence (position 428–708) (SEQ ID NO: 51). E. Coding nucleic acid sequence of RGC3-blb including the intron sequence (position 428–1458) (SEQ ID NO: 52). F. Coding nucleic acid sequence of RGC4-blb including intron sequences (positions 434–510, 543–618 and 743–1365) (SEQ ID NO: 53).

FIG. 8. Deduced Rpi-blb protein sequence (SEQ ID NO: 54). The amino acid sequence deduced from the DNA sequence of Rpi-blb is divided into three domains (A–C), as described in Example 6. Hydrophobic residues in domain A that form the first and fourth residues of heptad repeats of potential coiled-coil domains are underlined. Conserved motifs in R proteins are written in lowercase and in italic in domain B. Residues matching the consensus of the cytoplasmic LRR are indicated in bold in domain C. Dots in the sequence have been introduced to align the sequence to the consensus LRR sequence of cytoplasmic LRRs.

FIG. 10. Alignment of the predicted Rpi-blb gene product to the predicted protein sequences of Rpi-blb homologues A. Alignment of the deduced protein products encoded by Rpi-blb (SEQ ID NO: 54), RGC1-blb (SEQ ID NO: 55) RGC3-blb (SEQ ID NO: 56) and RGC4-blb (SEQ ID NO: 57). The complete amino acid sequence of Rpi-blb is shown and amino acid residues from RGC1-blb, RGC3-blb and RGC4-blb that differ from the corresponding residue in Rpi-blb. Dashes indicate gaps inserted to maintain optimal alignment. Amino acid residues that are specific for Rpi-blb, when compared to those at corresponding positions in RGC1-blb, RGC3-blb and RGC4-blb, are highlighted in bold. The regions of the LRRs that correspond to the consensus L..L..L.L..C/N/S..α..αP are underlined. Conserved motifs in the NBS domain are indicated in lowercase. B. Alignment of the deduced protein products encoded by Rpi-blb (SEQ ID NO: 54) RGC1-blb (SEQ ID NO: 55), RGC3-blb (SEQ ID NO: 56), RGC4-blb (SEQ ID NO: 57), B149-blb (SEQ ID NO: 61), SH10-tub (SEQ ID NO: 59), SH20-tub (SEQ ID NO: 62) and T118-ta (SEQ ID NO: 63).

EXPERIMENTAL PART

Figure 1:
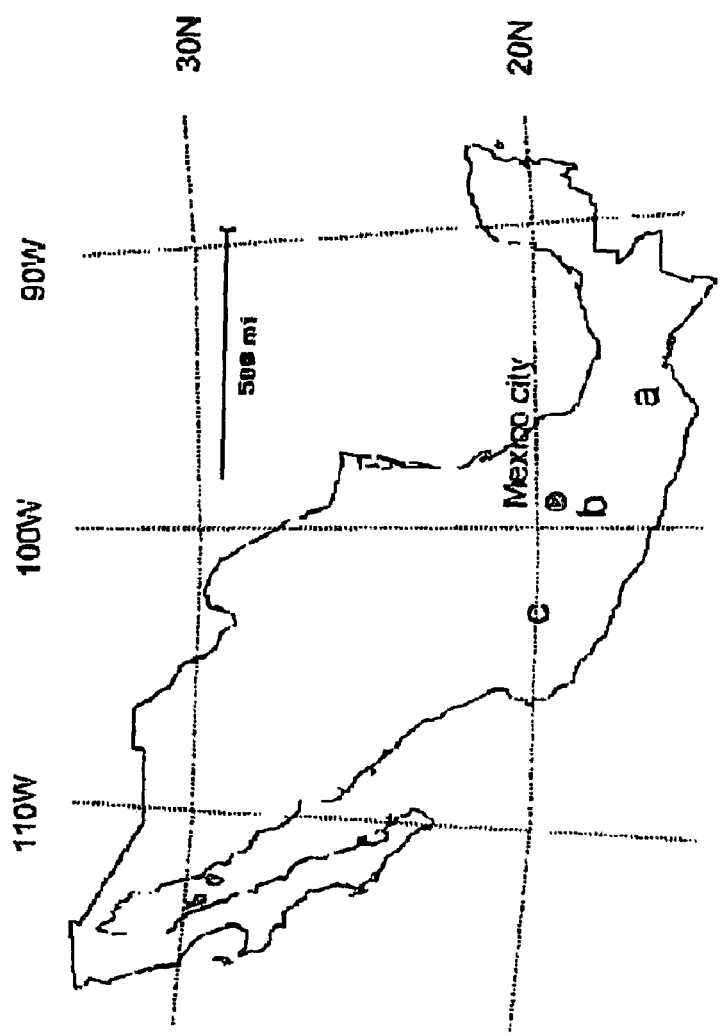
FIG. 1. Geographical map of Mexico indicating the origin of *Solanum bulbocastanum* accessions used to isolate the Rpi-blb gene. The letters a, b and c indicate the relative geographical origins of the used *S. bulbocastanum* accessions.

For the mapping of the Rpi-blb resistance gene an intraspecific mapping population of *S. bulbocastanum* was developed. A crucial step in this process was the identification of susceptible *S. bulbocastanum* genotypes. For this purpose several *S. bulbocastanum* accessions originating from different clusters/areas in Mexico were analysed for *P. infestans* resistance or susceptibility in a detached leaf assay (Table 1 and FIG. 1). The screened accessions BGRC 8008 and BGRC 7999 contained no susceptible genotypes. However in the accessions BGRC 8005, BGRC 8006 and BGRC 7997, susceptibility was found in 9%, 7% and 14% of the analysed seedlings, respectively. A *P. infestans* susceptible clone of accession BGRC 8006 was subsequently selected and crossed with a resistant clone of accession BGRC 8005. The resulting F1 population was used to map the Rpi-blb locus and is hereafter referred to as the B8 population.

Figure 2:
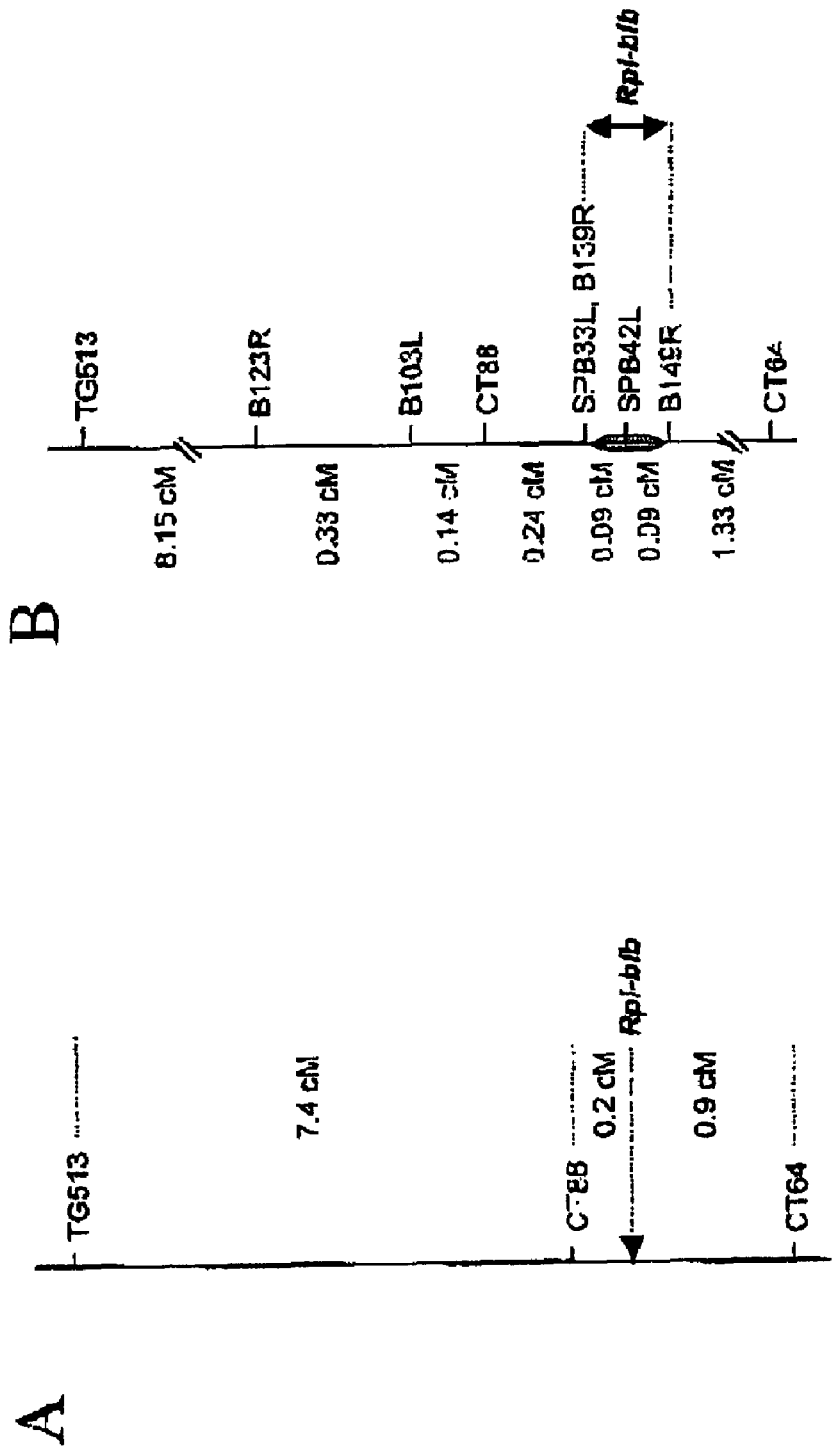
FIG. 2. Genetic linkage maps of the Rpi-blb locus on chromosome 8 of *S. bulbocastanum*. Horizontal lines indicate the relative positions of markers linked to late blight resistance. Distances between markers are indicated in centimorgans. A. Genetic position of the Rpi-blb locus relative to markers TG513, CT88 and CT64 (n=508 genotypes). B. High density genetic linkage map of the Rpi-blb locus (n=2109 genotypes).

Initial screening of 42 B8 genotypes for resistance to *P. infestans* in a detached leaf assay suggested that *P. infestans* resistance in *S. bulbocastanum* accession 8005 could be caused by a single dominant R gene, or a tightly linked gene cluster. Of the 42 genotypes tested, 22 scored resistant and 16 susceptible in a repeated experiment. Resistance phenotypes of the remaining 4 seedlings remained unclear. In order to determine the chromosome position of this *S. bulbocastanum* resistance, B8 genotypes with an undoubted phenotype were used for marker analysis. The chromosome 8 specific marker TG330 (Table 2) was found to be linked in repulsion phase with the resistant phenotype, as only one recombinant was obtained between this marker and resistance in 12 B8 genotypes. Furthermore, chromosome 8 marker CT88 (Table 2) was found to be completely linked in repulsion phase to resistance, indicating that the locus responsible for resistance, designated Rpi-blb, was located in this region of chromosome 8. For this reason, tomato chromosome 8 specific markers that map proximal and distal to CT88 (TG513 and CT64; Tanksley et al., 1992 Genetics 132: 1141–1160; Table 2) were developed into CAPS markers and tested in 512 B8 genotypes with known resistance phenotypes. A total of five CT64–CT88 recombinant genotypes and 41 CT88–TG513 recombinant genotypes were identified in this screen (FIG. 2A). The resistance locus Rpi-blb was mapped 1 recombination event distal to marker CT88 (FIG. 2A).

Figure 3:
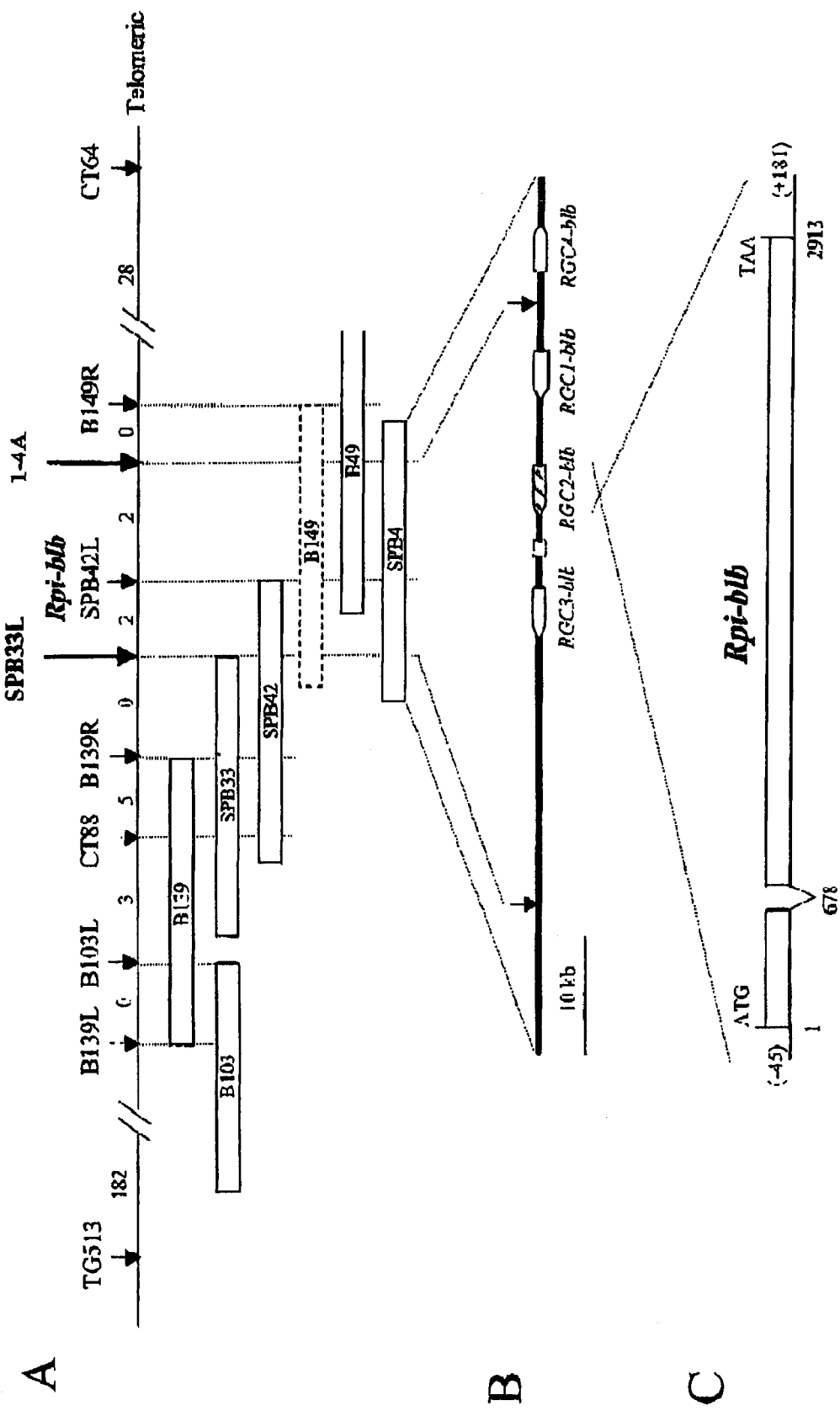
FIG. 3. Physical map of the Rpi-blb locus. A. Genetic and physical map of the *S. bulbocastanum* genomic region containing Rpi-blb. Vertical arrows indicate the relative positions of markers linked to resistance. Numbers above the horizontal line indicate the number of recombinants identified between the flanking markers in 2109 progeny plants. Rectangles represent bacterial artificial chromosome (BAC) clones. B. Relative positions of candidate genes for late blight resistance on BAC SPB4. C. Schematic representation of the Rpi-blb gene structure. Horizontal lines indicate exons. Open boxes represent coding sequence. Lines angled downwards indicate the position of a 678-nucleotide long intron sequence.
Figure 4:
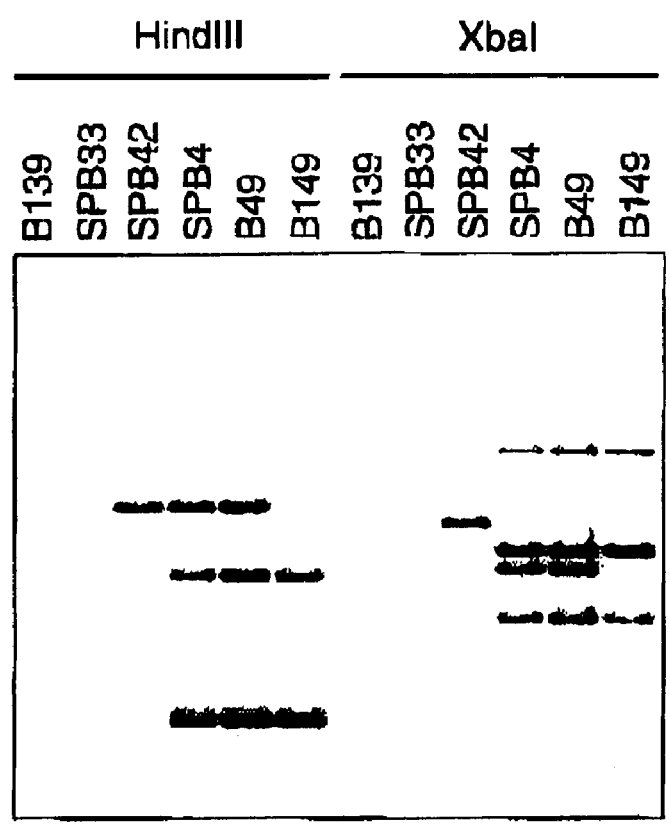
FIG. 4. Southern blot analysis of the BAC contig spanning the Rpi-blb locus. Names above each lane represent the names of BAC clones. The names of the restriction enzymes used to digest the BAC DNA prior to Southern blotting are indicated.

Fine mapping of the Rpi-blb locus was carried out with CAPS markers derived from left (L) and right (R) border sequences of BAC clones isolated from a BAC library prepared from the resistant *S. bulbocastanum* genotype BGRC 8005-8. The BAC library was initially screened with markers CT88 and CT64. BAC clones identified with these markers were used as seed BACs for a subsequent chromosome walk to the Rpi-blb locus. A total of 2109 B8 genotypes were screened for recombination between markers TG513 en CT64. All recombinant genotypes (219/2109) were subsequently screened with all available markers in the CT88–CT64 genetic interval. These data together with the disease resistance data of each recombinant, obtained through detached leaf assays, positioned the Rpi-blb locus between markers SPB33L and B149R, a 0.1 cM genetic interval (4/2109 recombinants) physically spanned by the overlapping BAC clones SPB4 and B49 (FIGS. 2b and 3). Within this interval resistance cosegregated with the BAC end marker SPB42L, the sequence of which was highly homologous to partial NBS fragments from tomato (e.g. Q194, Q137, Q152, Q153; Pan et al., 2000 Genetics 155: 309–322). Southern analyses of BAC clones spanning the SP33L–B149R interval using a $^{32}$P-labeled PCR fragment of marker SPB42L as a probe revealed the presence of at least 4 copies of this R gene like sequence within the Rpi-blb interval (FIG. 4). Moreover, all of these copies were present on BAC SPB4. Sequencing and annotation of the complete insert of this BAC clone indeed identified four complete R gene candidates (RGC1-blb, RGC2-blb, RGC3-blb and RGC4-blb) of the NBS-LRR class of plant R genes. A PCR-marker that was located in-between RGC1-blb and RGC4-blb revealed recombination between *P. infestans* resistance and RGC4-blb, ruling out the possibility of RGC4-blb being Rpi-blb. Despite this finding, all four RGCs were selected for complementation analysis.

Figure 5:
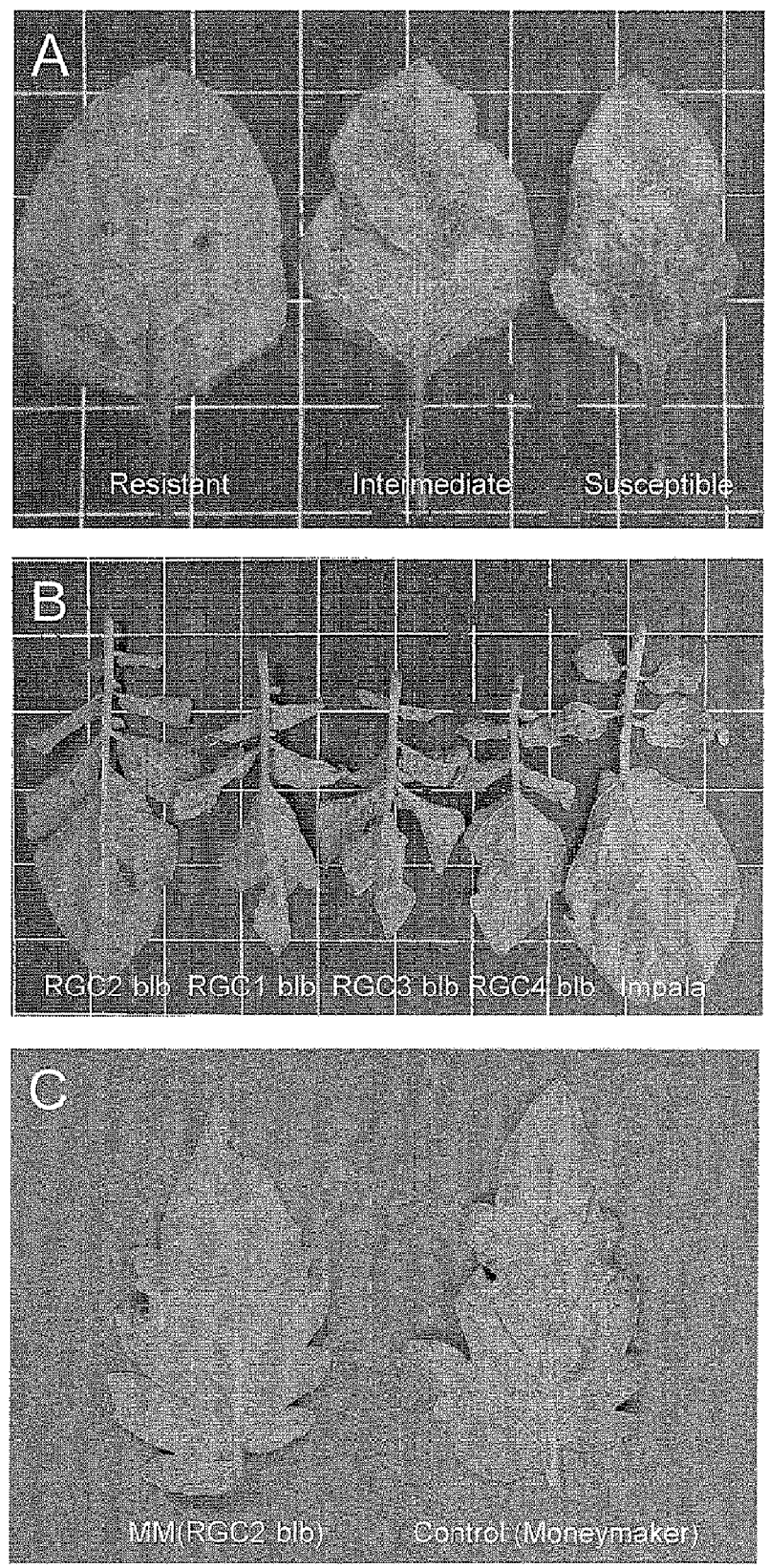
FIG. 5. Detached leaf disease assays. A. Resistant (left), intermediate (centre) and susceptible (right) phenotypes found in the *S. bulbocastanum* mapping population B8 6 days post inoculation (d.p.i) with *P. infestans* sporangiospore droplets. B. Genetic complementation for late blight resistance in potato. Characteristic disease phenotypes of leaves derived from transgenic potato plants harbouring RGC1-blb, RGC2-blb, -blb or RGC4-blb 6 d.p.i. with *P. infestans* sporangiospore droplets. Genetic constructs harbouring the RGCs were transferred to the susceptible potato cultivar Impala through Agrobacterium mediated transformation. C. Genetic complementation for late blight resistance in tomato. Characteristic disease phenotype of a tomato leaf derived from transgenic tomat plants harbouring Rpi-blb 6 d.p.i. with *P. infestans* sporangiospore droplets (left panel). The genetic construct harbouring Rpi-blb was transferred to the susceptible tomato cultivar Moneymaker through Agrobacterium mediated transformation.

Genomic fragments of approximately 10 kb harbouring RGC1-blb, RGC2-blb, RGC3-blb or RGC4-blb were subcloned from BAC SPB4 into the binary plant transformation vector pBINPLUS (van Engelen et al., 1995 Trans. Res. 4, 288–290) and transferred to a susceptible potato cultivar using standard transformation methods. Primary transformants were tested for *P. infestans* resistance as described in Example 1. Only the genetic construct harbouring RGC2-blb was able to complement the susceptible phenotype; 86% of the primary transformants harbouring RGC2-blb were resistant (Table 3) whereas all RGC1-blb, RGC3-blb and RGC4-blb containing primary transformants were completely susceptible to *P. infestans*. The resistant RGC2-blb containing transformants showed similar resistance phenotypes as the *S. bulbocastanum* resistant parent (FIG. 5). RGC2-blb was therefore designated the Rpi-blb gene, the DNA sequence of which is provided in FIG. 6.

EXAMPLE 1

Disease Assay

The phenotype of *S. bulbocastanum* and transgenic *S. tuberosum* genotypes for resistance to *P. infestans* was determined by detached leaf assays. Leaves from plants grown for 6 to 12 weeks in the greenhouse were placed in pieces of water-saturated florists foam, approximately 35×4×4 cm, and put in a tray (40 cm width, 60 cm length and 6 cm height) with a perforated bottom. Each leaf was inoculated with two droplets or more (25 μl each) of sporangiospore solution on the abaxial side. Subsequently, the tray was placed in a plastic bag on top of a tray, in which a water-saturated filter paper was placed, and incubated in a climate room at 17° C. and a 16 h/8 h day/night photoperiod with fluorescent light (Philips TLD50W/84HF). After 6 days, the leaves were evaluated for the development of P. infestans disease symptoms. Plants with leaves that clearly showed sporulating lesions 6 days after inoculation were considered to have a susceptible phenotype whereas plants with leaves showing no visible symptoms or necrosis at the side of inoculation in the absence of clear sporulation were considered to be resistant. The assay was performed with P. infestans complex isolate 655-2A (race 1, 2, 3, 4, 5, 6, 7, 8, 9, 10, 11), which was obtained from Plant Research International BV (Wageningen, The Netherlands).

EXAMPLE 2

Mapping of the Rpi-blb Resistance Locus

Plant Material

In order to produce an intraspecific mapping population that segregated for the P. infestans resistance gene present in S. bulbocastanum accession BGRC 8005 (CGN 17692, PI 275193), a susceptible S. bulbocastanum genotype was required. Several S. bulbocastanum accessions originating from different clusters/areas in Mexico were analysed for P. infestans resistance or susceptibility in a detached leaf assay (Table 1 and FIG. 1). In accession BGRC 8008 and BGRC 7999 no susceptibility was detected. In accession BGRC 8005, BGRC 8006 and BGRC 7997 susceptibility was only present in 9%, 7% and 14% of the analysed seedlings, respectively. Thus, only a few susceptible S. bulbocastanum genotypes were obtained.

The intraspecific mapping population of S. bulbocastanum (B8) was produced by crossing a P. infestans susceptible clone of accession BGRC 8006 with a resistant clone of accession BGRC 8005. DNA of 2109 progeny plants was extracted from young leaves according to Doyle and Doyle (1989 Focus 12, 13–15).

CAPS Marker Analysis

For PCR analysis, 15 μl reaction mixtures were prepared containing 0.5 μg DNA, 15 ng of each primer, 0.2 mM of each dNTP, 0.6 units Taq-polymerase (15 U/μl, SphaeroQ, Leiden, The Netherlands), 10 mM Tris-HCl pH 9, 1.5 mM $MgCl_2$, 50 mM KCl, 0.1% Triton X-100 and 0.01% (w/v) gelatin. The PCRs were performed using the following cycle profile: 25 seconds DNA denaturation at 94° C., 30 seconds annealing (see Table 1) and 40 seconds elongation at 72° C. As a first step in PCR-amplification DNA was denatured for 5 min at 94° C. and finalised by an extra 5 min elongation step at 72° C. The amplification reactions were performed in a Biometra® T-Gradient or Biometra® Uno-II thermocycler (Westburg, Leusden, The Netherlands). Depending on the marker, the PCR product was digested with an appropriate restriction enzyme. An overview of the markers including primer sequences, annealing temperature and restriction enzymes, is given in Table 2. Subsequently, the (digested) PCR products were analysed by electrophoresis in agarose or acrylamide gels. For acrylamide gel analysis, the CleanGel DNA Analysis Kit and DNA Silver Staining Kit (Amersham Pharmacia Biotech Benelux, Roosendaal, the Netherlands) were used.

Genetic Mapping of the Rpi-blb Locus

Initially a small group of 42 progeny plants of the B8 population was screened for resistance to P. infestans in a detached leaf assay. Plants with leaves that clearly showed sporulating lesions 6 days after inoculation were considered to have a susceptible phenotype whereas plants with leaves showing no visible symptoms or necrosis at the side of inoculation in the absence of clear sporulation were considered to be resistant. Of the 42 seedlings, 22 scored resistant and 16 susceptible. The phenotype of the remaining 4 seedlings remained unclear in this initial phase. These data indicated that resistance could be due to a single dominant gene or a tightly linked gene cluster. In order to determine the chromosome position, seedlings with a reliable phenotype were used for marker analysis. Chromosome 8 marker TG330 was found to be linked in repulsion with the resistant phenotype, as only one recombinant was obtained between this marker and resistance in 12 B8 seedlings. Furthermore, chromosome 8 marker CT88 was found to be completely linked in repulsion phase to resistance, indicating that a resistance gene was located on chromosome 8.

Subsequently, chromosome 8 specific markers that had been mapped proximal and distal to CT88 (Tanksley et al., 1992 Genetics 132: 1141–1160) were developed to CAPS markers. In order to map these markers more precisely, another 512 individuals of the B8 population were screened for late blight resistance using the detached leaf disease assay. Simultaneously, plants were scored for the markers CT64, CT88 and TG513. For 5 seedlings, recombination was detected between markers CT64 and CT88, while 41 seedlings were recombinant between markers CT88 and TG513 (FIG. 2A). The resistance gene Rpi-blb was mapped in between markers CT64 and CT88. In this stage, the positioning of CT88 proximal to Rpi-blb was based on only one recombined seedling.

In order to determine the position of Rpi-blb more precisely relative to the available markers, another 1555 seedlings of the B8 population were grown and analysed for recombination between the markers TG513 and CT64. Thus, a total of 2109 individual offspring clones of the B8 population were screened. Recombination between markers TG513 en CT64 was detected in 219 of these seedlings (10.4 cM). All of the recombinants were screened with marker CT88 and phenotyped for the resistance trait by making use of the detached leaf assay. In agreement with earlier results, the Rpi-blb gene was mapped in between markers CT88 and CT64 (FIG. 2B).

EXAMPLE 3

Construction of a S. bulbocastanum BAC Library and Construction of a Contiguous BAC Contig Spanning the Rpi-blb Locus BAC Library Construction A resistant clone of S. bulbocastanum (blb) accession BGRC 8005 (CGN 17692, PI 275193) heterozygous for the Rpi-blb locus, was used as source DNA for the construction of a genomic BAC library, hereafter referred to as the 8005-8 BAC library. High molecular weight DNA preparation and BAC library construction were carried out as described in Rouppe van der Voort et al. (1999 MPMI 12:197–206). Approximately 130.000 clones with an average insert size of 100 kb, which corresponds to 15 genome equivalents were finally obtained. A total of approximately 83.000 individual clones were stored in 216 384-well microtiter plates (Invitrogen, The Netherlands) containing LB freezing buffer (36 mM $K_2HPO_4$, 13.2 mM $KH_2PO_4$, 1.7 mM citrate, 0.4 mM $MgSO_4$, 6.8 mM $(NH_4)_2SO_4$, 4.4% V/V glycerol, 12.5 pg/ml chloramphenicol in LB medium) at −80° C. Another 50.000 clones were stored as bacterial pools containing ~1000 white colonies. These were generated by scraping the colonies from the agar plates into LB medium containing 18% glycerol and 12.5 µg/ml chloramphenicol using a sterile glass spreader. These so-called super pools were also stored at −80° C.

Screening of the BAC Library and Construction of a Physical Map of the Rpi-blb Locus The 8005-8 BAC library was initially screened with CAPS markers CT88 and CT64. This was carried out as follows. For the first part of the library of approximately 83.000 clones stored in 384 well microtiter plates, plasmid DNA was isolated using the standard alkaline lysis protocol (Sambrook et al., 1989 in Molecular cloning: a laboratory manual $2^{nd}$ edn, Cold Spring Harbor Press, Cold Spring Harbor, N.Y.) from pooled bacteria of each plate to produce 216 plate pools. To identify individual BAC clones carrying the CAPS markers the plate pools were screened by PCR. Once an individual plate pool was identified as being positive for a particular CAPS marker the positive row and positive column were identified through a two dimensional PCR screening. For this purpose, the mother 384-well plate was replicated twice on LB medium containing chloramphenicol (12.5 µg/ml). After growing the colonies for 16 h at 37° C. one plate was used to scrape the 24 colonies of each row together and the other plate was used to scrape the 16 colonies of each column together. Bacteria of each row or column were resuspended in 200 µl TE buffer. CAPS marker analysis on 5 µl of these bacterial suspensions was subsequently carried out leading to the identification of single positive BAC clones. For the second part of the library, stored as 50 pools of approximately 1000 clones, plasmid DNA was isolated from each pool of clones using the standard alkaline lysis protocol and PCR was carried out to identify positive pools. Bacteria corresponding to positive pools were diluted and plated on LB agar plates containing chloramphenicol (12.5 µg/ml). Individual white colonies were subsequently picked into 384-well microtiter plates and single positive BAC clones subsequently identified as described above. Names of BAC clones isolated from the super pools carry the prefix SP (e.g. SPB33).

Insert sizes of BAC clones were estimated as follows. Positive BAC clones were analysed by isolating plasmid DNA from 2 ml overnight cultures (LB medium supplemented with 12.5 mg/ml chloramphenicol) using the standard alkaline lysis miniprep protocol and resuspended in 20 µl TE. Plasmid DNA (10 µl) was digested with 5 U NotI for 3 h at 37° C. to free the genomic DNA from the pBeloBAC11 vector. The digested DNA was separated by CHEF electrophoresis in a 1% agarose gel in 0.5×TBE at 4° C. using a BIORAD CHEF DR II system (Bio-Rad Laboratories, USA) at 150 volts with a constant pulse time of 14 sec for 16 h.

Screening of the 8005-8 BAC library with marker CT88 identified two positive BAC clones: B139 and B180, with potato DNA inserts of 130 and 120 kb, respectively (FIG. 3A). Digestion of the CT88 PCR product generated from these BAC clones and several resistant and susceptible progeny plants of the B8 mapping population with MboI revealed that BAC 139 carried the CT88 allele that was linked in cis to resistance. To identify the relative genome position of BAC B139, pairs of PCR primers were designed based on the sequence of the right (R) and left (L) ends of the insert. BAC end sequencing was carried out as described in Example 4 using 0.5 µg of BAC DNA as template. Polymorphic CAPS markers were developed by digesting the PCR products of the two parent genotypes of the B8 population and of two resistant and two susceptible progeny genotypes with several 4-base cutting restriction enzymes (Table 2). Screening of the 37 CT88–CT64 recombinant B8 genotypes mapped 5 of the 7 CT88–Rpi-blb recombinants between CT88 and B139R, indicating that marker B139R was relatively closer to the Rpi-blb locus than marker CT88. Screening of the 216 plate pools with B139R did not lead to the identification of a positive BAC clone. Screening of the 50 super pools identified the positive BAC clones SPB33 and SPB42 with DNA inserts of 85 and 75 kb, respectively (FIG. 3A). Screening of the complete BAC library with SPB33L identified the positive BAC clones B149 and SPB4. BAC clone SPB4 contained the SPB33L allele that was linked in cis to resistance whereas BAC clone B149 did not. However, screening of the CT88–CT64 recombinant panel with B149R revealed that this BAC spanned the Rpi-blb locus. B149R was separated from the Rpi-blb locus by two recombination events (FIG. 3A). Screening of the 8005-8 BAC library with B149R identified BAC clone B49 as having the B149R allele that was linked in cis to resistance. This BAC clone together with BAC clone SPB4 therefore formed a BAC contig that spanned the Rpi-blb locus (FIG. 3).

EXAMPLE 4

Sequence Analysis of BAC SPB4 and Identification of Resistance Gene Candidates within the Rpi-blb Locus Within the SPB33L-B 149R interval resistance cosegregated with BAC end marker SPB42L, the sequence of which was highly homologous to partial NBS fragments from tomato (e.g. Q194, Q137, Q97, Q152, Q153; Pan et al., 2000 Genetics 155:309–22). Southern analyses of BAC clones spanning the SPB33L-B149R interval using a $^{32}$P-labeled PCR fragment of marker SPB42L as a probe revealed the presence of at least 4 copies of this R gene like sequence within the Rpi-blb interval (FIG. 4). Moreover, all of these copies were present on BAC SPB4. The DNA sequence of BAC clone SPB4 was therefore determined by shotgun sequence analysis. A set of random subclones with an average insert size of 1.5 kb was generated. 10 µg of CsCl purified DNA was sheared for 6 seconds on ice at 6 amplitude microns in 200 µl TE using an MSE soniprep 150 sonicator. After ethanol precipitation and resuspension in 20 µl TE the ends of the DNA fragments were repaired by T4 DNA polymerase incubation at 11° C. for 25 minutes in a 50 µl reaction mixture comprising 1×T4 DNA polymerase buffer (New England BioLabs, USA), 1 mM DTT, 100 µM of all 4 dNTP's and 25 U T4 DNA polymerase (New England Biolabs, USA), followed by incubation at 65° C. for 15 minutes. The sheared DNA was subsequently separated by electrophoresis on 1% SeaPlaque LMP agarose gel (FMC). The fraction with a size of 1.5–2.5 kb was excised from the gel and dialysed against 50 ml TE for 2 hr at 4° C. Dialysed agarose slices were then transferred to a 1.5 ml Eppendorf tube, melted at 70° C. for 5 min, digested with 1 unit of GELASE (Epicentre Technologies, USA) per 100 mg of agarose gel for 1 hr at 45° C., and the DNA was subsequently precipitated. The 1.5–2.5 kb fragments were ligated at 16° C. in a EcoRV restricted and dephosphorylated pBluescript SK$^+$ vector (Stratagene Inc.). The ligation mixture was subsequently used to transform ElectroMAX E. coli DH10B competent cells (Life Technologies, UK) by electroporation using the BioRad Gene Pulser.

Settings on the BioRad Gene Pulser were as recommended for *E. coli* by the manufacturer. The cells were spread on Luria broth (LB) agar plates containing ampicillin (100 μg/ml), 5-bromo-4-chloro-3-indolyl-β-D-galactoside (Xgal) (64 μg/ml) and isopropyl-1-thio-β-D-galactoside (IPTG) (32 μg/ml). Plates were incubated at 37° C. for 24 hours. Individual white colonies were grown in 96-well flat-bottom blocks (1.5 ml Terrific Broth medium containing 100 μg/ml ampicillin).

Plasmid DNA was isolated using the QIAprep 96 Turbo Miniprep system in conjunction with the BioRobot™ 9600 (QIAGEN) according to the manufacturers instructions. Sequencing reactions were performed using ABI PRISM BigDye™ Terminator cycle sequencing kit (Stratagene) according to the manufacturer's instructions. All clones were sequenced bi-directionally using universal primers. Sequence products were separated by capillary electrophoresis on a Perkin Elmer ABI 3700 DNA Analyzer.

The automated assembly of the shotgun reads was carried out using the Phred-Phrap programs (Ewing and Green, 1998 Genome Research 8, 186–194; Ewing et al., 1998 Genome Research 8, 175–185). A total of 835 reads provided an overall BAC sequence coverage equal to 5×. Gaps between contigs were closed by primer walking or through a combinatorial PCR approach. The sequence was finally edited at Phred quality 40 (1 error every 10,000 nt) by manual inspection of the assembly using the Gap4 contig editor and re-sequencing of all low-quality regions. The complete sequence of the insert of BAC SPB4 consisted of 77,283 nucleotides.

Analysis of the contiguous sequence of BAC SPB4 using the computer programme GENSCAN (Burge and Karlin, 1997 J. Mol. Biol. 268, 78–94), GENEMARK (Lukashin and Borodovsky, 1998 NAR 26, 1107–1115) and BLASTX (Altschul et al., 1990 J. Mol. Biol. 215, 403–410) identified four complete R gene candidate sequences (RGC1-blb, RGC2-blb, RGC3-blb and RGC4-blb) belonging to the NBS-LRR class of plant R genes. A CAPS marker designed in between RGC1-blb and RGC4-blb, marker RGC1–4 revealed recombination between *P. infestans* resistance and RGC4-blb, ruling out the possibility of RGC4-blb being Rpi-blb (FIG. 3A and B). Despite this finding, all four RGCs were selected for complementation analysis.

EXAMPLE 5

Complementation Analysis

Subcloning of Candidate Genes and Transformation to *Agrobacterium tumefaciens*

Genomic fragments of approximately 10 kb harbouring RGC1-blb, RGC2-blb, RGC3-blb or RGC4-blb were subcloned from BAC clone SPB4 into the binary plant transformation vector pBINPLUS (van Engelen et al., 1995 Trans. Res. 4, 288–290). Restriction enzyme digestion of BAC clone SPB4 DNA and subsequent size selection was carried out as follows. Aliquots of ~1 μg DNA were digested with 1U, 0.1U or 0.01U of Sau3AI restriction enzym for 30 min. The partially digested BAC DNA was subjected to CHEF electrophoresis at 4° C. in 0.5×TBE using a linear increasing pulse time of 1–10 sec and a field strength of 6 V/cm for 16 hr. After electrophoresis, the agarose gel was stained with ethidium bromide to locate the region of the gel containing DNA fragments of approximately 10 kb in size. This region was excised from the gel using a glass coverslip and dialysed against 50 ml TE for 2 hr at 4° C. Dialysed agarose slices were then transferred to a 1.5 ml Eppendorf tube, melted at 70° C. for 5 min and digested with 1 unit of GELASE (Epicentre Technologies, USA) per 100 mg of agarose gel for 1 hr at 45° C. Ligation of the size selected DNA to BamHI-digested and dephosphorylated pBINPLUS and subsequent transformation of ElectroMAX *E. coli* DH10B competent cells (Life Technologies, UK) with the ligated DNA was carried as described in Example 5, using the BioRad Gene Pulser for electroporation. The cells were spread on Luria broth (LB) agar plates containing kanamycin (50 μg/ml), Xgal (64 μg/ml) and IPTG (32 μg/ml). Plates were incubated at 37° C. for 24 hours. Individual white colonies were grown in 96-well plates (100 μl LB medium containing 50 μg/ml kanamycin). A total of 480 clones were PCR screened for the presence of RGCs using primers SPB42LF and SPB42LR or RGC4F and RGC4R (Table 2.). Positive clones were selected for plasmid isolation and further characterisation. Identification of clones harbouring RGC1-blb, RGC2-blb, RGC3-blb or RGC4-blb was carried out by sequencing the SPB42L PCR fragments derived from positive clones. The relative position of the RGCs within a subclone was determined by sequencing the ends of the clone and subsequent comparison of the sequences to the complete BAC insert sequence. Finally four binary plasmids, pRGC1-blb, pRGC2-blb, pRGC3-blb and pRGC4-blb were selected and transferred to *Agrobacterium tumefaciens* strains AGLO (Lazo et al., 1991 Bio/Technology 9, 963–967), LBA4404 (Hoekema et al., 1983 Nature 303: 179–180) or UIA143 (Farrand et al., 1989 J. of Bacteriology 171, 5314–5321) either by electroporation using the BioRad Gene Pulser or by conjugation. Settings on the BioRad Gene Pulser were as recommended for *A. tumefaciens* by the manufacturer. Conjugation was carried out as described by Simon et al. (1983 Bio/Tech. 1, 784–791). The cells were spread on Luria broth (LB) agar plates containing kanamycin (100 mg/l) and rifampicin (50 mg/l). Plates were incubated at 28° C. for 48 hours. Small-scale cultures from selected colonies were grown in LB medium containing kanamycin (100 mg/l) and rifampicin (50 mg/l). Plasmid DNA was isolated as described previously and the integrity of the plasmids was verified by restriction analysis upon reisolation from *A. tumefaciens* and subsequent transformation to *E. coli*. *A. tumefaciens* cultures harbouring a plasmid with the correct DNA pattern were used to transform a susceptible potato genotype.

Transformation of Susceptible Potato Cultivar

*A. tumefaciens* strains were grown for 2 days at 28° C. in 20 ml LB medium supplemented with 50 mg/l rifampicine and 25 mg/l kanamycin. Subsequently, 0.2 ml of *A. tumefaciens* culture was diluted in 10 ml LB medium containing the same antibiotics and grown overnight (28° C.). The overnight culture was centrifuged (30 min, 2647×g) and the pellet was resuspended in 50 ml MS medium (Murashige and Skoog, 1962 Physiol. Plant. 15, 473–497) supplemented with 30 g/l sucrose (MS30).

Certified seed potatoes of cultivar Impala were peeled and surface sterilised for 30 min. in a 1% sodium hypochlorate solution containing 0.1% Tween-20. Tubers were then washed thoroughly in large volumes of sterile distilled water (4 times, 10 min). Discs of approximately 2 mm thickness and 7 mm in diameter, were sliced from cylinders of tuber tissue prepared with a corkborer. The tuber discs were transferred into liquid MS30 medium containing *A. tumefaciens* and incubated for 15 min. After removing the *A. tumefaciens* solution, the tuber discs were transferred to regeneration medium containing MS30, 0.9 mg/l IAA, 3.6 mg/l zeatine riboside and 8 g/l agar (Hoekema et al., 1989 Bio/Technology 7, 273–278). The plates were incubated at 24° C., 16 hour day-length (Philips TLD50W/84HF). After 48 hours of co-cultivation, the tuber discs were rinsed for 5 min in liquid MS medium including antibiotics, 200 mg/l vancomycin, 250 mg/l cefotaxim and 75 mg/l kanamycin, and transferred to regeneration medium supplemented with the same antibiotics. The plates were incubated at 24° C., 16 hour day-length (Philips TLD50W/84HF). Every three weeks, the tuber discs were transferred to fresh medium. Regenerating shoots were transferred to MS30 medium containing 75 mg/l kanamycin. Rooting shoots were propagated in vitro and tested for absence of *A. tumefaciens* cells by incubating a piece of stem in 3 ml LB medium (3 weeks, 37° C., 400 rpm). One plant of each transformed regenerant was transferred to the greenhouse.

Complementation of the Susceptible Phenotype in Potato

Primary transformants were tested for *P. infestans* resistance as described in Example 1. Only the genetic construct harbouring RGC2-blb was able to complement the susceptible phenotype; 15 out of 18 RGC2-blb containing primary transformants were resistant (Table 3) whereas all RGC1-blb, RGC3-blb and RGC4-blb containing primary transformants were completely susceptible to *P. infestans*. The resistant RGC2-blb transformants showed similar resistance phenotypes as the *S. bulbocastanum* resistant parent (FIG. 5). RGC2-blb was therefore designated the Rpi-blb gene, the DNA sequence of which is provided in FIG. 6.

Transformation of Susceptible Tomato

Seeds of the susceptible tomato line Moneymaker were rinsed in 70% ethanol to dissolve the seed coat and washed with sterile water. Subsequently, the seeds were surface-sterilised in 1.5% sodium hypochlorite for 15 minutes, rinsed three times in sterile water and placed in containers containing 140 ml MS medium pH 6.0 (Murashige and Skoog, 1962 Physiol. Plant. 15, 473–497) supplemented with 10 g/l sucrose (MS10) and 160 ml vermiculite. The seeds were left to germinate for 8 days at 25° C. and 0.5 W/M2 light. Eight day old cotyledon explants were pre-cultured for 24 hours in Petri dishes containing a two week old feeder layer of tobacco suspension cells plated on co-cultivation medium (MS30 pH 5.8 supplemented with Nitsch vitamines (Duchefa Biochemie BV, Haarlem, The Netherlands), 0.5 g/l MES buffer and 8 g/l Daichin agar).

Overnight cultures of *A. tumefaciens* were centrifuged and the pellet was resuspended in cell suspension medium (MS30 pH 5.8 supplemented with Nitsch vitamines, 0.5 g/l MES buffer, pH 5.8) containing 200 µM acetosyringone to a final O.D.$_{600}$ of 0.25. The explants were then infected with the diluted overnight culture of *A. tumefaciens* strain UIA143 (Farrand et al., 1989 J. of Bacteriology 171, 5314–5321) containing the helper plasmid pCH32 (Hamilton et al., 1996 PNAS 93, 9975–9979) and pRGC2-blb for 25 minutes, blotted dry on sterile filter paper and co-cultured for 48 hours on the original feeder layer plates. Culture conditions were as described above.

Following the co-cultivation, the cotyledons explants were transferred to Petri dishes with selective shoot inducing medium (MS pH 5.8 supplemented with 10 g/l glucose, including Nitsch vitamines, 0.5 g/l MES buffer, 5 g/l agargel, 2 mg/l zeatine riboside, 400 mg/l carbenicilline, 100 mg/l kanamycine, 0.1 mg/l IAA) and cultured at 25° C. with 3–5 W/m² light. The explants were sub-cultured every 3 weeks onto fresh medium. Emerging shoots were dissected from the underlying callus and transferred to containers with selective root inducing medium (MS10 pH 5.8 supplemented with Nitsch vitamines, 0.5 g/l MES buffer, 5 g/l agargel, 0.25 mg/l IBA, 200 mg/l carbenicillin and 100 mg/l kanamycine).

Complementation of the Susceptible Phenotype in Tomato

To investigate whether Rpi-blb could complement the susceptible phenotype in tomato, primary transformants of Moneymaker harbouring the Rpi-blb gene construct were initially challenged with the potato derived *P. infestans* isolates IP0655-2A and IP0428. Seven out of nine primary transformants were resistant (Table 3). In view of the observation that the tested potato *P. infestans* isolates were less virulent on tomato than on potato, the primary transformants were also tested with a *P. infestans* isolate collected from susceptible home garden tomato plants. Even though this isolate was significantly more virulent on Moneymaker than the previously tested ones, all 7 primary transformants remained resistant. These results illustrate the potential effectiveness of the Rpi-blb gene not only against complex isolates derived from potato but also to those specialised on tomato.

Molecular Analysis of Primary Transformants

RT-PCR Analysis

In order to produce cDNA, a mix of 19 µl containing 1 µg of total or polyA RNA, 0.25 mM of each dNTP, 50 mM Tris-HCl pH 8.3, 75 mM KCl, 3 mM MgCl$_2$, 10 mM DTT and 530 ng oligo d(t) primer, GCTGTCAACGATACGCTACG-TAACGGCATGACAGTG(T)$_{18}$ (SEQ ID NO: 16) was denatured (1 min 83° C.). Subsequently, the mix was placed at 42° C. and 1 µl reverse transcriptase (M-MLV reverse transcriptase, Promega Benelux b.v., Leiden, The Netherlands) was added. After 60 min, the mix was heated for 1 min at 99° C. and transferred to ice. 2 µl cDNA was used for standard PCR.

Rapid Amplification of cDNA Ends

Figure 7:
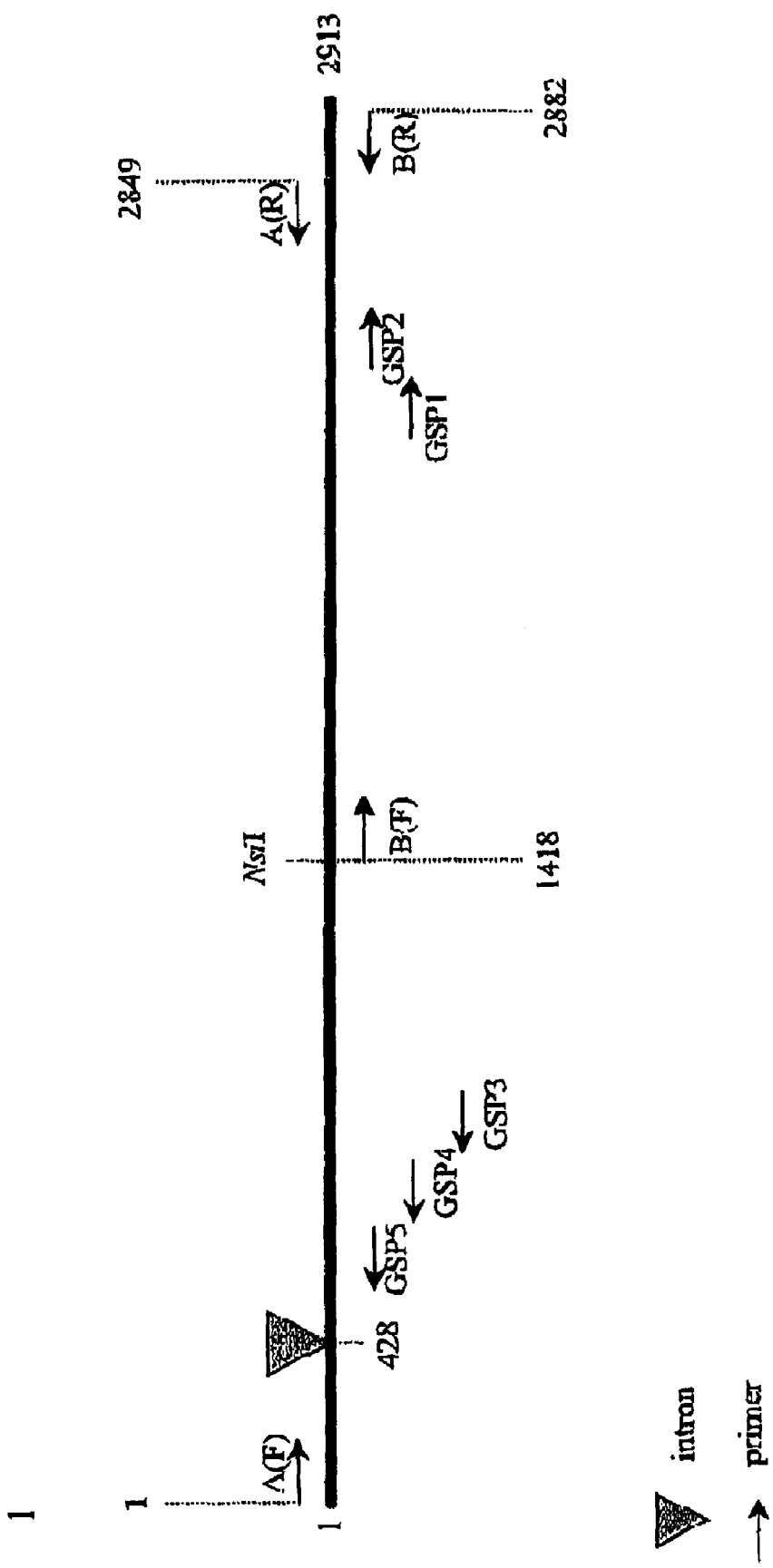
FIG. 7. Relative primer positions. The horizontal bar represents the coding sequence of the Rpi-blb gene. Numbers represent nucleotide positions. Horizontal arrows indicate relative primer positions and orientations. GSP1 and GSP2 represent nested gene specific primers used for 3' RACE experiments. GSP3 and GSP4 represent nested gene specific primers used for 5' RACE experiments. A(F), A(R), B(F) and B(R) are primers used to amplify Rpi-blb homologues. The position of the restriction site NsiI used to make domain swaps between Rpi-blb homologues is indicated.

The 5' and 3' ends of the Rpi-blb cDNA were determined by rapid amplification of cDNA ends (RACE) using the GeneRacer™ kit (Invitrogen™, The Netherlands). 3' RACE was carried out with the primers GSP1 (5'-GAGGAATC-CATCTCCCAGAG) (SEQ ID NO: 17) and GSP2 (5'-GT-GCTTGAAGAGATGATAATTCACGAG) (SEQ ID NO: 18) in combination with the GeneRacer™ 3' primer and GeneRacer™ 3' nested primer. 5' RACE was carried out on cDNA synthesised with the primer GSP3 (5'-GTCCATCTCAC-CAAGTAGTGG) (SEQ ID NO: 19) using primers GSP4 (5'-GAAATGCTCAGTAACTCTCTGG) (SEQ ID NO: 20) and GSP5 (5'-GGAGGACTGAAAGGTGTTGG) (SEQ ID NO: 21) in combination with the GeneRacer™ 5' primer and GeneRacer™ 5' nested primer (FIG. 7).

EXAMPLE 6

Structure of the Rpi-blb Gene and the Corresponding Protein

The size and structure of the Rpi-blb gene was determined by comparing the genomic sequence derived from the insert of pRGC2-blb with cDNA fragments generated by 5' and 3' rapid amplification of cDNA ends. RACE identified 5' and 3' Rpi-blb specific cDNA fragments of a single species, respectively, suggesting that the genomic clone encodes a single Rpi-blb specific transcript. The coding sequence of the Rpi-blb transcript is 2913 nucleotides. The putative Rpi-blb transcript is estimated to be 3138 nucleotides (nt) and contains a 44 and 181 nt long 5'- and 3'-untranslated region (UTR), respectively. The Rpi-blb gene contains a single intron of 678 nt starting 428 nt after the translational ATG start codon of the gene (FIG. 3C).

The deduced open reading frame of the Rpi-blb gene encodes a predicted polypeptide of 970 amino acids with an estimated molecular weight of 110.3 kD (FIG. 8). Several functional motifs present in R genes of the NBS-LRR class of plant R genes are apparent in the encoded protein which can be subdivided into 3 domains (A, B and C; FIG. 8). The N-terminal part of the protein contains potential coiled-coil domains, heptad repeats in which the first and fourth residues are generally hydrophobic (domain A). Domain B harbours the NBS and other motifs that constitute the NB-ARC domain (ARC for Apaf-1, R protein, and CED-4) of R proteins and cell death regulators in animals (van der Biezen and Jones, 1998). This domain includes the Ap-ATPase motifs present in proteins of eukaryotic and prokaryotic origin (Aravind et al., 1999 Trends Biochem. Sci. 24, 47–53). The C-terminal half of Rpi-blb comprises a series of 19–20 irregular LRRs (domain C). The LRRs can be aligned according to the consensus sequence LxxLxxLxLxxC/N/SxxLxxLPxxa (SEQ ID NO: 22). where x designates any residue and "a" designates the positions of aliphatic amino acids, followed by a region of varying length. This repeat format approximates the consensus for cytoplasmic LRRs (Jones and Jones, 1997 Adv. Bot. Res. 24, 89–167).

EXAMPLE 7

Natural Homologues and Artificial Variants of the Rpi-blb Gene

Natural Homologues

Figure 9A:
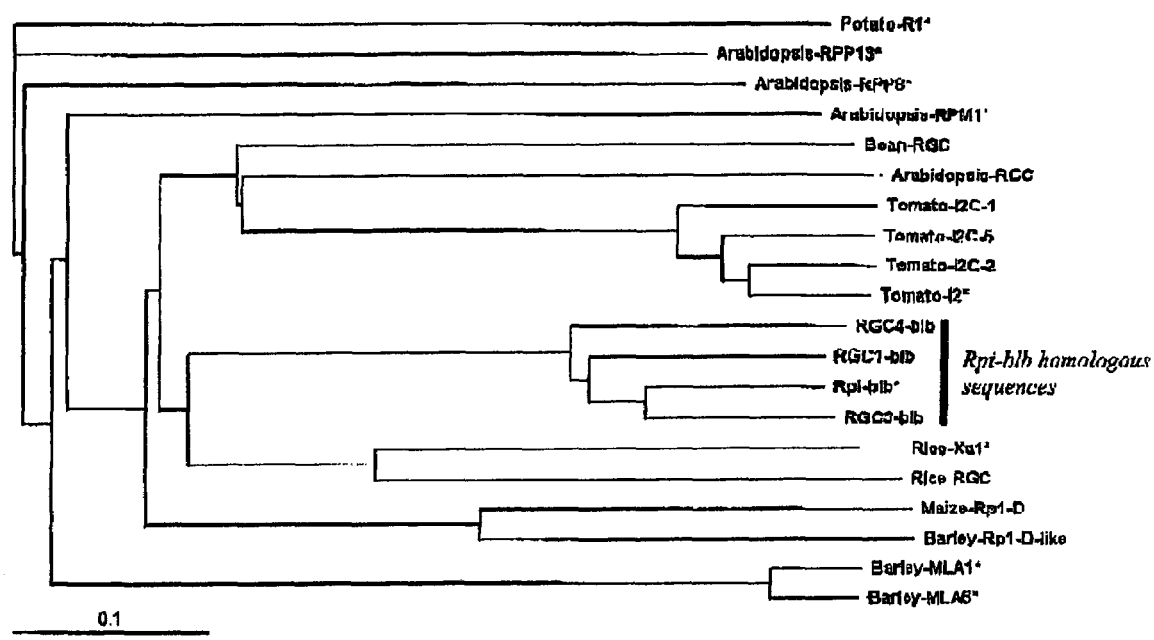
FIG. 9. Phylogenetic tree analysis. A. Phylogenetic tree of state of the art sequences which share some degree of homology to the deduced amino acid sequence of Rpi-blb and its gene cluster members RGC1-blb, RGC3-blb and RGC4-blb. The tree was made according to the Neighbour-Joining method of Saitou and Nei (1987 Molecular Biology and Evolution 4, 406–425). An asterix indicates that the gene has been assigned a function. The Rpi-blb gene cluster is boxed. B. Phylogenetic tree of state of the art sequences which share some degree of homology to the deduced amino acid sequence of Rpi-blb. Included in this analysis are the Rpi-blb homologous sequences B149-blb, SH10-tub, SH20-tub and T118-tar, sequences identified through PCR amplification using Rpi-blb gene cluster specific primers. C. Relative positions of state of the art DNA sequences which show significant homology to parts of the Rpi-blb gene sequence. Horizontal lines represent the relative positions of the homologous sequences. The degree of homology is indicated to the right of each line. The length of the homologous sequence is indicated above each line.
Figure 9B:
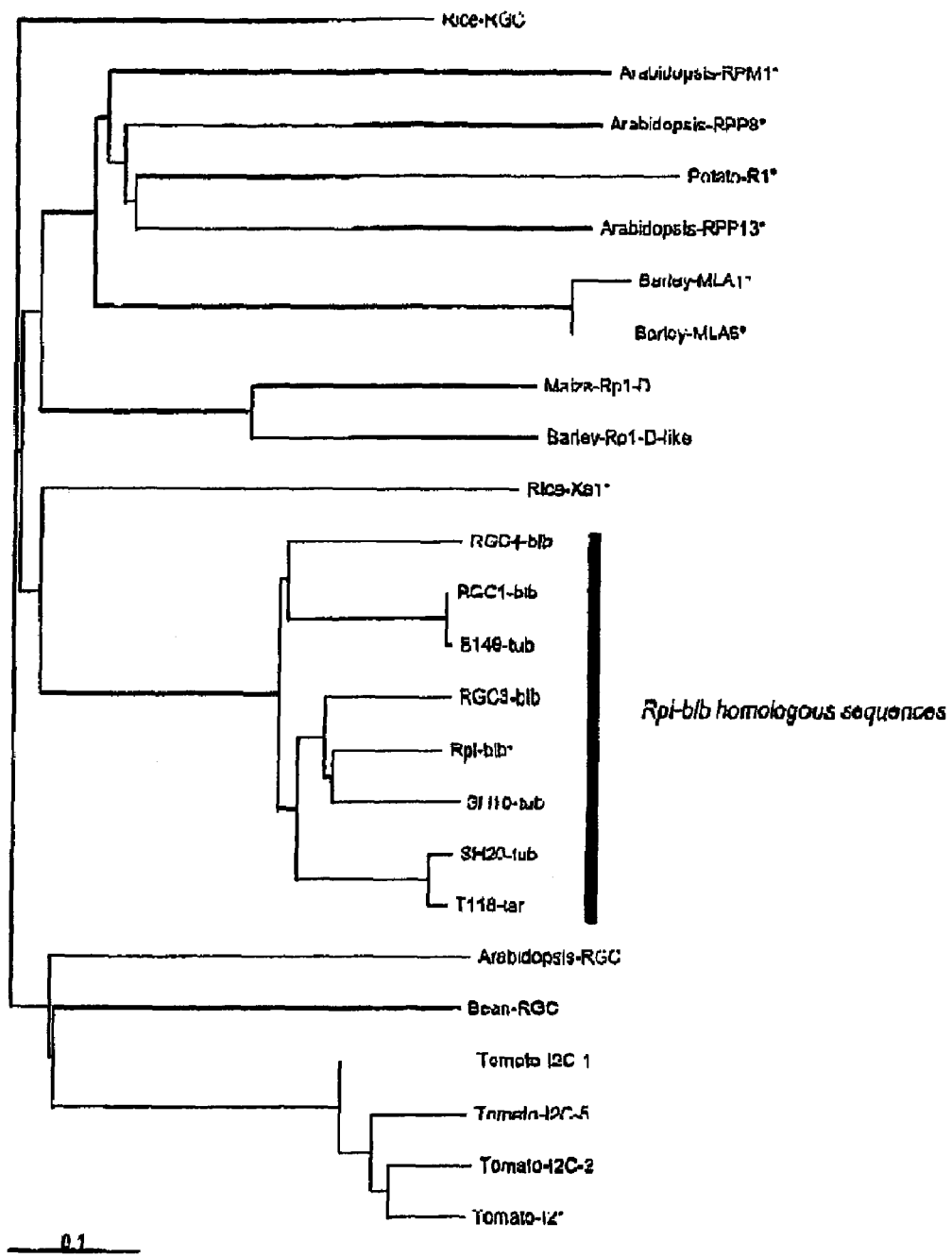
Figure 9C:
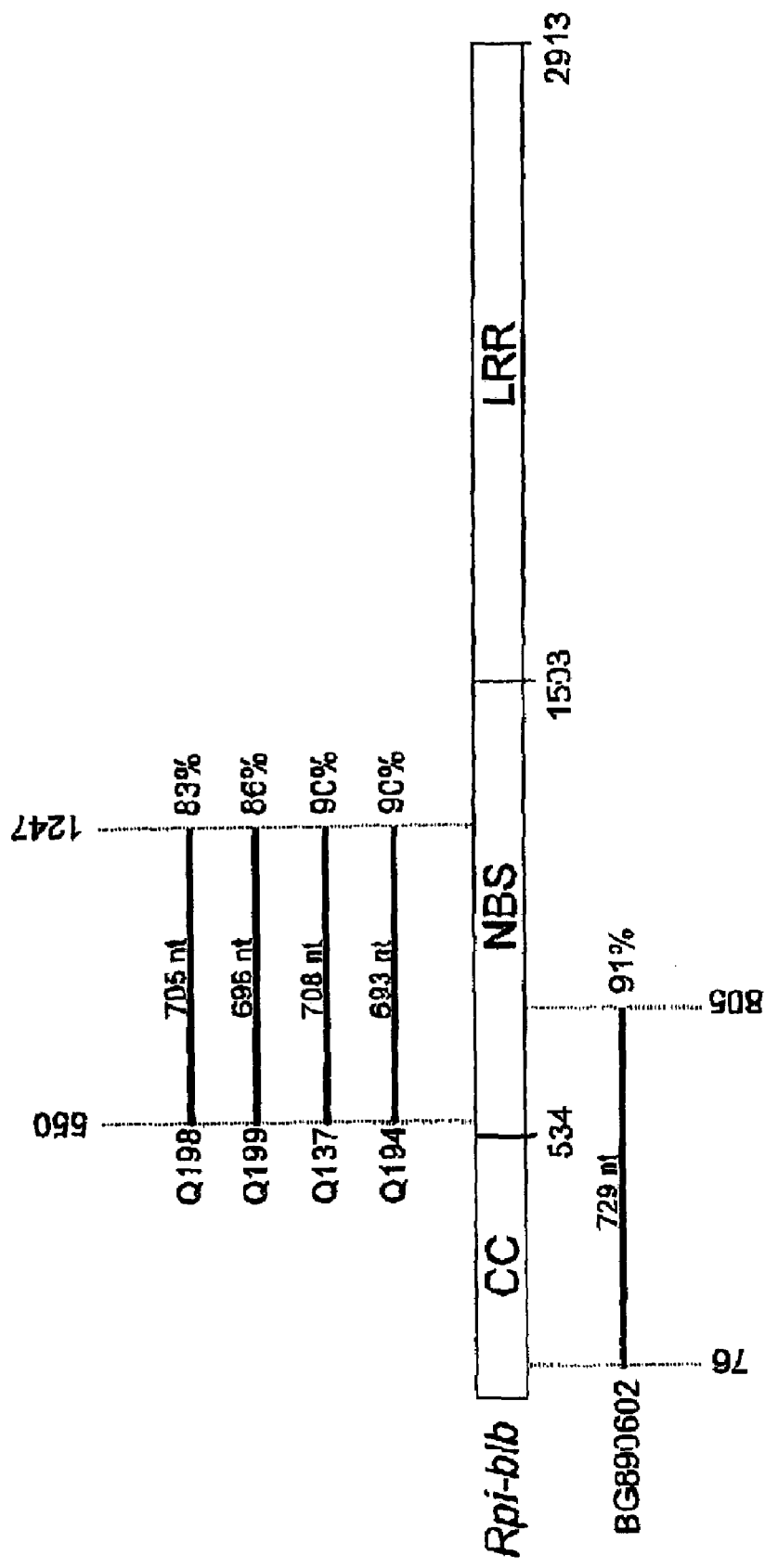
Figure 11:
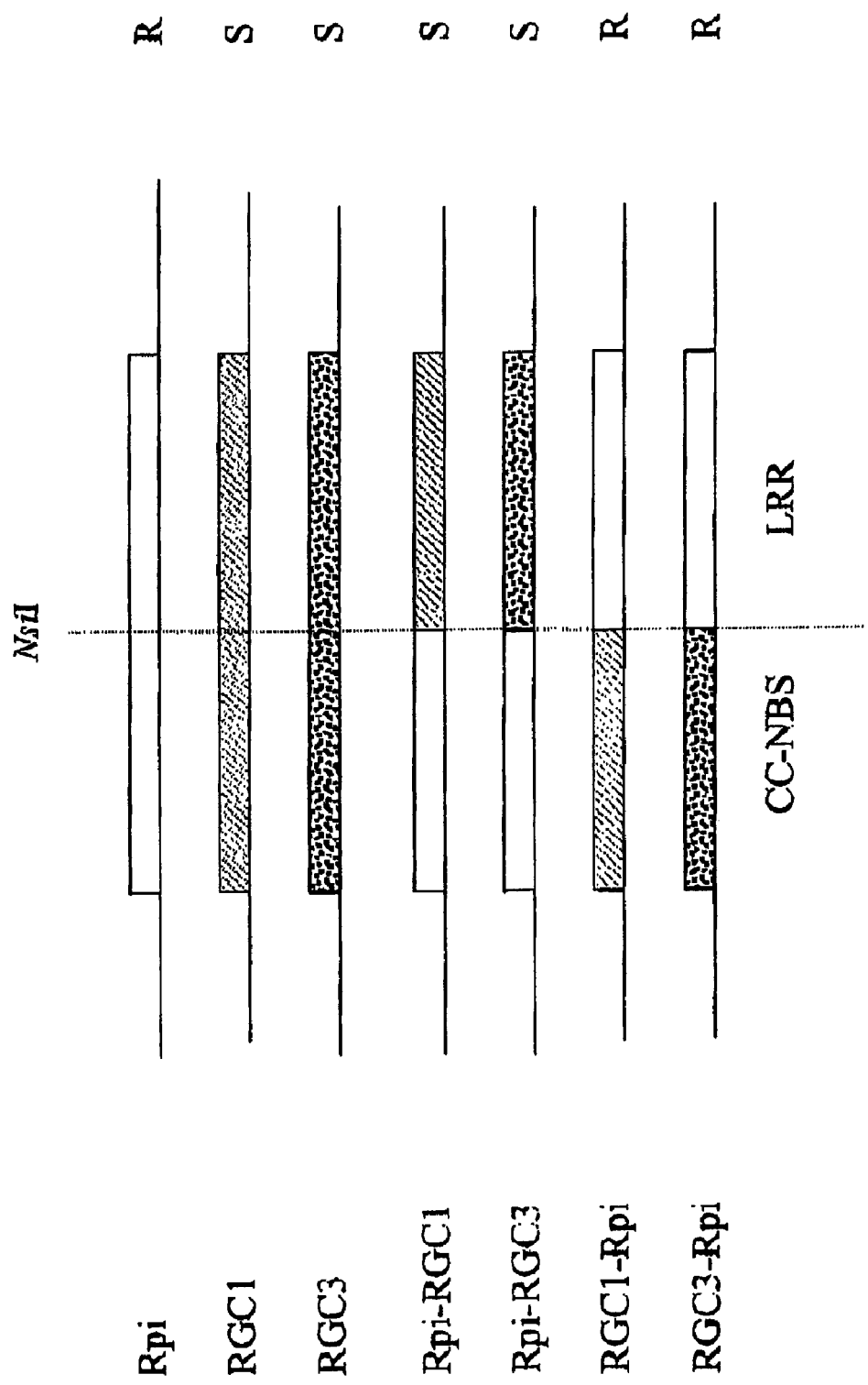
FIG. 11. Schematic overview of domain swaps made between Rpi-blb and homologues RGC1-blb and RGC3-blb. The vertical dotted line indicates the position of the NsiI site used to make the swaps. R and S indicate whether transgenic plants harbouring specific chimeric constructs are resistant or susceptible to late blight infection, respectively.

BLASTN homology searches with the coding DNA sequence of the Rpi-blb gene identified a number of sequences with significant homology to short stretches of the Rpi-blb gene (FIG. 9C). Nucleotides 549–1245 of the coding sequence of the Rpi-blb gene share 81–90% sequence identity to partial NBS fragments from tomato (e.g. Q194, Q137, Q198 and Q199; Pan et al., 2000 Genetics. 155:309–22). These homologous sequences vary in length between 525 and 708 nucleotides and are PCR fragments which were identified by systematically scanning the tomato genome using (degenerate) primer pairs based on ubiquitous NBS motifs (Pan et al., 2000 Genetics. 155:309–22; Leister et al., 1996 Nat Genet. 14:421–429). Another region of the Rpi-blb gene which shares significant homology to a state of the art sequence comprises nucleotides 76–805 of the coding sequence. This 729 nt long sequence shares 91% sequence identity to an EST from potato (EMBL database accession no. BG890602; FIG. 9C). The Rpi-blb gene sequence downstream of nucleotide 1245, comprising the LRR region, shares no significant homology to any state of the art sequence.

BLASTX homology searches with the coding sequence of the Rpi-blb gene revealed that amino acid sequence homology with various state of the art genes does not exceed 36% sequence identity (Table 4). The best BLASTX score was obtained with an NBS-LRR gene derived from *Oryza sativa* (36.5% amino acid sequence identity). NBS-LRR genes sharing an overall sequence homology of 27–36% amino-acid sequence identity with Rpi-blb can be found among others in *Arabidopsis thaliana, Phaseolus vulgaris, Lycopersicon esculentum* (*Fusarium* 12 gene cluster; Ori et al., 1997 Plant Cell, 9, 521–532; Simons et al, 1998 Plant Cell 10, 1055–1068), *Zea mays, Hordeum vulgare* and *Lactuca sativa*. Phylogenetic studies of the deduced amino acid sequences of Rpi-blb, RGC1-blb, RGC3-blb, RGC4-blb and those of the homologous state of the art genes (as defined by BLASTX) derived from diverse species, using the Neighbour-Joining method of Saitou and Nei (1987 Molecular Biology and Evolution 4, 406–425), shows that members of the Rpi-blb gene cluster can be placed in a separate branch (FIG. 9).

Sequence comparisons of the four RGCs of the Rpi-blb gene cluster identified on 8005-8 BAC clone SPB4 show that sequence homology within the Rpi-blb gene cluster varies between 70% and 81% at the amino acid level. The deduced amino acid sequence of Rpi-blb shares the highest overall homology with RGC3-blb (81% amino acid sequence identity; Table 4). When the different domains are compared it is clear that the N-terminal halves of the proteins (coiled-coil and NB-ARC domains) share a higher degree of homology (91% amino acid sequence identity) than the C-terminal halves of these proteins (LRRs; 71% amino acid sequence identity). The N-terminus of NBS-LRR proteins influences the requirement for downstream signalling components and is therefore thought to be the putative effector domain (Feys and Parker, 2000 Trends Genet 16:449–55). The C-terminal LRR region is implicated, by genetic studies, in elicitor recognition specificity (Ellis et al., 2000 Trends Plant Sci. 5:373–379; Dodds et al., 2001 Plant Cell 13:163–78).

Figure 10A:
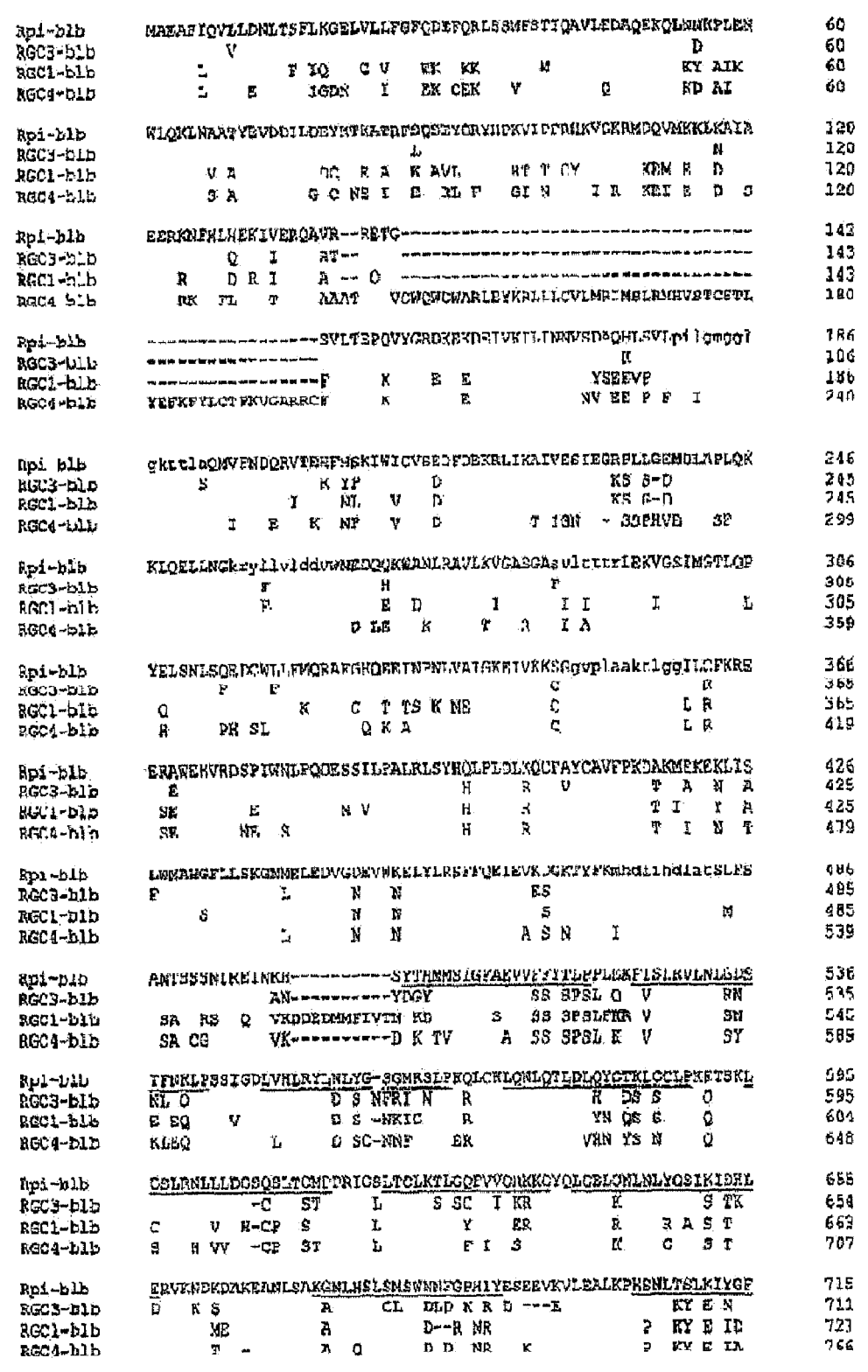

Comparison of all four amino acid sequences revealed a total of 104 Rpi-blb specific amino acid residues (FIG. 10A). The majority of these are located in the LRR region (80/104). Within the latter region, these specific residues are concentrated in the LRR subdomain xxLxLxxxx. The relative frequency of these specific amino-acid residues within this LRR subdomain is more than two times higher (28.3%) than that observed in the rest of the LRR domain (12.3%). The residues positioned around the two conserved leucine residues in the consensus xxLxxLxxxx are thought to be solvent exposed and are therefore likely to be involved in creating/maintaining recognition specificity of the resistance protein.

Figure 10B:
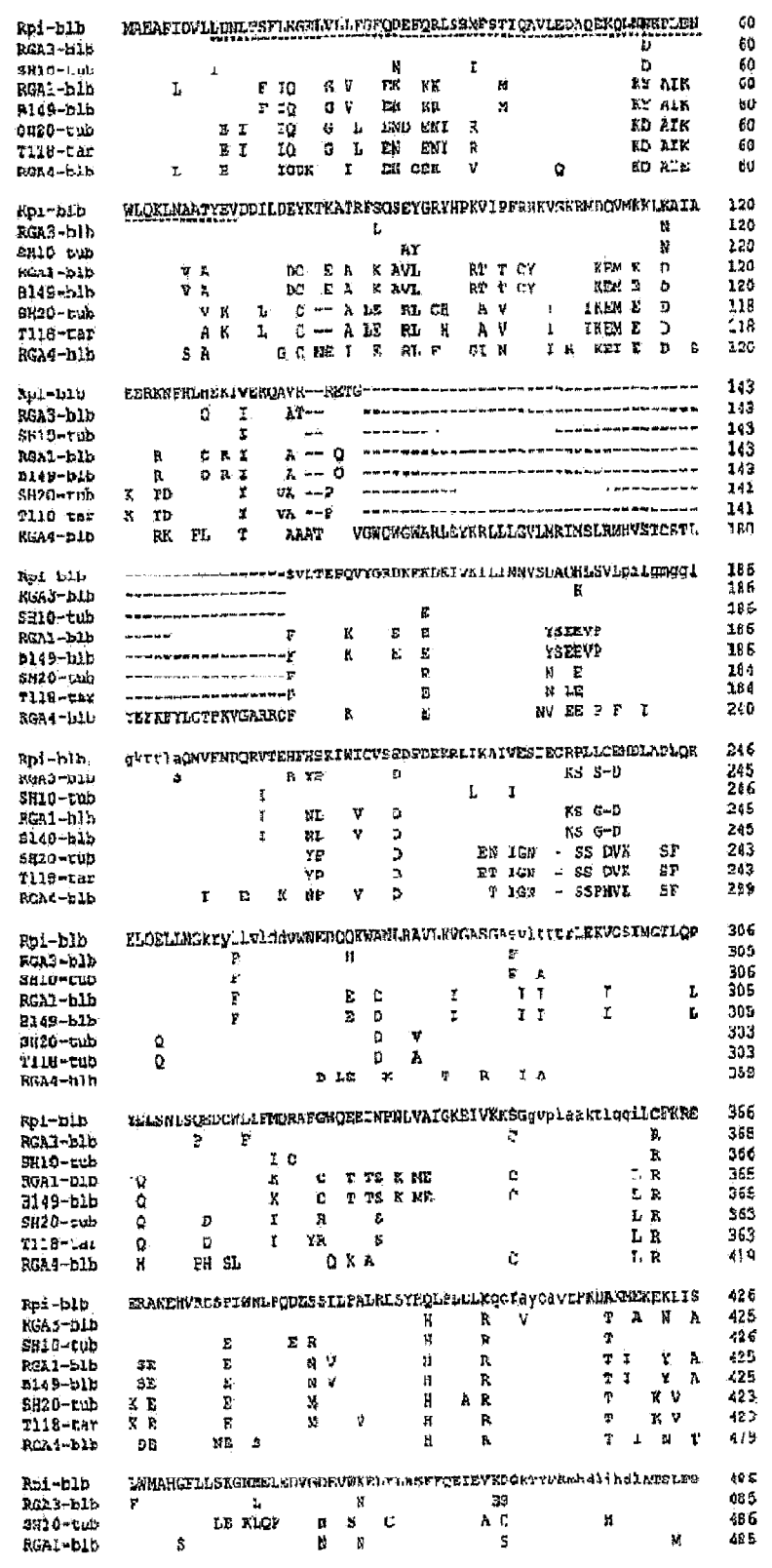

Sequences of additional homologues of the Rpi-blb gene can be obtained by screening genomic DNA or insert libraries, e.g. BAC libraries with primers based on signature sequences of the Rpi-blb gene. Screening of various *Solanum* BAC libraries with primer sets A and/or B (Table 2 and FIG. 7) identified other Rpi-blb homologues derived from *Solanum bulbocastanum* (B149-blb), *S. tuberosum* (SH 10-tub and SH20-tub) and *S. tarijense* (T118-tar). Comparison of all 8 protein sequences reduces the number of Rpi-blb specific amino acid residues to 51 (51/970; 5.25%) (FIG. 10B). The majority of these are located in the LRR region (42/51; 82%). The relative frequency of these specific amino-acid residues within the LRR subdomain xxLxlxxxx is 3.3 times higher than that observed in the rest of the LRR domain (18.8% versus 5.7%, respectively). These data clearly suggest that evolution of *P. infestans* resistance specificity within the Rpi-blb gene cluster has mainly evolved through shifts in Rpi-blb LRR specific residues.

Inclusion of the additional Rpi-blb homologues in the above described phylogenetic tree analyses, using the Neighbour-Joining method of Saitou and Nei (1987 Molecular Biology and Evolution 4, 406–425), further justifies phylogenetic tree analysis as a method to define Rpi-blb homologous sequences (FIG. 9B). Any functional R gene product which shares at least 70% sequence identity at the amino acid level will end up in the same branch as gene products of the the Rpi-blb gene cluster and can thus be defined as being a homologue of Rpi-blb.

Artificial Variants

Domain swaps between the different homologues can be made to ascertain the role of the different sequences in *P.* infestans resistance. The restriction enzyme NsiI for example, which recognises the DNA sequence ATGCAT present in the conserved MHD motif can be used to swap the complete LRR domain of Rpi-blb with that of RGC1-blb or RGC3-blb using techniques known to those skilled in the art. Chimeric variants of the Rpi-blb gene were made which encode the N-terminal half of Rpi-blb and the C-terminal half of RGC 1-blb or RGC3-blb and visa versa, i.e., the N-terminal half of RGC1-blb or RGC3-blb and the C-terminal half of Rpi-blb (FIG. 11). These variants were transformed to the susceptible potato genotype Impala and tested for *P. infestans* resistance. Chimeric RGC3-blb genes containing the LRR domain of Rpi-blb were resistant to *P. infestans* indicating that the specificity of the Rpi-blb gene is encoded by this part of the gene.

TABLE 1

Overview of *P. infestans* susceptibility in different *S. bulbocastanum* accessions

| *S. bulbocastanum* accession | | | # | # | # | % | |
|---|---|---|---|---|---|---|---|
| CGN | BGRC | PI | Plants | R | V | susceptibility | Cluster[a] |
| 17692 | 8005 | 275193 | 11 | 10 | 1 | 9 | A |
| | 8006 | 275194 | 16 | 15 | 1 | 6 | A |
| 17693 | 8008 | 275198 | 19 | 18 | | 0 | B |
| 17687 | 7997 | 243505 | 35 | 25 | 4 | 14 | B |
| 17688 | 7999 | 255518 | 19 | 19 | 0 | 0 | C |

[a]The letters a, b and c represent relative geographical origins depicted in FIG. 1

TABLE 2

Overview of markers used for mapping Rpi-blb

| Marker | Ori[a] | Sequence[b] | SEQ ID NO: | Annealing Temp (° C.) | Restriction enzyme[c] |
|---|---|---|---|---|---|
| TG513 | F | CGTAAACGCACCAAAAGCAG | 24 | 58 | a.s. |
| | R | GATTCAAGCCAGGAACCGAG | 25 | | |
| TG330 | F | CAGCTGCCACAGCTCAAGC | 26 | 56 | TaqI |
| | R | TACCTACATGTACAGTACTGC | 27 | | |
| CT88 | F | GGCAGAAGAGCTAGGAAGAG | 28 | 57 | MboI |
| | R | ATGGCGTGATACAATCCGAG | 29 | | |
| | F | TTCAAGAGCTTGAAGACATAACA | 30 | 60 | a.s. |
| | R | ATGGCGTGATACAATCCGAG | 31 | | |
| CT64 | F | ACTAGAGGATAGATTCTTGG | 32 | 56 | CfoI |
| | R | CTGGATGCCTTTCTCTATGT | 33 | | |
| B139R | F | GATCAGAAGTGCCTTGAACC | 34 | 56 | TaqI |
| | R | CAAGGAGCTTGGTCAGCAG | 35 | | |
| SPB33L | F | ATTGCACAGGAGCAGATCTG | 36 | 59 | Hinfl |
| | R | TGTAAGAGAGCAAGAGGCAC | 37 | | |
| SPB42L | F | AGAGCAGTCTTGAAGGTTGG | 38 | 58 | CfoI |
| | R | GATGGTAACTAAGCCTCAGG | 39 | | |
| B149R | F | GACAGATTTCTCATAAACCTGC | 40 | 58 | MseI/XbaI |
| | R | AATCGTGCATCACTAGAGCG | 41 | | |
| RGC1-4 | F | TGTGGAGTAAGAGAGGAAGG | 42 | 62 | SspI/MseI |
| | R | TCAGCTGAGCAGTGTGTGG | 43 | | |
| A | F | ATGGCTGAAGCTTCATTCAAGTTCTG | 44 | 60 | |
| | R | TCACACCGCTTGATCAGTTGTGGAC | 45 | | |
| B | F | TRCATGAYCTMATCCATGATTTGC | 46 | 60 | |
| | R | GMAATTTTGTGCCAGTCTTCTCC | 47 | | |

[a]Orientation of the primer, F: forward, R: reverse
[b]primer sequences according to IUB codes
[c]a.s.: allele specific.

TABLE 3

Complementation of late blight susceptibility in potato and tomato

| Genotype[a] | RGA-containing plants/ transformants | R plants/ RGA-containing plants |
|---|---|---|
| IMP(RGC1-blb) | 15/17[b] | 0/15 |
|  | 8/9[d] | 0/8 |
| IMP(RGC2-blb) | 6/31[c] | 6/6 |
|  | 12/14[d] | 9/12 |
| IMP(RGC3-blb) | 0/6[c] | — |
|  | 5/5[d] | 0/5 |
| IMP(RGC4-blb) | 18/19[b] | 0/18 |
|  | 1/12[c] | 0/1 |
| IMP(vector) | 8/8[b] | 0/8 |
|  | 9/10[d] | 0/9 |
| MM(RGC2-blb) | 9/11[d] | 7/9 |

[a]Primary transformants obtained from transformation of the susceptible potato and tomato genotypes Impala (IMP) and Moneymaker (MM), respectively, with T-DNA constructs containing the Rpi-blb gene candidates RGC1-blb, RGC2-blb, RGC3-blb or RGC4-blb. *Agrobacterium tumefaciens* strains AGL0[b], LBA4404[c], or UIA143[d] were used for transformation. Resistance was tested in detached leaf assays using the complex isolates IPO655-2A and IPO428-2.

TABLE 4

Comparison of nucleotide and amino acid sequence homology

| | | 8005-8 BAC SPB4 | | | | | |
|---|---|---|---|---|---|---|---|
| | | RGC3-blb | RGC1-blb | RGC4-blb | Rice RGC | Arabidopsis RGC | Tomato I2C-1 |
| Rpi-blb | nt[a] | 88 | 84 | 81 | — | — | — |
|  | aa[a] | 81 | 76 | 70 | 36 | 32 | 32 |
|  |  | N[b] C[b] | N C | N C | | | |
|  |  | 91 71 | 79 72 | 75 66 | | | |

[a]Percentage nucleotide (nt) and amino acid (aa) sequence identity.

[b]Separate comparisons were made for the N-terminal (N) and C-terminal (C) halves of the protein sequences. The border between the two halves is the conserved NsiI restriction site in the DNA sequence (position 1417 of the Rpi-blb coding sequence).

The invention claimed is:

1. An isolated or recombinant nucleic acid comprising:
   a) a nucleic acid encoding a polypeptide having the amino acid sequence of SEQ ID NO: 54;
   b) a nucleic acid having at least 95% homology to the nucleic acid sequence of SEQ ID NO: 48, SEQ ID NO: 49, or SEQ ID NO: 50 and encoding a polypeptide that confers resistance to a plant against an oomycete pathogen;
   c) a nucleic acid encoding a polypeptide having at least 82% homology with the amino acid sequence of SEQ ID NO: 54 and further comprises the leucine rich repeat (LRR) domain of SEQ ID NO: 54, and which confers resistance to a plant against an oomycete pathogen; or
   d) a nucleic acid encoding a polypeptide having at least 95% homology to SEQ ID NO: 54 and that confers resistance to a plant against an Oomycete pathogen.

2. The nucleic acid according to claim 1, said nucleic acid encoding a gene product which provides a member of the Solanaceae family with resistance against an oomycete pathogen.

3. The nucleic acid according to claim 2 wherein said member of the Solanaceae family is *S. tuberosum*.

4. The nucleic acid according to claim 2 where said resistance is race non-specific.

5. The nucleic acid according to claim 1 comprising a nucleic acid sequence as depicted in SEQ ID NO: 48, SEQ ID NO: 49, or SEQ ID NO: 50.

6. A vector comprising the nucleic acid according to claim 1.

7. A transformed host cell comprising the nucleic acid according to claim 1.

8. The host cell according to claim 7 comprising a plant cell.

9. The host cell according to claim 8, wherein said plant cell is from a plant of the Solanaceae family.

10. A plant comprising the cell according to claim 7.

11. A transformed plant part derived from the plant according to claim 10.

12. The transformed plant part according to claim 11 comprising a tuber, fruit, or seed.

13. A transformed progeny of the plant according to claim 10.

14. A method for producing a plant or progeny thereof with resistance against an oomycete infection, which comprises transforming the plant or progeny thereof with the nucleic acid according to claim 1, and growing said plant or progeny thereof.

15. The method according to claim 14, wherein said oomycete comprises *Phytophthora infestans*.

16. The method according to claim 14, wherein said plant is *S. tuberosum*.

17. An isolated or recombinant nucleic acid comprising a nucleic acid encoding the amino acid sequence of SEQ ID NO: 54, or a homologue thereof having at least 95% homology to the amino acid sequence of SEQ ID NO: 54 which confers resistance to a plant against an oomycete pathogen when expressed in the plant.

18. The nucleic acid according to claim 17, wherein the homologue shares at least 99% homology with the amino acid sequence of SEQ ID NO: 54.

19. The nucleic acid according to claim 2, wherein said oomycete pathogen is *Phytophthora infestans*.

20. The plant part according to claim 12, wherein said tuber is a potato tuber.

21. The plant part according to claim 12, wherein said fruit is a tomato fruit.

22. An isolated or recombinant nucleic acid comprising a nucleic acid coding for the C-terminal fragment comprising the leucine rich repeat (LRR) domain of SEQ ID NO: 54.

23. The isolated or recombinant nucleic acid of claim 1, wherein the nucleic acid encodes a polypeptide having at least 82% homology with the amino acid sequence of SEQ ID NO:

54 and further comprises the leucine rich repeat (LRR) domain of SEQ ID NO: 54, and which confers resistance to a plant against an oomycete pathogen.

24. A transformed host cell comprising the nucleic acid according to claim 22.

25. A plant comprising the cell according to claim 24.

26. A transformed plant part derived from the plant according to claim 25.

27. A cultivated potato plant or part thereof which contains the isolated nucleic acid sequence of SEQ ID NO: 48, SEQ ID NO: 49, or SEQ ID NO: 50.

28. A transgenic potato plant or part thereof which comprises an isolated nucleic acid coding for the amino acid sequence of SEQ ID NO: 54.

29. A host cell comprising the vector of claim 6.

30. The host cell of claim 29 comprising a plant cell.

31. A plant comprising the cell of claim 30.

32. A plant comprising the vector according to claim 6.

* * * * *

SEQUENCE LISTING

```
<160> NUMBER OF SEQ ID NOS: 63
<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      concentration in LRR subdomain
<220> FEATURE:
<221> NAME/KEY: SITE
<222> LOCATION: (1)..(9)
<223> OTHER INFORMATION: /note="X stands for any amino acid"

<400> SEQUENCE: 1

Xaa Xaa Leu Xaa Leu Xaa Xaa Xaa Xaa
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: consensus
<220> FEATURE:
<221> NAME/KEY: SITE
<222> LOCATION: (1)..(10)
<223> OTHER INFORMATION: /note="X stands for any amino acid"

<400> SEQUENCE: 2

Xaa Xaa Leu Xaa Xaa Leu Xaa Xaa Xaa Xaa
 1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein
```

```
<400> SEQUENCE: 3

Arg Pro Leu Leu Gly Glu Met
  1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 4

Ala Lys Met Glu Lys Glu Lys Leu Ile Ser
  1               5                  10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 5

Lys His Ser Tyr Thr His Met Met
  1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 6

Phe Phe Tyr Thr Leu Pro Pro Leu Glu Lys Phe Ile
  1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 7

Gly Asp Ser Thr Phe Asn Lys
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 8

Asn Leu Tyr Gly Ser Gly Met Arg Ser
  1               5

<210> SEQ ID NO 9
<211> LENGTH: 8
<212> TYPE: PRT
```

```
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 9

Leu Gln Tyr Cys Thr Lys Leu Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 10

Gly Ser Gln Ser Leu Thr Cys Met
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 11

Asn Asn Phe Gly Pro His Ile
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 12

Thr Ser Leu Lys Ile Tyr Gly Phe Arg Gly Ile His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 13

Ile Ile His Glu Cys Pro Phe Leu Thr Leu Ser
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 14

Arg Ile Cys Tyr Asn Lys Val Ala
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: sequence
      which is relatively unique to Rpi-blb protein

<400> SEQUENCE: 15

Lys Tyr Leu Thr Ile Ser Arg Cys Asn
  1               5

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: oligo d(T)
      primer
<220> FEATURE:
<221> NAME/KEY: misc_feature
<222> LOCATION: (1)..(54)

<400> SEQUENCE: 16
gctgtcaacg atacgctacg taacggcatg acagtgtttt ttttttttttt tttt          54

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer GSP1
<220> FEATURE:
<221> NAME/KEY: misc_feature
<222> LOCATION: (1)..(20)

<400> SEQUENCE: 17
gaggaatcca tctcccagag                                                 20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: primer GSP2
<220> FEATURE:
<221> NAME/KEY: misc_feature
<222> LOCATION: (1)..(27)

<400> SEQUENCE: 18
gtgcttgaag agatgataat tcacgag                                         27

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: primer GSP3
<220> FEATURE:
<221> NAME/KEY: misc_feature
<222> LOCATION: (1)..(21)

<400> SEQUENCE: 19
gtccatctca ccaagtagtg g                                               21

<210> SEQ ID NO 20
<211> LENGTH: 22
```

```
<212> TYPE: DNA
<213> ORGANISM: Artificial Sequence
<220> FEATURE:
<223> OTHER INFORMATION: Description of Artificial Sequence: primer GSP4
<220> FEATURE:
<221> NAME/KEY: misc_feature
<222> LOCATION: (1)..(22)

<400> SEQUENCE: 20
gaaatgctca gtaactctct gg                                              22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer GSP5
<220> FEATURE:
<221> NAME/KEY: misc_feature
<222> LOCATION: (1)..(20)

<400> SEQUENCE: 21
ggaggactga aaggtgttgg                                                 20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: consensus
<220> FEATURE:
<221> NAME/KEY: SITE
<222> LOCATION: (1)..(22)
<223> OTHER INFORMATION: /note="X on positions 2, 3, 5, 6, 8, 10, 11, 13,
      14, 16, 17, 20 and 21 stand for any amino acid, X
      on position 12 stands for C/N or S, X on position
      22 stands for aliphatic amino acid"

<400> SEQUENCE: 22

Leu Xaa Xaa Leu Xaa Xaa Leu Xaa Leu Xaa Xaa Xaa Xaa Xaa Leu Xaa
 1               5                  10                  15

Xaa Leu Pro Xaa Xaa Xaa
            20

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: NsiI-site
<220> FEATURE:
<221> NAME/KEY: misc_feature
<222> LOCATION: (1)..(6)

<400> SEQUENCE: 23 atgcat                                                                 6

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 24
```
cgtaaacgca ccaaaagcag                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 25
gattcaagcc aggaaccgag                                              20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(19)

<400> SEQUENCE: 26
cagctgccac agctcaagc                                               19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(21)

<400> SEQUENCE: 27
tacctacatg tacagtactg c                                            21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 28
ggcagaagag ctaggaagag                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 29

```
atggcgtgat acaatccgag                                               20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(23)

<400> SEQUENCE: 30
ttcaagagct tgaagacata aca                                           23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 31
atggcgtgat acaatccgag                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 32
actagaggat agattcttgg                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 33
ctggatgcct ttctctatgt                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)
```

```
<400> SEQUENCE: 34
gatcagaagt gccttgaacc                                              20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(19)

<400> SEQUENCE: 35
caaggagctt ggtcagcag                                               19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 36
attgcacagg agcagatctg                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 37
tgtaagagag caagaggcac                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 38
agagcagtct tgaaggttgg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)
```

-continued

```
<400> SEQUENCE: 39
gatggtaact aagcctcagg                                                    20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(22)

<400> SEQUENCE: 40
gacagatttc tcataaacct gc                                                 22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(20)

<400> SEQUENCE: 41
aatcgtgcat cactagagcg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(20)

<400> SEQUENCE: 42
tgtggagtaa gagaggaagg                                                    20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(19)

<400> SEQUENCE: 43
tcagctgagc agtgtgtgg                                                     19

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
```

```
<222> LOCATION: (1)..(27)

<400> SEQUENCE: 44
atggctgaag ctttcattca agttctg                                          27

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(25)

<400> SEQUENCE: 45
tcacaccgct tgatcagttg tggac                                            25

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: forward
      primer
<220> FEATURE:
<221> NAME/KEY: misc_feature
<222> LOCATION: (1)..(24)

<400> SEQUENCE: 46
trcatgayct matccatgat ttgc                                             24

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: reverse
      primer
<220> FEATURE:
<221> NAME/KEY: misc_feature
<222> LOCATION: (1)..(23)

<400> SEQUENCE: 47
gmaattttgt gccagtcttc tcc                                              23

<210> SEQ ID NO 48
<211> LENGTH: 2913
<212> TYPE: DNA
<213> ORGANISM: Solanum bulbocastanum
<220> FEATURE:
<221> NAME/KEY: misc_feature
<222> LOCATION: (1)..(2913)
<223> OTHER INFORMATION: /note="Rpi-blb"

<400> SEQUENCE: 48
atggctgaag ctttcattca agttctgcta gacaatctca cttctttcct caaagggaa       60 cttgtattgc ttttcggttt tcaagatgag ttccaaaggc tttcaagcat gttttctaca     120
attcaagccg tccttgaaga tgctcaggag aagcaactca caacaagcc tctagaaaat      180 tggttgcaaa aactcaatgc tgctacatat gaagtcgatg acatcttgga tgaatataaa     240
accaaggcca caagattctc ccagtctgaa tatggccgtt atcatccaaa ggttatccct     300
ttccgtcaca aggtcgggaa aaggatggac caagtgatga aaaaactaaa ggcaattgct     360
gaggaaagaa agaattttca tttgcacgaa aaaattgtag agagacaagc tgttagacgg     420
```

-continued

```
gaaacaggtt ctgtattaac cgaaccgcag gtttatggaa gagacaaaga gaaagatgag    480
atagtgaaaa tcctaataaa caatgttagt gatgcccaac acctttcagt cctcccaata    540
cttggtatgg ggggattagg aaaaacgact cttgcccaaa tggtcttcaa tgaccagaga    600
gttactgagc atttccattc caaaatatgg atttgtgtct cggaagattt tgatgagaag    660
aggttaataa aggcaattgt agaatctatt gaaggaaggc cactacttgg tgagatggac    720
ttggctccac ttcaaaagaa gcttcaggag ttgctgaatg aaaaagata cttgcttgtc     780 ttagatgatg tttggaatga agatcaacag aagtgggcta atttaagagc agtcttgaag    840
gttggagcaa gtggtgcttc tgttctaacc actactcgtc ttgaaaaggt tggatcaatt    900
atgggaacat gcaaccata tgaactgtca atctgtctc aagaagattg ttggttgttg      960
ttcatgcaac gtgcatttgg acaccaagaa gaaataaatc caaaccttgt ggcaatcgga   1020
aaggagattg tgaaaaaaag tggtggtgtg cctctagcag ccaaaactct tggaggtatt   1080
ttgtgcttca agagagaaga aagagcatgg gaacatgtga gagacagtcc gatttggaat   1140
ttgcctcaag atgaaagttc tattctgcct gccctgaggc ttagttacca tcaacttcca   1200
cttgatttga acaatgctt tgcgtattgt gcggtgttcc caaaggatgc caaaatggaa    1260
aaagaaaagc taatctctct ctggatggcg catggttttc ttttatcaaa aggaaacatg   1320
gagctagagg atgtgggcga tgaagtatgg aaagaattat acttgaggtc ttttttccaa   1380
gagattgaag ttaagatgg taaaacttat ttcaagatgc atgatctcat ccatgatttg    1440
gcaacatctc tgttttcagc aaacacatca agcagcaata ccgtgaaat aaataaacac    1500 agttacacac atatgatgtc cattggtttc gccgaagtgg tgtttttta cactcttccc    1560 cccttggaaa agtttatctc gttaagagtg cttaatctag gtgattcgac atttaataag   1620
ttaccatctt ccattggaga tctagtacat ttaagatact tgaacctgta tggcagtggc   1680
atgcgtagtc ttccaaagca gttatgcaag cttcaaaatc tgcaaactct tgatctacaa   1740
tattgcacca agctttgttg tttgccaaaa gaaacaagta aacttggtag tctccgaaat   1800
cttttacttg atggtagcca gtcattgact tgtatgccac caaggatagg atcattgaca   1860
tgccttaaga ctctaggtca atttgttgtt ggaaggaaga aaggttatca acttggtgaa   1920
ctaggaaacc taaatctcta tggctcaatt aaaatctcgc atcttgagag agtgaagaat   1980
gataaggacg caaagaagc caatttatct gcaaaggga atctgcattc tttaagcatg    2040
agttggaata ctttggacc acatatatat gaatcagaag aagttaaagt gcttgaagcc    2100
ctcaaaccac actccaatct gacttcttta aaaatctatg gcttcagagg aatccatctc   2160
ccagagtgga tgaatcactc agtattgaaa aatattgtct ctattctaat tagcaacttc   2220
agaaactgct catgcttacc acccttggt gatctgcctt gtctagaaag tctagagtta    2280
cactgggggt ctgcggatgt ggagtatgtt gaagaagtgg atattgatgt tcattctgga   2340
ttccccacaa gaataaggtt tccatccttg aggaaacttg atatatggga ctttggtagt   2400
ctgaaaggat tgctgaaaaa ggaaggagaa gagcaattcc ctgtgcttga agagatgata   2460
attcacgagt gccctttct gacccttct tctaatctta gggctcttac ttccctcaga    2520
atttgctata ataaagtagc tacttcattc ccagaagaga tgttcaaaaa ccttgcaaat   2580
ctcaaatact tgacaatctc tcggtgcaat aatctcaaag actgcctac cagcttggct    2640 agtctgaatg ctttgaaaag tctaaaaatt caattgtgtt gcgcactaga gagtctccct   2700
gaggaagggc tggaaggttt atcttcactc acagagttat tgttgaaca ctgtaacatg    2760
```

| | |
|---|---|
| ctaaaatgtt taccagaggg attgcagcac ctaacaaccc tcacaagttt aaaaattcgg | 2820 |
| ggatgtccac aactgatcaa gcggtgtgag aagggaatag gagaagactg gcacaaaatt | 2880 |
| tctcacattc ctaatgtgaa tatatatatt taa | 2913 |

<210> SEQ ID NO 49
<211> LENGTH: 3592
<212> TYPE: DNA
<213> ORGANISM: Solanum bulbocastanum
<220> FEATURE:
<221> NAME/KEY: misc_feature
<222> LOCATION: (1)..(3591)
<223> OTHER INFORMATION: /note="Rpi-blb including intron sequence (position 428-1106)"

<400> SEQUENCE: 49

| | |
|---|---|
| atggctgaag ctttcattca agttctgcta gacaatctca cttctttcct caaggggaa | 60 |
| cttgtattgc ttttcggttt tcaagatgag ttccaaaggc tttcaagcat gttttctaca | 120 |
| attcaagccg tccttgaaga tgctcaggag aagcaactca caacaagcc tctagaaaat | 180 |
| tggttgcaaa aactcaatgc tgctacatat gaagtcgatg acatcttgga tgaatataaa | 240 |
| accaaggcca caagattctc ccagtctgaa tatggccgtt atcatccaaa ggttatccct | 300 |
| ttccgtcaca aggtcgggaa aaggatggac caagtgatga aaaaactaaa ggcaattgct | 360 |
| gaggaaagaa agaatttttca tttgcacgaa aaaattgtag agagacaagc tgttagacgg | 420 |
| gaaacaggta ctcatcttaa attagtatta caacaactaa gtttatattc attttttttgg | 480 |
| caattatcaa attcagaaaa gggttaaata tactcatgtc ctatcgtaaa tagtgtatat | 540 |
| atacctctcg ttgtacttttc gatctgaata tacttgtcaa atctggcaag ctcagaatca | 600 |
| aattatccac cccaactttt aaatactcga tatcttttaga aatccacctg tctaactcat | 660 |
| ccactaccca ttcccttgtc tttgaattct tttctttacc tataaacttg gaacactcga | 720 |
| tccgttttgc ttttcttaac aaagcagctc agagaaaaga ggttttcttc tattctgttt | 780 |
| ctctgtgtgc tgcacttggg tccttaatcc cattaaaaac agggcatgtt aatcccaacg | 840 |
| acggtagcct ttcctgacag ctgactgtaa attttgtcta acaaagaaaa aaaaagatta | 900 |
| gacatgtttt tccttgtcat tgattaggct ggatttcttt cagagtggaa catagggggat | 960 |
| atattggacc aaaagtagaa tgggtatata tttaaagtat ttctgataga acaggagtat | 1020 |
| attgtgcgaa aatatcctct atttttctgtt gtctcctaat gagtttgaat gtaataatat | 1080 |
| tctcatgtgg acattgcttg caccaggttc tgtattaacc gaaccgcagg tttatggaag | 1140 |
| agacaaagag aaagatgaga tagtgaaaat cctaataaac aatgttagtg atgcccaaca | 1200 |
| cctttcagtc ctcccaatac ttggtatggg gggattagga aaaacgactc ttgcccaaat | 1260 |
| ggtcttcaat gaccagagag ttactgagca tttccattcc aaaatatgga tttgtgtctc | 1320 |
| ggaagatttt gatgagaaga ggttaataaa ggcaattgta gaatctattg aaggaaggcc | 1380 |
| actacttggt gagatggact tggctccact tcaaaagaag cttcaggagt tgctgaatgg | 1440 |
| aaaaagatac ttgcttgtct tagatgatgt ttggaatgaa gatcaacaga agtgggctaa | 1500 |
| tttaagagca gtcttgaagg ttggagcaag tggtgcttct gttctaacca ctactcgtct | 1560 |
| tgaaaaggtt ggatcaatta tgggaacatt gcaaccatat gaactgtcaa atctgtctca | 1620 |
| agaagattgt tggttgttgt tcatgcaacg tgcatttgga caccaagaag aaataaatcc | 1680 |
| aaaccttgtg gcaatcggaa aggagattgt gaaaaaagt ggtggtgtgc ctctagcagc | 1740 |
| caaaactctt ggaggtattt tgtgcttcaa gagaagaaga agagcatggg aacatgtgag | 1800 |

```
agacagtccg atttggaatt tgcctcaaga tgaaagttct attctgcctg ccctgaggct    1860
tagttaccat caacttccac ttgatttgaa acaatgcttt gcgtattgtg cggtgttccc    1920
aaaggatgcc aaaatggaaa agaaaagct aatctctctc tggatggcgc atggttttct     1980
tttatcaaaa ggaaacatgg agctagagga tgtgggcgat gaagtatgga agaattata    2040 cttgaggtct tttttccaag agattgaagt taaagatggt aaaacttatt tcaagatgca    2100
tgatctcatc catgatttgg caacatctct gttttcagca acacatcaa gcagcaatat     2160 ccgtgaaata aataaacaca gttacacaca tatgatgtcc attggtttcg ccgaagtggt    2220 gttttttac actcttcccc ccttggaaaa gtttatctcg ttaagagtgc ttaatctagg     2280
tgattcgaca tttaataagt taccatcttc cattggagat ctagtacatt taagatactt    2340
gaacctgtat ggcagtggca tgcgtagtct tccaaagcag ttatgcaagc ttcaaaatct    2400
gcaaactctt gatctacaat attgcaccaa gctttgttgt ttgccaaaag aaacaagtaa    2460
acttggtagt ctccgaaatc ttttacttga tggtagccag tcattgactt gtatgccacc    2520
aaggatagga tcattgacat gccttaagac tctaggtcaa tttgttgttg aaggaagaa     2580 aggttatcaa cttggtgaac taggaaacct aaatctctat ggctcaatta aaatctcgca    2640
tcttgagaga gtgaagaatg ataaggacgc aaaagaagcc aatttatctg caaagggaa     2700 tctgcattct ttaagcatga gttggaataa ctttggacca catatatatg aatcagaaga    2760
agttaaagtg cttgaagccc tcaaaccaca ctccaatctg acttctttaa aaatctatgg    2820
cttcagagga atccatctcc cagagtggat gaatcactca gtattgaaaa atattgtctc    2880
tattctaatt agcaacttca gaaactgctc atgcttacca cccttggtg atctgccttg     2940 tctagaaagt ctagagttac actgggggtc tgcggatgtg gagtatgttg aagaagtgga    3000
tattgatgtt cattctggat tccccacaag aataaggttt ccatccttga ggaaacttga    3060
tatatgggac tttggtagtc tgaaaggatt gctgaaaaag gaaggagaag agcaattccc    3120
tgtgcttgaa gagatgataa ttcacgagtg cccttttctg acccttttctt ctaatcttag    3180 ggctcttact tccctcagaa tttgctataa taaagtagct acttcattcc cagaagagat    3240
gttcaaaaac cttgcaaatc tcaaatactt gacaatctct cggtgcaata atctcaaaga    3300
gctgcctacc agcttggcta gtctgaatgc tttgaaaagt ctaaaaattc aattgtgttg    3360
cgcactagag agtctccctg aggaagggct ggaaggttta tcttcactca cagagttatt    3420
tgttgaacac tgtaacatgc taaaatgttt accagaggga ttgcagcacc taacaaccct    3480
cacaagttta aaaattcggg gatgtccaca actgatcaag cggtgtgaga agggaatagg    3540
agaagactgg cacaaaattt ctcacattcc taatgtgaat atatatattt aa           3592
```

<210> SEQ ID NO 50
<211> LENGTH: 5191
<212> TYPE: DNA
<213> ORGANISM: Artificial Sequence
<220> FEATURE:
<223> OTHER INFORMATION: Description of Artificial Sequence: sequence of
     5.2 kb Sca I genomic DNA fragment of S.
     bulbocastanum BAC SPB 4 present in pRGC2-blb

<400> SEQUENCE: 50

```
agtactccat ccgttcactt tgatttgtca tgttgcactt ttcgaaagtc aatttgacta      60 attttaaag ctaaattaga ttacactaat tcaatatttt aaacagaaaa attagatatt     120
caaaaactat acaaaaaata tttatacattg caattttttg catatcaata tgataaaaaa    180
atatatcgta aaatattagt caaaattttt ataatttgac tcaaatcatg aaaagtataa    240
```

```
taattaatag tggacggagg aagtattgtc tttccagatt tgtggccatt tttggtccaa    300
gggccattag cagttctctt cattttctac ttctgtctca tattagatgg gcatcttact    360
aaaaatattt gtctcatatt acttgattat ttattaaatc aaaagaatt  aattaatttt    420 ttctcatttt accootacaa ttaatatagt tttaaaagtt ttaaacaaat tttgaagaat    480
caaaatttct tttgcaagag acttattaat ataaacaaag gataaaataa taaaagctgt    540
caatttattg accatcactt aataatatat aaaatacaaa ctgctgatct aatatgagac    600
ggacaaaata tattctaaaa tattttcgga cagatatgtg atattctaac cattcactac    660
actatattat gcattttatc cgccaatgac ttatttcagc tttaattaat taggaaagag    720
gaaactgcca atgaggaaga gtaggggcgt agttgctgtc gacgaaaaaa agataatact    780
cactcttttc gattttttatt tttatttatc acttttaacc tatcatgtaa aaagataatt    840
atttttttca tgctttatcc ttagtattaa acaatttaat agggattatt ttgtaaaata    900
tttatatgaa taattgtttt cgtaatgaat tgtccggtc  aaacaatgat aaataaaaat    960
gaatgaagag agtagaaaac aaaacaaaag aacaagttga caacttgaga gattaaaagg   1020
gtccaaaacg ccttggattt tgagattcca tatgtgaaat ttccatgaaa taattgaatt   1080
tgtattatta caagtcaaac tttccatttc attccaacta gccatcttgg tttcaaaatt   1140
acacattcat tcattcacag atctaatatt cttaatagtg atttccacat atggctgaag   1200
ctttcattca agttctgcta gacaatctca cttctttcct caaggggaa  cttgtattgc   1260 ttttcggttt tcaagatgag ttccaaaggc tttcaagcat gttttctaca attcaagccg   1320
tccttgaaga tgctcaggag aagcaactca acaacaagcc tctagaaaat tggttgcaaa   1380
aactcaatgc tgctacatat gaagtcgatg acatcttgga tgaatataaa accaaggcca   1440
caagattctc ccagtctgaa tatggccgtt atcatccaaa ggttatccct ttccgtcaca   1500
aggtcgggaa aaggatggac caagtgatga aaaaactaaa ggcaattgct gaggaaagaa   1560
agaattttca tttgcacgaa aaaattgtag agagacaagc tgttagacgg gaaacaggta   1620
ctcatcttaa attagtatta caacaactaa gtttatattc attttttttgg caattatcaa   1680 attcagaaaa gggttaaata tactcatgtc ctatcgtaaa tagtgtatat atacctctcg   1740
ttgtactttc gatctgaata tacttgtcaa atctggcaag ctcagaatca aattatccac   1800
cccaactttt aaatactcga tatctttaga aatccacctg tctaactcat ccactaccca   1860
ttccctttgc tttgaattct tttcttacc  tataaacttg gaacactcga tccgttttgc   1920
ttttcttaac aaagcagctc agagaaaaga ggttttcttc tattctgttt ctctgtgtgc   1980
tgcacttggg tccttaatcc cattaaaaac agggcatgtt aatcccaacg acggtagcct   2040
ttcctgacag ctgactgtaa attttgtcta acaaagaaaa aaaagatta  gacatgtttt   2100 tccttgtcat tgattaggct ggatttcttt cagagtggaa cataggggat atattggacc   2160
aaaagtagaa tgggtatata tttaaagtat ttctgataga acaggagtat attgtgcgaa   2220
aatatcctct attttctgtt gtctcctaat gagtttgaat gtaataatat tctcatgtgg   2280
acattgcttg caccaggttc tgtattaacc gaaccgcagg tttatggaag agacaaagag   2340
aaagatgaga tagtgaaaat cctaataaac aatgttagtg atgcccaaca cctttcagtc   2400
ctcccaatac ttggtatggg gggattagga aaaacgactc ttgcccaaat ggtcttcaat   2460
gaccagagag ttactgagca tttccattcc aaaaatggga tttgtgtctc ggaagatttt   2520
gatgagaaga ggttaatataaa ggcaattgta gaatctattg aaggaaggcc actacttggt   2580
```

```
gagatggact tggctccact tcaaaagaag cttcaggagt tgctgaatgg aaaaagatac    2640
ttgcttgtct tagatgatgt ttggaatgaa gatcaacaga agtgggctaa tttaagagca    2700
gtcttgaagg ttggagcaag tggtgcttct gttctaacca ctactcgtct tgaaaaggtt    2760
ggatcaatta tgggaacatt gcaaccatat gaactgtcaa atctgtctca agaagattgt    2820
tggttgttgt tcatgcaacg tgcatttgga caccaagaag aaataaatcc aaaccttgtg    2880
gcaatcggaa aggagattgt gaaaaaaagt ggtggtgtgc ctctagcagc caaaactctt    2940
ggaggtattt tgtgcttcaa gagagaagaa agagcatggg aacatgtgag agacagtccg    3000
atttggaatt tgcctcaaga tgaaagttct attctgcctg ccctgaggct tagttaccat    3060
caacttccac ttgatttgaa acaatgcttt gcgtattgtg cggtgttccc aaaggatgcc    3120
aaaatggaaa aagaaaagct aatctctctc tggatggcgc atggttttct tttatcaaaa    3180
ggaaacatgg agctagagga tgtgggcgat gaagtatgga agaattata cttgaggtct    3240 tttttccaag agattgaagt taaagatggt aaaacttatt tcaagatgca tgatctcatc    3300
catgatttgg caacatctct gttttcagca aacacatcaa gcagcaatat ccgtgaaata    3360
aataaacaca gttacacaca tatgatgtcc attggtttcg ccgaagtggt gttttttttac    3420 actcttcccc ccttggaaaa gtttatctcg ttaagagtgc ttaatctagg tgattcgaca    3480
tttaataagt taccatcttc cattggagat ctagtacatt taagatactt gaacctgtat    3540
ggcagtggca tgcgtagtct tccaaagcag ttatgcaagc ttcaaaatct gcaaactctt    3600
gatctacaat attgcaccaa gctttgttgt ttgccaaaag aaacaagtaa acttggtagt    3660
ctccgaaatc ttttacttga tggtagccag tcattgactt gtatgccacc aaggatagga    3720
tcattgacat gccttaagac tctaggtcaa tttgttgttg gaaggaagaa aggttatcaa    3780
cttggtgaac taggaaacct aaatctctat ggctcaatta aaatctcgca tcttgagaga    3840
gtgaagaatg ataaggacgc aaaagaagcc aatttatctg caaaagggaa tctgcattct    3900
ttaagcatga gttggaataa cttttggacca catatatatg aatcagaaga agttaaagtg    3960
cttgaagccc tcaaaccaca ctccaatctg acttctttaa aaatctatgg cttcaggaga    4020
atccatctcc cagagtggat gaatcactca gtattgaaaa atattgtctc tattctaatt    4080
agcaacttca gaaactgctc atgcttacca ccctttggtg atctgccttg tctagaaagt    4140
ctagagttac actgggggtc tgcggatgtg gagtatgttg aagaagtgga tattgatgtt    4200
cattctggat tccccacaag aataaggttt ccatccttga ggaaacttga tatatgggac    4260
tttggtagtc tgaaaggatt gctgaaaaag gaaggagaag agcaattccc tgtgcttgaa    4320
gagatgataa ttcacgagtg ccctttttctg acccttttctt ctaatcttag ggctcttact    4380
tccctcagaa tttgctataa taaagtagct acttcattcc cagaagagat gttcaaaaac    4440
cttgcaaatc tcaaatactt gacaatctct cggtgcaata atctcaaaga gctgcctacc    4500
agcttggcta gtctgaatgc tttgaaaagt ctaaaaattc aattgtgttg cgcactagag    4560
agtctccctg aggaagggct ggaaggttta tcttcactca cagagttatt tgttgaacac    4620
tgtaacatgc taaaatgttt accagaggga ttgcagcacc taacaaccct cacaagttta    4680
aaaattcggg gatgtccaca actgatcaag cggtgtgaga agggaatagg agaagactgg    4740
cacaaaattt ctcacattcc taatgtgaat atatatattt aagttatttg ctattgtttc    4800
tttgtttgtg agtcttttttg gttcctgcca ttgtgattgc atgtaatttt tttctagggt    4860 tgtttctttta tgagtctctc tctcattgga tgtaatttct ttttggaaac aaatctgtca    4920
attgatttgt attatacgct ttcagaatct attacttatt tgtaattgtt tctttgtttg    4980
```

-continued

| | |
|---|---|
| taaattgtga gtatcttatt ttatggaatt ttctgatttt attttgaaaa caaatcaatg | 5040 |
| atttgtaaga tccatctgta ttatactccc ttcgtctcat tttatgtgtc acctgtcgga | 5100 |
| tttcgagatt caaacaaatc tatctttgat cgtaaatttt taatagatct tttaaacatt | 5160 |
| ttgaattatc aattattgtg actttagtac t | 5191 |

<210> SEQ ID NO 51
<211> LENGTH: 3260
<212> TYPE: DNA
<213> ORGANISM: Solanum bulbocastanum
<220> FEATURE:
<221> NAME/KEY: misc_feature
<222> LOCATION: (1)..(3260)
<223> OTHER INFORMATION: /note="RGC1-blb"

<400> SEQUENCE: 51

| | |
|---|---|
| atggctgaag ctttccttca agttctgcta gataatctca cttttttcat ccaaggggaa | 60 |
| cttggattgg ttttggttt cgagaaggag tttaaaaaac tttcaagtat gttttcaatg | 120 |
| atccaagctg tgctagaaga tgctcaagag aagcaactga agtacaaggc aataaagaac | 180 |
| tggttacaga aactcaatgt tgctgcatat gaagttgatg acatcttgga tgactgtaaa | 240 |
| actgaggcag caagattcaa gcaggctgta ttggggcgtt atcatccacg gaccatcact | 300 |
| ttctgttaca aggtgggaaa aagaatgaaa gaaatgatgg aaaaactaga tgcaattgca | 360 |
| gaggaacgga ggaattttca tttagatgaa aggattatag agagacaagc tgctagacgg | 420 |
| caaacaggtg ctcatcttaa ttttattta aaacaaataa gtattacaaa ttgcagagaa | 480 |
| acgaaggaat ttatattcat tttattttt ggcaattatc aaagtcattt gtgtttttaa | 540 |
| gctgggggga agtttcaaat atttctcta gtcttaatgt ttgtctcact cactcagcat | 600 |
| gattttctca atccttcact tcaactcccc cctactgtgc aaatatcttc tctattttct | 660 |
| gttgactcct aatgagcttg aatgtaacaa cattcttgtt tggagcaggt tttgttttaa | 720 |
| ctgagccaaa agtttatgga agggaaaaag aggaggatga tagtgaaa atcttgataa | 780 |
| acaatgttag ttattccgaa gaagttccag tactcccaat acttggtatg ggggactag | 840 |
| gaaagacgac tctagcccaa atggtcttca atgatcaaag aattactgag catttcaatc | 900 |
| taaagatatg gttttgtgtc tcagatgatt ttgatgagaa gaggttgatt aaggcaattg | 960 |
| tagaatctat tgaaggaaag tcactgggtg acatggactt ggctcccctc cagaaaaagc | 1020 |
| ttcaggagtt gttgaatgga aaagatact ttcttgtttt ggatgatgtt tggaatgaag | 1080 |
| atcaagaaaa gtgggataat cttagagcag tattgaagat tggagctagt ggtgcttcaa | 1140 |
| ttctaattac tactcgtctt gaaaaaattg gatcaattat gggaactttg caactatatc | 1200 |
| agttatcaaa tttgtctcaa gaagattgtt ggttgttgtt caagcaacgt gcattttgcc | 1260 |
| accaaaccga aacaagtcct aaacttatgg aaatcggaaa ggagattgtg aagaaatgtg | 1320 |
| ggggtgtgcc tctagcagcc aaaactcttg gaggcctttt acgcttcaag agggaagaaa | 1380 |
| gtgaatggga acatgtgaga gatagtgaga tttggaattt acctcaagat gaaaattctg | 1440 |
| ttttgcctgc cctgaggctg agttatcatc atcttccact tgatttgaga caatgtttg | 1500 |
| catattgcgc agtattccca aaggacacca aaatagaaaa ggaatatctc atcgctctct | 1560 |
| ggatggcaca cagttttctt ttatcaaaag gaaacatgga gctagaggat gtgggcaatg | 1620 |
| aagtatggaa tgaattatac ttgaggtctt ttttccaaga gattgaagtt aaatctggta | 1680 |
| aaacttattt caagatgcat gatctcatcc atgatttggc tacatctatg ttttcagcaa | 1740 |

-continued

```
gcgcatcaag cagaagtata cgccaaataa atgtaaaaga tgatgaagat atgatgttca    1800
ttgtaacaaa ttataaagat atgatgtcca ttggtttctc cgaagtggtg tcttcttact    1860
ctccttcgct ctttaaaagg tttgtctcgt taagggtgct taatctaagt aactcagaat    1920
ttgaacagtt accgtcttcc gttggagatc tagtacattt aagatacctt gacctgtctg    1980
gtaataaaat ttgtagtctt ccaaagaggt tgtgcaagct tcaaaatctg cagactcttg    2040
atctatataa ttgccagtca ctttcttgtt tgccgaaaca acaagtaag ctttgtagtc     2100 tccggaatct tgtacttgat cactgtccat tgacttctat gccaccaaga ataggattgt    2160
tgacatgcct taagacacta ggttactttg ttgtaggcga gaggaaaggt tatcaacttg    2220
gtgaactacg aaatttaaac ctccgtggtg caatttcaat cacacatctt gagagagtga    2280
aaaatgatat ggaggcaaaa gaagccaatt tatctgcaaa agcaaatcta cactctttaa    2340
gcatgagttg ggatagacca aacagatatg aatccgaaga agttaaagtg cttgaagccc    2400
tcaaaccaca tcccaatctg aaatatttag aaatcattga cttctgtgga ttctgtctcc    2460
ctgactggat gaatcactca gttttgaaaa atgttgtctc tattctaatt agcggttgtg    2520
aaaactgctc gtgcttacca ccctttggtg agctgccttg tctagaaagt ctggagttac    2580
aagacgggtc tgtggaggtg gagtatgttg aagattctgg attcctgaca agaagaagat    2640
ttccatccct gagaaaactt catataggtg gcttttgtaa tctgaaagga ttgcagagaa    2700
tgaaaggagc agagcaattc cccgtgcttg aagagatgaa gatttcggat tgccctatgt    2760 ttgttttttcc gacccttttct tctgtcaaga aattagaaat ttgggggag gcagatgcag     2820 gaggtttgag ctccatatct aatctcagca ctcttacatc cctcaagatt ttcagtaacc    2880
acacagtgac ttcactactg gaagagatgt tcaaaaacct tgaaaatctc atatacttga    2940
gtgtctcttt cttggagaat ctcaaagagc tgcctaccag cctggctagt ctcaacaatt    3000
tgaagtgtct ggatattcgt tattgttacg cactagagag tctccccgag aagggctgg    3060 aaggtttatc ttcactcaca gagttatttg ttgaacactg taacatgcta aaatgtttac    3120
cagagggatt gcagcaccta acaaccctca caagtttaaa aattcgggga tgtccacaac    3180
tgatcaagcg gtgtgagaag ggaataggag aagactggca caaaatttct cacattccta    3240
atgtgaatat atatatttaa                                               3260
```

<210> SEQ ID NO 52
<211> LENGTH: 3971
<212> TYPE: DNA
<213> ORGANISM: Solanum bulbocastanum
<220> FEATURE:
<221> NAME/KEY: misc_feature
<222> LOCATION: (1)..(3971)
<223> OTHER INFORMATION: /note="RGC3-blb"

<400> SEQUENCE: 52

```
atggctgaag ctttcattca agttgtgcta gacaatctca cttctttcct caaaggggaa      60
cttgtattgc ttttcggttt tcaagatgag ttccaaaggc tttcaagcat gttttctaca    120
atccaagccg tccttgaaga tgctcaagag aagcaactca cgacaagcc tctagaaaat     180 tggttgcaaa aactcaatgc tgctacatat gaagtcgatg acatcttgga tgaatataaa    240
actaaggcca aagattctt gcagtctgaa tatggccgtt atcatccaaa ggttatccct     300
ttccgtcaca aggttgggaa aaggatggac caagtgatga aaaaactgaa tgcaattgct    360
gaggaacgaa agaattttca tttgcaagaa aagattatag agacaagc tgctacacgg     420 gaaacaggta ctcatcttaa attagtatta caacttagtt tatattcatt tgttttgggc    480
```

```
aatgatcaaa ttatgtaaag gtcaaatata ctcatgtact actgaaaata gtttaaatat    540
acctctagtt atactattag tacgaacata ctcctcccat atactttgga acaaatattc    600
ccttaacgaa ataagacacg tgaaaagttc agattcaaat tatccaccct caattttaag    660
atctgatttc tttaggaaac cactcatctc ctccgttttg agttcttaac gaagcagctc    720
agagaaaaga ggttttcttc tgttctgttt ctgctgcatt tgtgtcttaa tccaataaca    780
aacaatacaa attaatatta tgttcacgat gagggtagtc tttctagcta gacatgaact    840
gagtgtaaat tttgttttaa ggaagaaaaa gaaatgatta ggctggattt ctttcagagt    900
ggaatatagg gggataaagt tggagcatag agttccatcg tttatttctt tccttaaagt    960
aacaagttca acaaaatgat atcaaggtac ggtaatggaa aattattaga cacgtctaaa   1020
ctacaaaaat ggaatagaaa cttaaattat cagtgacaat atcatccttt aataaagcta   1080
ccaaatttaa atcatgatac agagaagaaa ccaaaaaaat tagggggtgaa ttatttgatt   1140
ctatgcttat cacatgtctt cccatcaaca tcaaggaaa aattgtgcca aagtataaac    1200
ggtgcggtat atttggattg aaagtaaaac aggaggatac atttggacta aaagtataac   1260
aataagtata tttgatcatt ttatgtatca aattcatgtg gttttttgggg agaagggaag   1320
tttcaatgtt ttcaatctgc tcctcatctc atccatatct ctttattgtg caaacccctt   1380
ctctatttaa ctattttctg ccgactccta atgagcttga atgtaacaat attctcatct   1440
ggacattgct tgcaccaggt tctgtgttaa ctgaaccaca agtttatgga agggacaaag   1500
aaaaagatga gatagtgaaa atcctaataa acaatgttag tgatgcccaa aaactctcag   1560
tcctcccaat acttggtatg gggggactag gaaagacaac tctttcccaa atggtcttca   1620
atgatcagag agtaactgag cgtttctatc ccaaaatatg gatttgcgtc tcggatgatt   1680
ttgatgagaa gaggttgata aaggcaatag tagaatctat tgaagggaag tccctcagtg   1740
acatggactt ggctccactt caaaagaagc ttcaagagtt gctgaatgga aaagatact    1800
tccttgtctt agatgatgtt tggaatgaag atcaacataa gtgggctaat ttaagagcag   1860
tcttgaaggt tggagcaagt ggtgcatttg ttctaactac tactcgtctt gaaaaggttg   1920
gatcaattat gggaacattg caaccatatg aattgtcaaa tctgtctcca gaggattgtt   1980
ggttttttgtt catgcagcgt gcatttggac accaagaaga aataaatcca aaccttgtgg   2040
caatcggaaa ggagattgtg aaaaaatgtg gtggtgtgcc tctagcagcc aagactcttg   2100
gaggtatttt gcgcttcaag agagaagaaa gagaatggga acatgtgaga gacagtccga   2160
tttggaattt gcctcaagat gaaagttcta ttctgcctgc cctgaggctt agttaccatc   2220
atcttccact tgatttgaga caatgctttg tgtattgtgc ggtattccca aaggacacca   2280
aaatggcaaa ggaaaatctt atcgcttttt ggatggcaca tggttttctt ttatcgaaag   2340
gaaatttgga gctagaggat gtaggtaatg aagtatggaa tgaattatac ttgaggtctt   2400
tcttccaaga gattgaagtt gaatctggta aaacttattt caagatgcat gacctcatcc   2460
atgatttggc tacatctctg ttttcagcaa acacatcaag cagcaatatt cgtgaaataa   2520
atgctaatta tgatggatat atgatgtcga ttggttttgc tgaagtggta tcttcttact   2580
ctccttcact cttgcaaaag tttgtctcat taagggtgct taatctaaga aactcgaacc   2640
taaatcaatt accatcttcc attggagatc tagtacattt aagatacctg gacttgtctg   2700
gcaattttag aattcgtaat cttccaaaga gattatgcag gcttcaaaat ctgcagactc   2760
ttgatctaca ttattgcgac tctctttctt gtttgccaaa acaaacaagt aaacttggta   2820
```

```
gtctccgaaa tcttttactt gatggctgtt cattgacgtc aacgccacca aggataggat    2880
tgttgacatg ccttaagtct ctaagttgct ttgttattgg caagagaaaa ggttatcaac    2940
ttggtgaact aaaaaaccta aatctctatg gctcaatttc aatcacaaaa cttgacagag    3000
tgaagaaaga tagcgatgca aaagaagcta atttatctgc taaagcaaat ctgcactctt    3060
tatgcctgag ttgggacctt gatggaaaac atagatatga ttcagaagtt cttgaagccc    3120
tcaaaccaca ctccaatctg aaatatttag aaatcaatgg cttcggagga atccgtctcc    3180
cagattggat gaatcaatca gttttgaaaa atgttgtctc tattagaatt agaggttgtg    3240
aaaactgctc atgcttacca cccttggtg agctgccttg tctagaaagt ctagagttac    3300
acaccgggtc agcagatgtg gagtatgttg aagataatgt tcatcctgga aggtttccat    3360
ccttgaggaa acttgttata tgggacttta gtaatctaaa aggattgctg aaaaaggaag    3420
gagaaaagca attccctgtg cttgaagaga tgacatttta ctggtgccct atgtttgtta    3480
ttccgaccct ttcttctgtc aagacattga agttattgc gacagatgca acagttttga    3540
ggtccatatc taatcttagg gctcttactt cccttgacat tagcaataac gtagaagcta    3600
cttcactccc agaagagatg ttcaaaagcc ttgcaaatct caaatacttg aatatctctt    3660
tctttaggaa tctcaaagag ttgcctacca gcctggctag tctcaatgct ttgaagagtc    3720
tcaaatttga attttgtaac gcactagaga gtctcccaga ggaaggggtg aaaggtttaa    3780
cttcactcac cgagttgtct gtcagtaact gtatgatgct aaaatgttta ccggagggat    3840
tgcagcacct aacagccctc acaactttaa caattactca atgtccaata gtattcaagc    3900
ggtgtgagag aggaatagga gaagactggc acaaaattgc tcacattcca tatttgactc    3960
tatatgagtg a                                                          3971
```

<210> SEQ ID NO 53
<211> LENGTH: 3899
<212> TYPE: DNA
<213> ORGANISM: Solanum bulbocastanum
<220> FEATURE:
<221> NAME/KEY: misc_feature
<222> LOCATION: (1)..(3899)
<223> OTHER INFORMATION: /note="RGC4-blb"

<400> SEQUENCE: 53

```
atggcggaag cttttcttca agttctgcta gaaaatctca cttctttcat cggagataaa      60
cttgtattga ttttcggttt cgaaaaggaa tgtgaaaagc tgtcgagtgt gtttccaca     120 attcaagctg tgcttcaaga tgctcaggag aagcaattga aggacaaggc aattgagaat    180
tggttgcaga aactcaattc tgctgcctat gaagttgatg atatattggg cgaatgtaaa    240
aatgaggcaa taagatttga gcagtctcga ttagggtttt tcacccagg gattatcaat    300 ttccgtcaca aaattgggag aaggatgaaa gagataatgg agaaactaga tgcaatatct    360
gaggaaagaa ggaagtttca tttccttgaa aaaattacag agagacaagc tgccgctgct    420
acgcgtgaaa caggtgtgag tactgagtaa ttgtagctta gttaatattc aatttgttac    480
cacatcatgt gttcaccgtg atctctacag taggatggca atgggctgg gcgaggttgg    540 aggtgtgcag gtgtgtggcg caaccccaac tttgagtcta cataagtagg tacttaaatt    600
tgtatagagt tgaacaagta caaacgcctc tacttggtg tccttatgcg tattatgtca    660
cttaggatgc atgtgtctac ttgttcaact ttatatgagt ttaagttcta cttgtgcaca    720
cccaaagttg gagcgcgtag atgtcagttg ataccaagtt aaaaaggcat atttatgaat    780
tatgccttta aattatgatt caattttgta tcagtctgtc caaaatatgt tctagtgaaa    840
```

-continued

```
gtgttaaact tagtctggat ctgctattga aagtgaattt ttgtggcact aaacaatgca    900
atgggtctgg attcattttt gcattaactt ttgtttagac gattttcttt atcgaatttt    960
actgtctaaa atgaaaaag caaagaaata agaagtatac agaggctgac ttcttcatag   1020
tatctatcat ataaaaaaaa gcattgatta ctaggatatg ggttctttta aattacaaat   1080
ttgtgagtta aaacagttct gttgggaagg atttagatac acgtggatag tatctagaag   1140
ttttttaaat aaaaaattag caaattatgc gggctgggc gggttgaaaa cagcaaactt    1200
tgcaaggctt ggcgggtcga aatctttgca agtttgtgtg ggtttgccct gcaccaccca   1260
atctgccatt cctgtctaaa tgtttgtttt gtctataatt cttgctgact cattctaatg   1320
agctcaattg taacaaattc tttgtgtcca cattacttgg aacaggtttt gtgttaactg   1380
aaccaaaagt ctacggaagg acaaagagg aggatgagat agtgaaaatt ctgataaaca    1440
atgttaatgt tgccgaagaa cttccagtct tccctataat tggtatgggg ggactaggaa   1500
agacgacact tgcccaaatg atcttcaacg atgagagagt aactaagcat ttcaatccca   1560
aaatatgggt ttgtgtctca gatgattttg atgagaagag gttaattaag acaattatag   1620
gaaatattga aagaagttct cctcatgttg aggacttggc ttcatttcag aagaagctcc   1680
aggagttatt gaatgaaaaa cgatacttgc ttgtcttaga tgatgtttgg aatgatgatc   1740
tagaaaagtg ggctaagtta agagcagtct taactgttgg agcaagaggt gcttctattc   1800
tagctactac tcgtcttgaa aaggttggat caattatggg aacgttgcaa ccatatcatt   1860
tgtcaaattt gtctccacat gatagtttac ttttgtttat gcaacgcgca tttgggcaac   1920
aaaaagaagc aaatcctaat ctagtggcca ttggaaagga gattgtgaag aaatgtggtg   1980
gtgtgccttt agcagccaag actcttggtg gtcttttacg cttcaagaga gaagagagtg   2040
aatgggaaca tgtgagagat aatgagattt ggagtctgcc tcaagatgaa agttctattt   2100
tgcctgctct aagactgagt tatcatcacc ttccacttga tttgagacaa tgctttgcgt   2160
attgtgcagt attcccaaag gacaccaaaa tgataaagga aaatctcatt actctctgga   2220
tggcgcatgg ttttctttta tcaaagggaa acttggagct agaggatgtg ggtaatgaag   2280
tatggaatga attatacttg aggtctttct tccaagaaat tgaagctaaa tcgggtaata   2340
cttatttcaa gatacatgat ctaatccatg atttggctac atctctgttt tcggcaagcg   2400
catcatgcgg caatatccgc gaaataaatg tcaaagatta taagcataca gtgtccattg   2460
gtttcgctgc agtggtgtct tcttactctc cttcgctctt gaaaaagttt gtctcgttaa   2520
gggtgcttaa tctaagttac tcaaaacttg agcaattacc gtcttccatt ggagatctat   2580
tacatttaag atacctggac ctgtcttgca ataacttccg tagtcttcca gagaggttgt   2640
gcaagcttca aaatcttcag actcttgatg tacataattg ctactcactt aattgtttgc   2700
caaaacaaac aagtaaactt agtagtctcc gacatcttgt tgttgatggc tgtccattga   2760
cttctactcc accaaggata ggattgttga catgccttaa gactctaggt ttctttattg   2820
tgggaagcaa gaaaggttat caacttggtg aactgaaaaa cctaaatctc tgcggctcaa   2880
tttcaatcac acaccttgag agagtgaaga acgatacgga tgcagaagcc aatttatctg   2940
caaaagcaaa tctgcaatct ttaagcatga gttgggataa cgatggacca aacagatatg   3000
aatccaaaga agttaaagtg cttgaagcac tcaaaccaca ccccaatctg aaatatttag   3060
agatcattgc cttcggagga ttccgttttc caagctggat aaatcactca gttttggaga   3120
aggtcatctc tgttagaatt aaaagctgca aaaactgctt gtgcttacca cccttggggg   3180
```

```
agcttccttg tctagaaaat ctagagttac aaaacggatc tgcggaggtg gagtatgttg    3240
aagaggatga tgtccattct agattctcca caagaagaag ctttccatcc ctgaaaaaac    3300
ttcgtatatg gttctttcgc agtttgaaag ggctgatgaa agaggaagga gaagagaaat    3360
tccccatgct tgaagagatg gcgattttat attgccctct gtttgttttt ccaacccttt    3420
cttctgtcaa gaaattagaa gttcacggca acacaaacac tagaggtttg agctccatat    3480
ctaatcttag cactcttact tccctccgca ttggtgctaa ctacagagcg acttcactcc    3540
cagaagagat gttcacaagt cttacaaatc tcgaattctt gagtttcttt gacttcaaga    3600
atctcaaaga tctgcctacc agcctgacta gtctcaatgc tttgaagcgt ctccaaattg    3660
aaagttgtga ctcactagag agtttccctg aacaagggct agaaggttta acttcactca    3720
cacagttgtt tgttaaatac tgtaagatgc taaaatgttt acccgaggga ttgcagcacc    3780
taacagccct cacaaattta ggagtttctg gttgtccaga agtggaaaag cgctgtgata    3840
aggaaatagg agaagactgg cacaaaattg ctcacattcc aaatctggat attcattag    3899
```

<210> SEQ ID NO 54
<211> LENGTH: 970
<212> TYPE: PRT
<213> ORGANISM: Artificial Sequence
<220> FEATURE:
<223> OTHER INFORMATION: Description of Artificial Sequence: deduced
      Rpi-blb protein sequence domain A, B and C
<220> FEATURE:
<221> NAME/KEY: SITE
<222> LOCATION: (1)..(970)

<400> SEQUENCE: 54

```
Met Ala Glu Ala Phe Ile Gln Val Leu Leu Asp Asn Leu Thr Ser Phe
 1               5                  10                  15

Leu Lys Gly Glu Leu Val Leu Leu Phe Gly Phe Gln Asp Glu Phe Gln
            20                  25                  30

Arg Leu Ser Ser Met Phe Ser Thr Ile Gln Ala Val Leu Glu Asp Ala
        35                  40                  45

Gln Glu Lys Gln Leu Asn Asn Lys Pro Leu Glu Asn Trp Leu Gln Lys
    50                  55                  60

Leu Asn Ala Ala Thr Tyr Glu Val Asp Asp Ile Leu Asp Glu Tyr Lys
65                  70                  75                  80

Thr Lys Ala Thr Arg Phe Ser Gln Ser Glu Tyr Gly Arg Tyr His Pro
                85                  90                  95

Lys Val Ile Pro Phe Arg His Lys Val Gly Lys Arg Met Asp Gln Val
            100                 105                 110

Met Lys Lys Leu Lys Ala Ile Ala Glu Glu Arg Lys Asn Phe His Leu
        115                 120                 125

His Glu Lys Ile Val Glu Arg Gln Ala Val Arg Glu Thr Gly Ser
    130                 135                 140

Val Leu Thr Glu Pro Gln Val Tyr Gly Arg Asp Lys Glu Lys Asp Glu
145                 150                 155                 160

Ile Val Lys Ile Leu Ile Asn Asn Val Ser Asp Ala Gln His Leu Ser
                165                 170                 175

Val Leu Pro Ile Leu Gly Met Gly Gly Leu Gly Lys Thr Thr Leu Ala
            180                 185                 190

Gln Met Val Phe Asn Asp Gln Arg Val Thr Glu His Phe His Ser Lys
        195                 200                 205

Ile Trp Ile Cys Val Ser Glu Asp Phe Asp Glu Lys Arg Leu Ile Lys
    210                 215                 220
```

-continued

```
Ala Ile Val Glu Ser Ile Glu Gly Arg Pro Leu Leu Gly Glu Met Asp
225                 230                 235                 240

Leu Ala Pro Leu Gln Lys Lys Leu Gln Glu Leu Leu Asn Gly Lys Arg
            245                 250                 255

Tyr Leu Leu Val Leu Asp Asp Val Trp Asn Glu Asp Gln Gln Lys Trp
            260                 265                 270

Ala Asn Leu Arg Ala Val Leu Lys Val Gly Ala Ser Gly Ala Ser Val
            275                 280                 285

Leu Thr Thr Thr Arg Leu Glu Lys Val Gly Ser Ile Met Gly Thr Leu
            290                 295                 300

Gln Pro Tyr Glu Leu Ser Asn Leu Ser Gln Glu Asp Cys Trp Leu Leu
305                 310                 315                 320

Phe Met Gln Arg Ala Phe Gly His Gln Glu Ile Asn Pro Asn Leu
            325                 330                 335

Val Ala Ile Gly Lys Glu Ile Val Lys Lys Ser Gly Gly Val Pro Leu
            340                 345                 350

Ala Ala Lys Thr Leu Gly Gly Ile Leu Cys Phe Lys Arg Glu Glu Arg
            355                 360                 365

Ala Trp Glu His Val Arg Asp Ser Pro Ile Trp Asn Leu Pro Gln Asp
370                 375                 380

Glu Ser Ser Ile Leu Pro Ala Leu Arg Leu Ser Tyr His Gln Leu Pro
385                 390                 395                 400

Leu Asp Leu Lys Gln Cys Phe Ala Tyr Cys Ala Val Phe Pro Lys Asp
            405                 410                 415

Ala Lys Met Glu Lys Glu Lys Leu Ile Ser Leu Trp Met Ala His Gly
            420                 425                 430

Phe Leu Leu Ser Lys Gly Asn Met Glu Leu Glu Asp Val Gly Asp Glu
            435                 440                 445

Val Trp Lys Glu Leu Tyr Leu Arg Ser Phe Gln Glu Ile Glu Val
450                 455                 460

Lys Asp Gly Lys Thr Tyr Phe Lys Met His Asp Leu Ile His Asp Leu
465                 470                 475                 480

Ala Thr Ser Leu Phe Ser Ala Asn Thr Ser Ser Asn Ile Arg Glu
            485                 490                 495

Ile Asn Lys His Ser Tyr Thr His Met Met Ser Ile Gly Phe Ala Glu
            500                 505                 510

Val Val Phe Phe Tyr Thr Leu Pro Pro Leu Glu Lys Phe Ile Ser Leu
            515                 520                 525

Arg Val Leu Asn Leu Gly Asp Ser Thr Phe Asn Lys Leu Pro Ser Ser
530                 535                 540

Ile Gly Asp Leu Val His Leu Arg Tyr Leu Asn Leu Tyr Gly Ser Gly
545                 550                 555                 560

Met Arg Ser Leu Pro Lys Gln Leu Cys Lys Leu Gln Asn Leu Gln Thr
            565                 570                 575

Leu Asp Leu Gln Tyr Cys Thr Lys Leu Cys Cys Leu Pro Lys Glu Thr
            580                 585                 590

Ser Lys Leu Gly Ser Leu Arg Asn Leu Leu Leu Asp Gly Ser Gln Ser
            595                 600                 605

Leu Thr Cys Met Pro Pro Arg Ile Gly Ser Leu Thr Cys Leu Lys Thr
            610                 615                 620

Leu Gly Gln Phe Val Val Gly Arg Lys Lys Gly Tyr Gln Leu Gly Glu
625                 630                 635                 640
```

```
Leu Gly Asn Leu Asn Leu Tyr Gly Ser Ile Lys Ile Ser His Leu Glu
                645                 650                 655

Arg Val Lys Asn Asp Lys Asp Ala Lys Glu Ala Asn Leu Ser Ala Lys
            660                 665                 670

Gly Asn Leu His Ser Leu Ser Met Ser Trp Asn Asn Phe Gly Pro His
        675                 680                 685

Ile Tyr Glu Ser Glu Glu Val Lys Val Leu Glu Ala Leu Lys Pro His
    690                 695                 700

Ser Asn Leu Thr Ser Leu Lys Ile Tyr Gly Phe Arg Gly Ile His Leu
705                 710                 715                 720

Pro Glu Trp Met Asn His Ser Val Leu Lys Asn Ile Val Ser Ile Leu
                725                 730                 735

Ile Ser Asn Phe Arg Asn Cys Ser Cys Leu Pro Pro Phe Gly Asp Leu
            740                 745                 750

Pro Cys Leu Glu Ser Leu Glu Leu His Trp Gly Ser Ala Asp Val Glu
        755                 760                 765

Tyr Val Glu Glu Val Asp Ile Asp Val His Ser Gly Phe Pro Thr Arg
    770                 775                 780

Ile Arg Phe Pro Ser Leu Arg Lys Leu Asp Ile Trp Asp Phe Gly Ser
785                 790                 795                 800

Leu Lys Gly Leu Leu Lys Lys Glu Gly Glu Glu Gln Phe Pro Val Leu
                805                 810                 815

Glu Glu Met Ile Ile His Glu Cys Pro Phe Leu Thr Leu Ser Ser Asn
            820                 825                 830

Leu Arg Ala Leu Thr Ser Leu Arg Ile Cys Tyr Asn Lys Val Ala Thr
        835                 840                 845

Ser Phe Pro Glu Met Phe Lys Asn Leu Ala Asn Leu Lys Tyr Leu
    850                 855                 860

Thr Ile Ser Arg Cys Asn Asn Leu Lys Glu Leu Pro Thr Ser Leu Ala
865                 870                 875                 880

Ser Leu Asn Ala Leu Lys Ser Leu Lys Ile Gln Leu Cys Cys Ala Leu
                885                 890                 895

Glu Ser Leu Pro Glu Glu Gly Leu Glu Gly Leu Ser Ser Leu Thr Glu
            900                 905                 910

Leu Phe Val Glu His Cys Asn Met Leu Lys Cys Leu Pro Glu Gly Leu
        915                 920                 925

Gln His Leu Thr Thr Leu Thr Ser Leu Lys Ile Arg Gly Cys Pro Gln
    930                 935                 940

Leu Ile Lys Arg Cys Glu Lys Gly Ile Gly Glu Asp Trp His Lys Ile
945                 950                 955                 960

Ser His Ile Pro Asn Val Asn Ile Tyr Ile
                965                 970

<210> SEQ ID NO 55
<211> LENGTH: 979
<212> TYPE: PRT
<213> ORGANISM: Artificial Sequence
<220> FEATURE:
<223> OTHER INFORMATION: Description of Artificial Sequence: alignment
      RGC3-blb
<220> FEATURE:
<221> NAME/KEY: SITE
<222> LOCATION: (1)..(979)

<400> SEQUENCE: 55

Met Ala Glu Ala Phe Ile Gln Val Val Leu Asp Asn Leu Thr Ser Phe
1               5                   10                  15
```

```
Leu Lys Gly Glu Leu Val Leu Leu Phe Gly Phe Gln Asp Glu Phe Gln
                20                  25                  30

Arg Leu Ser Ser Met Phe Ser Thr Ile Gln Ala Val Leu Glu Asp Ala
            35                  40                  45

Gln Glu Lys Gln Leu Asn Asp Lys Pro Leu Glu Asn Trp Leu Gln Lys
        50                  55                  60

Leu Asn Ala Ala Thr Tyr Glu Val Asp Ile Leu Asp Glu Tyr Lys
 65                  70                  75                  80

Thr Lys Ala Thr Arg Phe Leu Gln Ser Glu Tyr Gly Arg Tyr His Pro
                85                  90                  95

Lys Val Ile Pro Phe Arg His Lys Val Gly Lys Arg Met Asp Gln Val
            100                 105                 110

Met Lys Lys Leu Asn Ala Ile Ala Glu Glu Arg Lys Asn Phe His Leu
        115                 120                 125

Gln Glu Lys Ile Ile Glu Arg Gln Ala Ala Thr Arg Glu Thr Gly Ser
    130                 135                 140

Val Leu Thr Glu Pro Gln Val Tyr Gly Arg Asp Lys Glu Lys Asp Glu
145                 150                 155                 160

Ile Val Lys Ile Leu Ile Asn Asn Val Ser Asp Ala Gln Lys Leu Ser
                165                 170                 175

Val Leu Pro Ile Leu Gly Met Gly Gly Leu Gly Lys Thr Thr Leu Ser
            180                 185                 190

Gln Met Val Phe Asn Asp Gln Arg Val Thr Glu Arg Phe Tyr Pro Lys
        195                 200                 205

Ile Trp Ile Cys Val Ser Asp Asp Phe Asp Glu Lys Arg Leu Ile Lys
    210                 215                 220

Ala Ile Val Glu Ser Ile Glu Gly Lys Ser Leu Ser Asp Met Asp Leu
225                 230                 235                 240

Ala Pro Leu Gln Lys Lys Leu Gln Glu Leu Leu Asn Gly Lys Arg Tyr
                245                 250                 255

Phe Leu Val Leu Asp Asp Val Trp Asn Glu Asp Gln His Lys Trp Ala
            260                 265                 270

Asn Leu Arg Ala Val Leu Lys Val Gly Ala Ser Gly Ala Phe Val Leu
        275                 280                 285

Thr Thr Thr Arg Leu Glu Lys Val Gly Ser Ile Met Gly Thr Leu Gln
    290                 295                 300

Pro Tyr Glu Leu Ser Asn Leu Ser Pro Glu Asp Cys Trp Phe Leu Phe
305                 310                 315                 320

Met Gln Arg Ala Phe Gly His Gln Glu Glu Ile Asn Pro Asn Leu Val
                325                 330                 335

Ala Ile Gly Lys Glu Ile Val Lys Lys Cys Gly Gly Val Pro Leu Ala
            340                 345                 350

Ala Lys Thr Leu Gly Gly Ile Leu Arg Phe Lys Arg Glu Glu Arg Glu
        355                 360                 365

Trp Glu His Val Arg Asp Ser Pro Ile Trp Asn Leu Pro Gln Asp Glu
    370                 375                 380

Ser Ser Ile Leu Pro Ala Leu Arg Leu Ser Tyr His His Leu Pro Leu
385                 390                 395                 400

Asp Leu Asp Gln Cys Phe Val Tyr Cys Ala Val Phe Pro Lys Asp Thr
                405                 410                 415

Lys Met Ala Lys Glu Asn Leu Ile Ala Phe Trp Met Ala His Gly Phe
            420                 425                 430
```

```
Leu Leu Ser Lys Gly Asn Leu Glu Leu Glu Asp Val Gly Asn Glu Val
        435                 440                 445

Trp Asn Glu Leu Tyr Leu Arg Ser Phe Phe Gln Glu Ile Glu Val Glu
    450                 455                 460

Ser Gly Lys Thr Tyr Phe Lys Met His Asp Leu Ile His Asp Leu Ala
465                 470                 475                 480

Thr Ser Leu Phe Ser Ala Asn Thr Ser Ser Asn Ile Arg Glu Ile
                485                 490                 495

Asn Ala Asn Tyr Asp Gly Tyr Met Met Ser Ile Gly Phe Ala Glu Val
            500                 505                 510

Val Ser Ser Tyr Ser Pro Ser Leu Leu Gln Lys Phe Val Ser Leu Arg
        515                 520                 525

Val Leu Asn Leu Arg Asn Ser Asn Leu Asn Gln Leu Pro Ser Ser Ile
    530                 535                 540

Gly Asp Leu Val His Leu Arg Tyr Leu Asp Leu Ser Gly Asn Phe Arg
545                 550                 555                 560

Ile Arg Asn Leu Pro Lys Arg Leu Cys Lys Leu Gln Asn Leu Gln Thr
                565                 570                 575

Leu Asp Leu His Tyr Cys Asp Ser Leu Ser Cys Leu Pro Lys Gln Thr
            580                 585                 590

Ser Lys Leu Gly Ser Leu Arg Asn Leu Leu Asp Gly Cys Ser Leu
        595                 600                 605

Thr Ser Thr Pro Pro Arg Ile Gly Leu Leu Thr Cys Leu Lys Ser Leu
    610                 615                 620

Ser Cys Phe Val Ile Gly Lys Arg Lys Gly Tyr Gln Leu Gly Glu Leu
625                 630                 635                 640

Lys Asn Leu Asn Leu Tyr Gly Ser Ile Ser Ile Thr Lys Leu Asp Arg
                645                 650                 655

Val Lys Lys Asp Ser Asp Ala Lys Glu Ala Asn Leu Ser Ala Lys Ala
            660                 665                 670

Asn Leu His Ser Leu Cys Leu Ser Trp Asp Leu Asp Gly Lys His Arg
        675                 680                 685

Tyr Asp Ser Glu Val Leu Glu Ala Leu Lys Pro His Ser Asn Leu Lys
    690                 695                 700

Tyr Leu Glu Ile Asn Gly Phe Gly Gly Ile Arg Leu Pro Asp Trp Met
705                 710                 715                 720

Asn Gln Ser Val Leu Lys Asn Val Val Ser Ile Arg Ile Arg Gly Cys
                725                 730                 735

Glu Asn Cys Ser Cys Leu Pro Pro Phe Gly Glu Leu Pro Cys Leu Glu
            740                 745                 750

Ser Leu Glu Leu His Thr Gly Ser Ala Asp Val Glu Tyr Val Glu Asp
        755                 760                 765

Asn Val His Pro Gly Arg Phe Pro Ser Leu Arg Lys Leu Val Ile Trp
    770                 775                 780

Asp Phe Ser Asn Leu Lys Gly Leu Leu Lys Glu Gly Glu Glu Gln
785                 790                 795                 800

Phe Pro Val Leu Glu Glu Met Thr Phe Tyr Trp Cys Pro Met Phe Val
                805                 810                 815

Ile Pro Thr Leu Ser Ser Val Lys Thr Leu Lys Val Ile Ala Thr Asp
            820                 825                 830

Ala Thr Val Leu Arg Ser Ile Ser Asn Leu Arg Ala Leu Thr Ser Leu
        835                 840                 845

Asp Ile Ser Asn Asn Val Glu Ala Thr Ser Leu Pro Glu Glu Met Phe
```

-continued

```
              850                 855                 860
Lys Ser Leu Ala Asn Leu Lys Tyr Leu Asn Ile Ser Phe Phe Arg Asn
865                 870                 875                 880

Leu Lys Glu Leu Pro Thr Ser Leu Ala Ser Leu Asn Ala Leu Lys Ser
                    885                 890                 895

Leu Lys Phe Glu Phe Cys Asn Ala Leu Glu Ser Leu Pro Ala Glu Gly
                900                 905                 910

Val Lys Gly Leu Thr Ser Leu Thr Glu Leu Ser Val Ser Asn Cys Met
                915                 920                 925

Met Leu Lys Cys Leu Pro Glu Gly Leu Gln His Leu Thr Ala Leu Thr
            930                 935                 940

Thr Leu Thr Ile Thr Gln Cys Pro Ile Val Phe Lys Arg Cys Glu Arg
945                 950                 955                 960

Gly Ile Gly Glu Asp Trp His Lys Ile Ala His Ile Pro Tyr Leu Thr
                965                 970                 975

Leu Tyr Glu

<210> SEQ ID NO 56
<211> LENGTH: 992
<212> TYPE: PRT
<213> ORGANISM: Artificial Sequence
<220> FEATURE:
<223> OTHER INFORMATION: Description of Artificial Sequence: alignment
      RGC1-b1b
<220> FEATURE:
<221> NAME/KEY: SITE
<222> LOCATION: (1)..(992)

<400> SEQUENCE: 56

Met Ala Glu Ala Phe Leu Gln Val Leu Leu Asp Asn Leu Thr Phe Phe
1               5                   10                  15

Ile Gln Gly Glu Leu Gly Leu Val Phe Gly Phe Glu Lys Glu Phe Lys
                20                  25                  30

Lys Leu Ser Ser Met Phe Ser Met Ile Gln Ala Val Leu Glu Asp Ala
            35                  40                  45

Gln Glu Lys Gln Leu Lys Tyr Lys Ala Ile Lys Asn Trp Leu Gln Lys
        50                  55                  60

Leu Asn Val Ala Ala Tyr Glu Val Asp Asp Ile Leu Asp Asp Cys Lys
65                  70                  75                  80

Thr Glu Ala Ala Arg Phe Lys Gln Ala Val Leu Gly Arg Tyr His Pro
                85                  90                  95

Arg Thr Ile Thr Phe Cys Tyr Lys Val Gly Lys Arg Met Lys Glu Met
                100                 105                 110

Met Glu Lys Leu Asp Ala Ile Ala Glu Glu Arg Arg Asn Phe His Leu
            115                 120                 125

Asp Glu Arg Ile Ile Glu Arg Gln Ala Ala Arg Gln Thr Gly Phe Phe
        130                 135                 140

Val Leu Thr Glu Pro Lys Val Tyr Gly Arg Glu Lys Glu Asp Glu
145                 150                 155                 160

Ile Val Lys Ile Leu Ile Asn Asn Val Ser Tyr Ser Glu Glu Val Pro
                165                 170                 175

Val Leu Pro Ile Leu Gly Met Gly Gly Leu Gly Lys Thr Thr Leu Ala
                180                 185                 190

Gln Met Val Phe Asn Asp Gln Arg Ile Thr Glu His Phe Asn Leu Lys
            195                 200                 205

Ile Trp Val Cys Val Ser Asp Asp Phe Asp Glu Lys Arg Leu Ile Lys
```

-continued

```
            210                 215                 220
Ala Ile Val Glu Ser Ile Glu Gly Lys Ser Leu Gly Asp Met Asp Leu
225                 230                 235                 240

Ala Pro Leu Gln Lys Lys Leu Gln Glu Leu Leu Asn Gly Lys Arg Tyr
                245                 250                 255

Phe Leu Val Leu Asp Asp Val Trp Asn Glu Asp Gln Glu Lys Trp Asp
                260                 265                 270

Asn Leu Arg Ala Val Leu Lys Ile Gly Ala Ser Gly Ala Ser Ile Leu
                275                 280                 285

Ile Thr Thr Arg Leu Glu Lys Ile Gly Ser Ile Met Gly Thr Leu Gln
                290                 295                 300

Leu Tyr Gln Leu Ser Asn Leu Ser Gln Glu Asp Cys Trp Leu Leu Phe
305                 310                 315                 320

Lys Gln Arg Ala Phe Cys His Gln Thr Glu Thr Ser Pro Lys Leu Met
                325                 330                 335

Glu Ile Gly Lys Glu Ile Val Lys Lys Cys Gly Gly Val Pro Leu Ala
                340                 345                 350

Ala Lys Thr Leu Gly Gly Leu Leu Arg Phe Lys Arg Glu Glu Ser Glu
                355                 360                 365

Trp Glu His Val Arg Asp Ser Glu Ile Trp Asn Leu Pro Gln Asp Glu
                370                 375                 380

Asn Ser Val Leu Pro Ala Leu Arg Leu Ser Tyr His His Leu Pro Leu
385                 390                 395                 400

Asp Leu Arg Gln Cys Phe Ala Tyr Cys Ala Val Phe Pro Lys Asp Thr
                405                 410                 415

Lys Ile Glu Lys Glu Tyr Leu Ile Ala Leu Trp Met Ala His Ser Phe
                420                 425                 430

Leu Leu Ser Lys Gly Asn Met Glu Leu Glu Asp Val Gly Asn Glu Val
                435                 440                 445

Trp Asn Glu Leu Tyr Leu Arg Ser Phe Phe Gln Glu Ile Glu Val Lys
                450                 455                 460

Ser Gly Lys Thr Tyr Phe Lys Met His Asp Leu Ile His Asp Leu Ala
465                 470                 475                 480

Thr Ser Met Phe Ser Ala Ser Ala Ser Arg Ser Ile Arg Gln Ile
                485                 490                 495

Asn Val Lys Asp Asp Glu Asp Met Met Phe Ile Val Thr Asn Tyr Lys
                500                 505                 510

Asp Met Met Ser Ile Gly Phe Ser Glu Val Val Ser Ser Tyr Ser Pro
                515                 520                 525

Ser Leu Phe Lys Arg Phe Val Ser Leu Arg Val Leu Asn Leu Ser Asn
530                 535                 540

Ser Glu Phe Glu Gln Leu Pro Ser Ser Val Gly Asp Leu Val His Leu
545                 550                 555                 560

Arg Tyr Leu Asp Leu Ser Gly Asn Lys Ile Cys Ser Leu Pro Lys Arg
                565                 570                 575

Leu Cys Lys Leu Gln Asn Leu Gln Thr Leu Asp Leu Tyr Asn Cys Gln
                580                 585                 590

Ser Leu Ser Cys Leu Pro Lys Gln Thr Ser Lys Leu Cys Ser Leu Arg
                595                 600                 605

Asn Leu Val Leu Asp His Cys Pro Leu Thr Ser Met Pro Pro Arg Ile
                610                 615                 620

Gly Leu Leu Thr Cys Leu Lys Thr Leu Gly Tyr Phe Val Val Gly Glu
625                 630                 635                 640
```

```
Arg Lys Gly Tyr Gln Leu Gly Glu Leu Arg Asn Leu Asn Leu Arg Gly
                645                 650                 655
Ala Ile Ser Ile Thr His Leu Glu Arg Val Lys Asn Asp Met Glu Ala
            660                 665                 670
Lys Glu Ala Asn Leu Ser Ala Lys Ala Asn Leu His Ser Leu Ser Met
        675                 680                 685
Ser Trp Asp Arg Pro Asn Arg Tyr Glu Ser Glu Val Lys Val Leu
    690                 695                 700
Glu Ala Leu Lys Pro His Pro Asn Leu Lys Tyr Leu Glu Ile Ile Asp
705                 710                 715                 720
Phe Cys Gly Phe Cys Leu Pro Asp Trp Met Asn His Ser Val Leu Lys
                725                 730                 735
Asn Val Val Ser Ile Leu Ile Ser Gly Cys Glu Asn Cys Ser Cys Leu
            740                 745                 750
Pro Pro Phe Gly Glu Leu Pro Cys Leu Glu Ser Leu Glu Leu Gln Asp
        755                 760                 765
Gly Ser Val Glu Val Glu Tyr Val Glu Asp Ser Gly Phe Leu Thr Arg
    770                 775                 780
Arg Arg Phe Pro Ser Leu Arg Lys Leu His Ile Gly Phe Cys Asn
785                 790                 795                 800
Leu Lys Gly Leu Gln Arg Met Lys Gly Ala Glu Gln Phe Pro Val Leu
                805                 810                 815
Glu Glu Met Lys Ile Ser Asp Cys Pro Met Phe Val Phe Pro Thr Leu
            820                 825                 830
Ser Ser Val Lys Lys Leu Glu Ile Trp Gly Glu Ala Asp Ala Gly Gly
        835                 840                 845
Leu Ser Ser Ile Ser Asn Leu Ser Thr Leu Thr Ser Leu Lys Ile Phe
    850                 855                 860
Ser Asn His Thr Val Thr Ser Leu Leu Glu Glu Met Phe Lys Asn Leu
865                 870                 875                 880
Glu Asn Leu Ile Tyr Leu Ser Val Ser Phe Leu Glu Asn Leu Lys Glu
                885                 890                 895
Leu Pro Thr Ser Leu Ala Ser Leu Asn Asn Leu Lys Cys Leu Asp Ile
            900                 905                 910
Arg Tyr Cys Tyr Ala Leu Glu Ser Leu Pro Glu Glu Gly Leu Glu Gly
        915                 920                 925
Leu Ser Ser Leu Thr Glu Leu Phe Val Glu His Cys Asn Met Leu Lys
    930                 935                 940
Cys Leu Pro Glu Gly Leu Gln His Leu Thr Thr Leu Thr Ser Leu Lys
945                 950                 955                 960
Ile Arg Gly Cys Pro Gln Leu Ile Lys Arg Cys Glu Lys Gly Ile Gly
                965                 970                 975
Glu Asp Trp His Lys Ile Ser His Ile Pro Asn Val Asn Ile Tyr Ile
            980                 985                 990

<210> SEQ ID NO 57
<211> LENGTH: 1040
<212> TYPE: PRT
<213> ORGANISM: Artificial Sequence
<220> FEATURE:
<223> OTHER INFORMATION: Description of Artificial Sequence: alignment
      RGC4-blb/RGA4-blb
<220> FEATURE:
<221> NAME/KEY: SITE
<222> LOCATION: (1)..(1040)
```

-continued

```
<400> SEQUENCE: 57

Met Ala Glu Ala Phe Leu Gln Val Leu Glu Asn Leu Thr Ser Phe
 1               5                  10                  15

Ile Gly Asp Lys Leu Val Leu Ile Phe Gly Phe Glu Lys Glu Cys Glu
                20                  25                  30

Lys Leu Ser Ser Val Phe Ser Thr Ile Gln Ala Val Leu Gln Asp Ala
            35                  40                  45

Gln Glu Lys Gln Leu Lys Asp Lys Ala Ile Glu Asn Trp Leu Gln Lys
    50                  55                  60

Leu Asn Ser Ala Ala Tyr Glu Val Asp Asp Ile Leu Gly Glu Cys Lys
65                  70                  75                  80

Asn Glu Ala Ile Arg Phe Glu Gln Ser Arg Leu Gly Phe Tyr His Pro
                85                  90                  95

Gly Ile Ile Asn Phe Arg His Lys Ile Gly Arg Arg Met Lys Glu Ile
               100                 105                 110

Met Glu Lys Leu Asp Ala Ile Ser Glu Glu Arg Lys Phe His Phe
            115                 120                 125

Leu Glu Lys Ile Thr Glu Arg Gln Ala Ala Ala Thr Arg Glu Thr
            130                 135                 140

Val Gly Trp Gln Trp Gly Trp Ala Arg Leu Glu Tyr Lys Arg Leu Leu
145                 150                 155                 160

Leu Gly Val Leu Met Arg Ile Met Ser Leu Arg Met His Val Ser Thr
                165                 170                 175

Cys Ser Thr Leu Tyr Glu Phe Lys Phe Tyr Leu Cys Thr Pro Lys Val
                180                 185                 190

Gly Ala Arg Arg Cys Phe Val Leu Thr Glu Pro Lys Val Tyr Gly Arg
            195                 200                 205

Asp Lys Glu Glu Asp Glu Ile Val Lys Ile Leu Ile Asn Asn Val Asn
    210                 215                 220

Val Ala Glu Glu Leu Pro Val Phe Pro Ile Ile Gly Met Gly Gly Leu
225                 230                 235                 240

Gly Lys Thr Thr Leu Ala Gln Met Ile Phe Asn Asp Glu Arg Val Thr
                245                 250                 255

Lys His Phe Asn Pro Lys Ile Trp Val Cys Val Ser Asp Asp Phe Asp
                260                 265                 270

Glu Lys Arg Leu Ile Lys Thr Ile Ile Gly Asn Ile Glu Arg Ser Ser
            275                 280                 285

Pro His Val Glu Asp Leu Ala Ser Phe Gln Lys Lys Leu Gln Glu Leu
    290                 295                 300

Leu Asn Gly Lys Arg Tyr Leu Val Leu Asp Asp Val Trp Asn Asp
305                 310                 315                 320

Asp Leu Glu Lys Trp Ala Lys Leu Arg Ala Val Leu Thr Val Gly Ala
                325                 330                 335

Arg Gly Ala Ser Ile Leu Ala Thr Thr Arg Leu Glu Lys Val Gly Ser
            340                 345                 350

Ile Met Gly Thr Leu Gln Pro Tyr His Leu Ser Asn Leu Ser Pro His
        355                 360                 365

Asp Ser Leu Leu Leu Phe Met Gln Arg Ala Phe Gly Gln Gln Lys Glu
    370                 375                 380

Ala Asn Pro Asn Leu Val Ala Ile Gly Lys Glu Ile Val Lys Lys Cys
385                 390                 395                 400

Gly Gly Val Pro Leu Ala Ala Lys Thr Leu Gly Gly Leu Leu Arg Phe
                405                 410                 415
```

-continued

```
Lys Arg Glu Glu Ser Glu Trp Glu His Val Arg Asp Asn Glu Ile Trp
            420                 425                 430

Ser Leu Pro Gln Asp Glu Ser Ser Ile Leu Pro Ala Leu Arg Leu Ser
            435                 440                 445

Tyr His His Leu Pro Leu Asp Leu Arg Gln Cys Phe Ala Tyr Cys Ala
            450                 455                 460

Val Phe Pro Lys Asp Thr Lys Met Ile Lys Glu Asn Leu Ile Thr Leu
465                 470                 475                 480

Trp Met Ala His Gly Phe Leu Ser Lys Gly Asn Leu Glu Leu Glu
                485                 490                 495

Asp Val Gly Asn Glu Val Trp Asn Glu Leu Tyr Leu Arg Ser Phe Phe
            500                 505                 510

Gln Glu Ile Glu Ala Lys Ser Gly Asn Thr Tyr Phe Lys Ile His Asp
            515                 520                 525

Leu Ile His Asp Leu Ala Thr Ser Leu Phe Ser Ala Ser Ala Ser Cys
            530                 535                 540

Gly Asn Ile Arg Glu Ile Asn Val Lys Asp Tyr Lys His Thr Val Ser
545                 550                 555                 560

Ile Gly Phe Ala Ala Val Val Ser Ser Tyr Ser Pro Ser Leu Leu Lys
                565                 570                 575

Lys Phe Val Ser Leu Arg Val Leu Asn Leu Ser Tyr Ser Lys Leu Glu
            580                 585                 590

Gln Leu Pro Ser Ser Ile Gly Asp Leu Leu His Leu Arg Tyr Leu Asp
            595                 600                 605

Leu Ser Cys Asn Asn Phe Arg Ser Leu Pro Glu Arg Leu Cys Lys Leu
            610                 615                 620

Gln Asn Leu Gln Thr Leu Asp Val His Asn Cys Tyr Ser Leu Asn Cys
625                 630                 635                 640

Leu Pro Lys Gln Thr Ser Lys Leu Ser Ser Leu Arg His Leu Val Val
            645                 650                 655

Asp Gly Cys Pro Leu Thr Ser Thr Pro Pro Arg Ile Gly Leu Leu Thr
            660                 665                 670

Cys Leu Lys Thr Leu Gly Phe Phe Ile Val Gly Ser Lys Lys Gly Tyr
            675                 680                 685

Gln Leu Gly Glu Leu Lys Asn Leu Asn Leu Cys Gly Ser Ile Ser Ile
            690                 695                 700

Thr His Leu Glu Arg Val Lys Asn Asp Thr Asp Ala Glu Ala Asn Leu
705                 710                 715                 720

Ser Ala Lys Ala Asn Leu Gln Ser Leu Ser Met Ser Trp Asp Asn Asp
            725                 730                 735

Gly Pro Asn Arg Tyr Glu Ser Lys Glu Val Lys Val Leu Glu Ala Leu
            740                 745                 750

Lys Pro His Pro Asn Leu Lys Tyr Leu Glu Ile Ala Phe Gly Gly
            755                 760                 765

Phe Arg Phe Pro Ser Trp Ile Asn His Ser Val Leu Glu Lys Val Ile
            770                 775                 780

Ser Val Arg Ile Lys Ser Cys Lys Asn Cys Leu Cys Leu Pro Pro Phe
785                 790                 795                 800

Gly Glu Leu Pro Cys Leu Glu Asn Leu Glu Leu Gln Asn Gly Ser Ala
            805                 810                 815

Glu Val Glu Tyr Val Glu Glu Asp Asp Val His Ser Arg Phe Ser Thr
            820                 825                 830
```

```
Arg Arg Ser Phe Pro Ser Leu Lys Lys Leu Arg Ile Trp Phe Phe Arg
        835                 840                 845

Ser Leu Lys Gly Leu Met Lys Glu Glu Gly Glu Lys Phe Pro Met
850                 855                 860

Leu Glu Glu Met Ala Ile Leu Tyr Cys Pro Leu Phe Val Phe Pro Thr
865                 870                 875                 880

Leu Ser Ser Val Lys Lys Leu Glu Val His Gly Asn Thr Asn Thr Arg
                885                 890                 895

Gly Leu Ser Ser Ile Ser Asn Leu Ser Thr Leu Thr Ser Leu Arg Ile
                900                 905                 910

Gly Ala Asn Tyr Arg Ala Thr Ser Leu Pro Glu Met Phe Thr Ser
            915                 920                 925

Leu Thr Asn Leu Glu Phe Leu Ser Phe Phe Asp Phe Lys Asn Leu Lys
            930                 935                 940

Asp Leu Pro Thr Ser Leu Thr Ser Leu Asn Ala Leu Lys Arg Leu Gln
945                 950                 955                 960

Ile Glu Ser Cys Asp Ser Leu Glu Ser Phe Pro Glu Gln Gly Leu Glu
                965                 970                 975

Gly Leu Thr Ser Leu Thr Gln Leu Phe Val Lys Tyr Cys Lys Met Leu
            980                 985                 990

Lys Cys Leu Pro Glu Gly Leu Gln His Leu Thr Ala Leu Thr Asn Leu
            995                 1000                1005

Gly Val Ser Gly Cys Pro Glu Val Glu Lys Arg Cys Asp Lys Glu Ile
            1010                1015                1020

Gly Glu Asp Trp His Lys Ile Ala His Ile Pro Asn Leu Asp Ile His
1025                1030                1035                1040

<210> SEQ ID NO 58
<211> LENGTH: 979
<212> TYPE: PRT
<213> ORGANISM: Artificial Sequence
<220> FEATURE:
<223> OTHER INFORMATION: Description of Artificial Sequence: alignment
      RGA3-b1b
<220> FEATURE:
<221> NAME/KEY: SITE
<222> LOCATION: (1)..(979)

<400> SEQUENCE: 58

Met Ala Glu Ala Phe Ile Gln Val Val Leu Asp Asn Leu Thr Ser Phe
1               5                   10                  15

Leu Lys Gly Glu Leu Val Leu Leu Phe Gly Phe Gln Asp Glu Phe Gln
            20                  25                  30

Arg Leu Ser Ser Met Phe Ser Thr Ile Gln Ala Val Leu Glu Asp Ala
        35                  40                  45

Gln Glu Lys Gln Leu Asn Asp Lys Pro Leu Glu Asn Trp Leu Gln Lys
    50                  55                  60

Leu Asn Ala Ala Thr Tyr Glu Val Asp Asp Ile Leu Asp Glu Tyr Lys
65                  70                  75                  80

Thr Lys Ala Thr Arg Phe Leu Gln Ser Glu Tyr Gly Arg Tyr His Pro
                85                  90                  95

Lys Val Ile Pro Phe Arg His Lys Val Gly Lys Arg Met Asp Gln Val
            100                 105                 110

Met Lys Lys Leu Asn Ala Ile Ala Glu Glu Arg Lys Asn Phe His Leu
        115                 120                 125

Gln Glu Lys Ile Ile Glu Arg Gln Ala Ala Thr Arg Glu Thr Gly Ser
    130                 135                 140
```

-continued

```
Val Leu Thr Glu Pro Gln Val Tyr Gly Arg Asp Lys Glu Lys Asp Glu
145                 150                 155                 160

Ile Val Lys Ile Leu Ile Asn Asn Val Ser Asp Ala Gln Lys Leu Ser
            165                 170                 175

Val Leu Pro Ile Leu Gly Met Gly Gly Leu Gly Lys Thr Thr Leu Ser
            180                 185                 190

Gln Met Val Phe Asn Asp Gln Arg Val Thr Glu Arg Phe Tyr Pro Lys
        195                 200                 205

Ile Trp Ile Cys Val Ser Asp Asp Phe Asp Glu Lys Arg Leu Ile Lys
    210                 215                 220

Ala Ile Val Glu Ser Ile Glu Gly Lys Ser Leu Ser Asp Met Asp Leu
225                 230                 235                 240

Ala Pro Leu Gln Lys Lys Leu Gln Glu Leu Leu Asn Gly Lys Arg Tyr
                245                 250                 255

Phe Leu Val Leu Asp Asp Val Trp Asn Glu Asp Gln His Lys Trp Ala
            260                 265                 270

Asn Leu Arg Ala Val Leu Lys Val Gly Ala Ser Gly Ala Phe Val Leu
        275                 280                 285

Thr Thr Thr Arg Leu Glu Lys Val Gly Ser Ile Met Gly Thr Leu Gln
    290                 295                 300

Pro Tyr Glu Leu Ser Asn Leu Ser Pro Glu Asp Cys Trp Phe Leu Phe
305                 310                 315                 320

Met Gln Arg Ala Phe Gly His Gln Glu Glu Ile Asn Pro Asn Leu Val
                325                 330                 335

Ala Ile Gly Lys Glu Ile Val Lys Lys Cys Gly Gly Val Pro Leu Ala
            340                 345                 350

Ala Lys Thr Leu Gly Gly Ile Leu Arg Phe Lys Arg Glu Glu Arg Ala
        355                 360                 365

Trp Glu His Val Arg Asp Ser Pro Ile Trp Asn Leu Pro Gln Asp Glu
    370                 375                 380

Ser Ser Ile Leu Pro Ala Leu Arg Leu Ser Tyr His His Leu Pro Leu
385                 390                 395                 400

Asp Leu Asp Gln Cys Phe Val Tyr Cys Ala Val Phe Pro Lys Asp Thr
                405                 410                 415

Lys Met Ala Lys Glu Asn Leu Ile Ala Phe Trp Met Ala His Gly Phe
            420                 425                 430

Leu Leu Ser Lys Gly Asn Leu Glu Leu Glu Asp Val Gly Asp Glu Val
        435                 440                 445

Trp Asn Glu Leu Tyr Leu Arg Ser Phe Phe Gln Glu Ile Glu Val Glu
    450                 455                 460

Ser Gly Lys Thr Tyr Phe Lys Met His Asp Leu Ile His Asp Leu Ala
465                 470                 475                 480

Thr Ser Leu Phe Ser Ala Asn Thr Ser Ser Asn Ile Arg Glu Ile
                485                 490                 495

Asn Ala Asn Tyr Asp Gly Tyr Met Met Ser Ile Gly Phe Ala Glu Val
            500                 505                 510

Val Ser Ser Tyr Ser Pro Ser Leu Leu Gln Lys Phe Val Ser Leu Arg
        515                 520                 525

Val Leu Asn Leu Arg Asn Ser Asn Leu Asn Gln Leu Pro Ser Ser Ile
    530                 535                 540

Gly Asp Leu Val His Leu Arg Tyr Leu Asp Leu Ser Gly Asn Phe Arg
545                 550                 555                 560
```

-continued

```
Ile Arg Asn Leu Pro Lys Arg Leu Cys Arg Leu Gln Asn Leu Gln Thr
            565                 570                 575

Leu Asp Leu His Tyr Cys Asp Ser Leu Ser Cys Leu Pro Lys Gln Thr
            580                 585                 590

Ser Lys Leu Gly Ser Leu Arg Asn Leu Leu Asp Gly Cys Ser Leu
            595                 600                 605

Thr Ser Thr Pro Pro Arg Ile Gly Leu Leu Thr Cys Leu Lys Ser Leu
    610                 615                 620

Ser Cys Phe Val Ile Gly Lys Arg Lys Gly Tyr Gln Leu Gly Glu Leu
625                 630                 635                 640

Lys Asn Leu Asn Leu Tyr Gly Ser Ile Ser Ile Thr Lys Leu Asp Arg
                645                 650                 655

Val Lys Lys Asp Ser Asp Ala Lys Glu Ala Asn Leu Ser Ala Lys Ala
            660                 665                 670

Asn Leu His Ser Leu Cys Leu Ser Trp Asp Leu Asp Gly Lys His Arg
            675                 680                 685

Tyr Asp Ser Glu Val Leu Glu Ala Leu Lys Pro His Ser Asn Leu Lys
    690                 695                 700

Tyr Leu Glu Ile Asn Gly Phe Gly Gly Ile Arg Leu Pro Asp Trp Met
705                 710                 715                 720

Asn Gln Ser Val Leu Lys Asn Val Val Ser Ile Arg Ile Arg Gly Cys
                725                 730                 735

Glu Asn Cys Ser Cys Leu Pro Pro Phe Gly Glu Leu Pro Cys Leu Glu
            740                 745                 750

Ser Leu Glu Leu His Thr Gly Ser Ala Asp Val Glu Tyr Val Glu Asp
            755                 760                 765

Asn Val His Pro Gly Arg Phe Pro Ser Leu Arg Lys Leu Val Ile Trp
    770                 775                 780

Asp Phe Ser Asn Leu Lys Gly Leu Leu Lys Lys Glu Gly Glu Glu Gln
785                 790                 795                 800

Phe Pro Val Leu Glu Glu Met Thr Phe Tyr Trp Cys Pro Met Phe Val
                805                 810                 815

Ile Pro Thr Leu Ser Ser Val Lys Thr Leu Lys Val Ile Ala Thr Asp
            820                 825                 830

Ala Thr Val Leu Arg Ser Ile Ser Asn Leu Arg Ala Leu Thr Ser Leu
            835                 840                 845

Asp Ile Ser Asn Asn Val Glu Ala Thr Ser Leu Pro Glu Glu Met Phe
    850                 855                 860

Lys Ser Leu Ala Asn Leu Lys Tyr Leu Asn Ile Ser Phe Phe Arg Asn
865                 870                 875                 880

Leu Lys Glu Leu Pro Thr Ser Leu Ala Ser Leu Asn Ala Leu Lys Ser
                885                 890                 895

Leu Lys Phe Glu Phe Cys Asn Ala Leu Glu Ser Leu Pro Ala Glu Gly
            900                 905                 910

Val Lys Gly Leu Thr Ser Leu Thr Glu Leu Ser Val Ser Asn Cys Met
            915                 920                 925

Met Leu Lys Cys Leu Pro Glu Gly Leu Gln His Leu Thr Ala Leu Thr
    930                 935                 940

Thr Leu Thr Ile Thr Gln Cys Pro Ile Val Phe Lys Arg Cys Glu Arg
945                 950                 955                 960

Gly Ile Gly Glu Asp Trp His Lys Ile Ala His Ile Pro Tyr Leu Thr
                965                 970                 975

Leu Tyr Glu
```

<210> SEQ ID NO 59
<211> LENGTH: 945
<212> TYPE: PRT
<213> ORGANISM: Artificial Sequence
<220> FEATURE:
<223> OTHER INFORMATION: Description of Artificial Sequence: alignment SH10-tub
<220> FEATURE:
<221> NAME/KEY: SITE
<222> LOCATION: (1)..(945)

<400> SEQUENCE: 59

```
Met Ala Glu Ala Phe Ile Gln Val Leu Ile Asp Asn Leu Thr Ser Phe
  1               5                  10                  15

Leu Lys Gly Glu Leu Val Leu Leu Phe Gly Phe Gln Asn Glu Phe Gln
                 20                  25                  30

Arg Leu Ser Ser Ile Phe Ser Thr Ile Gln Ala Val Leu Glu Asp Ala
             35                  40                  45

Gln Glu Lys Gln Leu Asn Asp Lys Pro Leu Glu Asn Trp Leu Gln Lys
         50                  55                  60

Leu Asn Ala Ala Thr Tyr Glu Val Asp Asp Ile Leu Asp Glu Tyr Lys
 65                  70                  75                  80

Thr Lys Ala Thr Arg Phe Ser Gln Ser Ala Tyr Gly Arg Tyr His Pro
                 85                  90                  95

Lys Val Ile Pro Phe Arg His Lys Val Gly Lys Arg Met Asp Gln Val
            100                 105                 110

Met Lys Lys Leu Asn Ala Ile Ala Glu Glu Arg Lys Asn Phe His Leu
        115                 120                 125

His Glu Lys Ile Ile Glu Arg Gln Ala Val Arg Glu Thr Gly Ser
    130                 135                 140

Val Leu Thr Glu Pro Gln Val Tyr Gly Arg Asp Lys Glu Glu Asp Glu
145                 150                 155                 160

Ile Val Lys Ile Leu Ile Asn Asn Val Ser Asp Ala Gln His Leu Ser
                165                 170                 175

Val Leu Pro Ile Leu Gly Met Gly Gly Leu Gly Lys Thr Thr Leu Ala
            180                 185                 190

Gln Met Val Phe Asn Asp Gln Arg Ile Thr Glu His Phe His Ser Lys
        195                 200                 205

Ile Trp Ile Cys Val Ser Glu Asp Phe Asp Glu Lys Arg Leu Leu Lys
    210                 215                 220

Ala Ile Ile Glu Ser Ile Glu Gly Arg Pro Leu Leu Gly Glu Met Asp
225                 230                 235                 240

Leu Ala Pro Leu Gln Lys Lys Leu Gln Glu Leu Leu Asn Gly Lys Arg
                245                 250                 255

Tyr Phe Leu Val Leu Asp Asp Val Trp Asn Glu Asp Gln Gln Lys Trp
            260                 265                 270

Ala Asn Leu Arg Ala Val Leu Lys Val Gly Ala Ser Gly Ala Phe Val
        275                 280                 285

Leu Ala Thr Thr Arg Leu Glu Lys Val Gly Ser Ile Met Gly Thr Leu
    290                 295                 300

Gln Pro Tyr Glu Leu Ser Asn Leu Ser Gln Glu Asp Cys Trp Leu Leu
305                 310                 315                 320

Phe Ile Gln Cys Ala Phe Gly His Gln Glu Glu Ile Asn Pro Asn Leu
                325                 330                 335

Val Ala Ile Gly Lys Glu Ile Val Lys Lys Ser Gly Gly Val Pro Leu
```

-continued

```
            340                 345                 350
Ala Ala Lys Thr Leu Gly Gly Ile Leu Arg Phe Lys Arg Glu Glu Arg
            355                 360                 365
Ala Trp Glu His Val Arg Asp Ser Glu Ile Trp Asn Leu Pro Gln Glu
    370                 375                 380
Glu Arg Ser Ile Leu Pro Ala Leu Arg Leu Ser Tyr His His Leu Pro
385                 390                 395                 400
Leu Asp Leu Arg Gln Cys Phe Ala Tyr Cys Ala Val Phe Pro Lys Asp
                405                 410                 415
Thr Lys Met Glu Lys Glu Lys Leu Ile Ser Leu Trp Met Ala His Gly
            420                 425                 430
Phe Leu Leu Leu Glu Gly Lys Leu Gln Pro Glu Asp Val Gly Asn Glu
            435                 440                 445
Val Ser Lys Glu Leu Cys Leu Arg Ser Phe Phe Gln Glu Ile Glu Ala
    450                 455                 460
Lys Cys Gly Lys Thr Tyr Phe Lys Met His Asp Leu His His Asp Leu
465                 470                 475                 480
Ala Thr Ser Leu Phe Ser Ala Ser Thr Ser Ser Ser Asn Ile Arg Glu
                485                 490                 495
Ile Asn Val Lys Gly Tyr Pro His Lys Met Ser Ile Gly Phe Thr Glu
                500                 505                 510
Val Val Ser Ser Tyr Ser Pro Ser Leu Ser Gln Lys Phe Val Ser Leu
            515                 520                 525
Arg Val Leu Asn Leu Ser Asn Leu His Phe Glu Glu Leu Ser Ser Ser
            530                 535                 540
Ile Gly Asp Leu Val His Met Arg Cys Leu Asp Leu Ser Glu Asn Ser
545                 550                 555                 560
Gly Ile Arg Ser Leu Pro Lys Gln Leu Cys Lys Leu Gln Asn Leu Gln
                565                 570                 575
Thr Leu Asp Leu His Asn Cys Tyr Ser Leu Ser Cys Leu Pro Lys Glu
                580                 585                 590
Pro Ser Lys Leu Gly Ser Leu Arg Asn Leu Phe Phe His Gly Cys Asp
            595                 600                 605
Glu Leu Asn Ser Met Pro Pro Arg Ile Gly Ser Leu Thr Phe Leu Lys
    610                 615                 620
Thr Leu Lys Trp Ile Cys Cys Gly Ile Lys Lys Gly Tyr Gln Leu Gly
625                 630                 635                 640
Lys Leu Arg Asp Val Asn Leu Tyr Gly Ser Ile Glu Ile Thr His Leu
                645                 650                 655
Glu Arg Val Lys Asn Val Met Asp Ala Lys Glu Ala Asn Leu Ser Ala
            660                 665                 670
Lys Gly Asn Leu His Ser Leu Ile Met Asn Trp Ser Arg Lys Gly Pro
            675                 680                 685
His Ile Tyr Glu Ser Glu Glu Val Arg Val Ile Glu Ala Leu Lys Pro
    690                 695                 700
His Pro Asn Leu Thr Cys Leu Thr Ile Ser Gly Phe Arg Gly Phe Arg
705                 710                 715                 720
Phe Pro Glu Trp Met Asn His Ser Val Leu Lys Asn Val Val Ser Ile
                725                 730                 735
Glu Ile Ser Gly Cys Lys Asn Cys Ser Cys Leu Pro Pro Phe Gly Glu
                740                 745                 750
Leu Pro Cys Leu Lys Arg Leu Glu Leu Gln Lys Gly Ser Ala Glu Val
            755                 760                 765
```

-continued

```
Glu Tyr Val Asp Ser Gly Phe Pro Thr Arg Arg Phe Pro Ser Leu
    770                 775                 780

Arg Lys Leu Phe Ile Gly Glu Phe Pro Asn Leu Lys Gly Leu Leu Lys
785                 790                 795                 800

Lys Glu Gly Glu Gln Phe Pro Val Leu Glu Arg Met Thr Ile Phe
                805                 810                 815

Tyr Cys His Met Phe Val Tyr Thr Thr Leu Ser Asn Phe Arg Ala Leu
            820                 825                 830

Thr Ser Leu His Ile Ser His Asn Asn Glu Ala Thr Ser Leu Pro Glu
        835                 840                 845

Glu Ile Phe Lys Ser Phe Ala Asn Leu Lys Tyr Leu Lys Ile Ser Leu
    850                 855                 860

Phe Tyr Asn Leu Lys Glu Leu Pro Ser Ser Leu Ala Cys Leu Asn Ala
865                 870                 875                 880

Leu Lys Thr Leu Glu Ile His Ser Cys Ser Ala Leu Glu Ser Leu Pro
                885                 890                 895

Glu Glu Gly Val Lys Gly Leu Thr Ser Leu Thr Glu Leu Phe Val Tyr
            900                 905                 910

Asp Cys Glu Met Leu Lys Phe Leu Pro Glu Gly Leu Gln His Leu Thr
        915                 920                 925

Ala Leu Thr Ser Leu Lys Leu Arg Arg Cys Pro Gln Leu Ile Lys Arg
    930                 935                 940

Cys
945

<210> SEQ ID NO 60
<211> LENGTH: 992
<212> TYPE: PRT
<213> ORGANISM: Artificial Sequence
<220> FEATURE:
<223> OTHER INFORMATION: Description of Artificial Sequence: alignment
      RGA1-b1b
<220> FEATURE:
<221> NAME/KEY: SITE
<222> LOCATION: (1)..(992)

<400> SEQUENCE: 60

Met Ala Glu Ala Phe Leu Gln Val Leu Leu Asp Asn Leu Thr Phe Phe
1               5                   10                  15

Ile Gln Gly Glu Leu Gly Leu Val Phe Gly Phe Glu Lys Glu Phe Lys
                20                  25                  30

Lys Leu Ser Ser Met Phe Ser Met Ile Gln Ala Val Leu Glu Asp Ala
            35                  40                  45

Gln Glu Lys Gln Leu Lys Tyr Lys Ala Ile Lys Asn Trp Leu Gln Lys
        50                  55                  60

Leu Asn Val Ala Ala Tyr Glu Val Asp Asp Ile Leu Asp Asp Cys Lys
65                  70                  75                  80

Thr Glu Ala Ala Arg Phe Lys Gln Ala Val Leu Gly Arg Tyr His Pro
                85                  90                  95

Arg Thr Ile Thr Phe Cys Tyr Lys Val Gly Lys Arg Met Lys Glu Met
            100                 105                 110

Met Glu Lys Leu Asp Ala Ile Ala Glu Glu Arg Arg Asn Phe His Leu
        115                 120                 125

Asp Glu Arg Ile Ile Glu Arg Gln Ala Ala Arg Gln Thr Gly Phe
    130                 135                 140

Val Leu Thr Glu Pro Lys Val Tyr Gly Arg Glu Lys Glu Glu Asp Glu
```

```
            145                 150                 155                 160
        Ile Val Lys Ile Leu Ile Asn Asn Val Ser Tyr Ser Glu Glu Val Pro
                        165                 170                 175
        Val Leu Pro Ile Leu Gly Met Gly Gly Leu Gly Lys Thr Thr Leu Ala
                        180                 185                 190
        Gln Met Val Phe Asn Asp Gln Arg Ile Thr Glu His Phe Asn Leu Lys
                        195                 200                 205
        Ile Trp Val Cys Val Ser Asp Asp Phe Asp Glu Lys Arg Leu Ile Lys
                        210                 215                 220
        Ala Ile Val Glu Ser Ile Glu Gly Lys Ser Leu Gly Asp Met Asp Leu
        225                 230                 235                 240
        Ala Pro Leu Gln Lys Lys Leu Gln Glu Leu Leu Asn Gly Lys Arg Tyr
                        245                 250                 255
        Phe Leu Val Leu Asp Asp Val Trp Asn Glu Asp Gln Glu Lys Trp Asp
                        260                 265                 270
        Asn Leu Arg Ala Val Leu Lys Ile Gly Ala Ser Gly Ala Ser Ile Leu
                        275                 280                 285
        Ile Thr Thr Arg Leu Glu Lys Ile Gly Ser Ile Met Gly Thr Leu Gln
                        290                 295                 300
        Leu Tyr Gln Leu Ser Asn Leu Ser Gln Glu Asp Cys Trp Leu Leu Phe
        305                 310                 315                 320
        Lys Gln Arg Ala Phe Cys His Gln Thr Glu Thr Ser Pro Lys Leu Met
                        325                 330                 335
        Glu Ile Gly Lys Glu Ile Val Lys Lys Cys Gly Gly Val Pro Leu Ala
                        340                 345                 350
        Ala Lys Thr Leu Gly Gly Leu Leu Arg Phe Lys Arg Glu Glu Ser Glu
                        355                 360                 365
        Trp Glu His Val Arg Asp Ser Glu Ile Trp Asn Leu Pro Gln Asp Glu
                        370                 375                 380
        Asn Ser Val Leu Pro Ala Leu Arg Leu Ser Tyr His His Leu Pro Leu
        385                 390                 395                 400
        Asp Leu Arg Gln Cys Phe Ala Tyr Cys Ala Val Phe Pro Lys Asp Thr
                        405                 410                 415
        Lys Ile Glu Lys Glu Tyr Leu Ile Ala Leu Trp Met Ala His Ser Phe
                        420                 425                 430
        Leu Leu Ser Lys Gly Asn Met Glu Leu Glu Asp Val Gly Asn Glu Val
                        435                 440                 445
        Trp Asn Glu Leu Tyr Leu Arg Ser Phe Phe Gln Glu Ile Glu Val Lys
                        450                 455                 460
        Ser Gly Lys Thr Tyr Phe Lys Met His Asp Leu Ile His Asp Leu Ala
        465                 470                 475                 480
        Thr Ser Met Phe Ser Ala Ser Ala Ser Ser Arg Ser Ile Arg Gln Ile
                        485                 490                 495
        Asn Val Lys Asp Asp Glu Asp Met Met Phe Ile Val Thr Asn Tyr Lys
                        500                 505                 510
        Asp Met Met Ser Ile Gly Phe Ser Glu Val Val Ser Ser Tyr Ser Pro
                        515                 520                 525
        Ser Leu Phe Lys Arg Phe Val Ser Leu Arg Val Leu Asn Leu Ser Asn
                        530                 535                 540
        Ser Glu Phe Glu Gln Leu Pro Ser Ser Val Gly Asp Leu Val His Leu
        545                 550                 555                 560
        Arg Tyr Leu Asp Leu Ser Gly Asn Lys Ile Cys Ser Leu Pro Lys Arg
                        565                 570                 575
```

-continued

```
Leu Cys Lys Leu Gln Asn Leu Gln Thr Leu Asp Leu Tyr Asn Cys Gln
            580                 585                 590

Ser Leu Ser Cys Leu Pro Lys Gln Thr Ser Lys Leu Cys Ser Leu Arg
            595                 600                 605

Asn Leu Val Leu Asp His Cys Pro Leu Thr Ser Met Pro Pro Arg Ile
            610                 615                 620

Gly Leu Leu Thr Cys Leu Lys Thr Leu Gly Tyr Phe Val Val Gly Glu
625                 630                 635                 640

Arg Lys Gly Tyr Gln Leu Gly Glu Leu Arg Asn Leu Asn Leu Arg Gly
                645                 650                 655

Ala Ile Ser Ile Thr His Leu Glu Arg Val Lys Asn Asp Met Glu Ala
            660                 665                 670

Lys Glu Ala Asn Leu Ser Ala Lys Ala Asn Leu His Ser Leu Ser Met
            675                 680                 685

Ser Trp Asp Arg Pro His Arg Tyr Glu Ser Glu Glu Val Lys Val Leu
            690                 695                 700

Glu Ala Leu Lys Pro His Pro Asn Leu Lys Tyr Leu Glu Ile Ile Asp
705                 710                 715                 720

Phe Cys Gly Phe Cys Leu Pro Asp Trp Met Asn His Ser Val Leu Lys
                725                 730                 735

Asn Val Val Ser Ile Leu Ile Ser Gly Cys Glu Asn Cys Ser Cys Leu
            740                 745                 750

Pro Pro Phe Gly Glu Leu Pro Cys Leu Glu Ser Leu Glu Leu Gln Asp
            755                 760                 765

Gly Ser Val Glu Val Glu Tyr Val Glu Asp Ser Gly Phe Leu Thr Arg
            770                 775                 780

Arg Arg Phe Pro Ser Leu Arg Lys Leu His Ile Gly Gly Phe Cys Asn
785                 790                 795                 800

Leu Lys Gly Leu Gln Arg Met Lys Gly Glu Glu Gln Phe Pro Val Leu
                805                 810                 815

Glu Glu Met Lys Ile Ser Asp Cys Pro Met Phe Val Phe Pro Thr Leu
            820                 825                 830

Ser Ser Val Lys Lys Leu Glu Ile Trp Gly Glu Ala Asp Ala Gly Gly
            835                 840                 845

Leu Ser Ser Ile Ser Asn Leu Ser Thr Leu Thr Ser Leu Lys Ile Phe
            850                 855                 860

Ser Asn His Thr Val Thr Ser Leu Leu Glu Glu Met Phe Lys Asn Leu
865                 870                 875                 880

Glu Asn Leu Ile Tyr Leu Ser Val Ser Phe Leu Glu Asn Leu Lys Glu
                885                 890                 895

Leu Pro Thr Ser Leu Ala Ser Leu Asn Asn Leu Lys Cys Leu Asp Ile
            900                 905                 910

Arg Tyr Cys Tyr Ala Leu Glu Ser Leu Pro Glu Glu Gly Leu Glu Gly
            915                 920                 925

Leu Ser Ser Leu Thr Glu Leu Phe Val Glu His Cys Asn Met Leu Lys
            930                 935                 940

Cys Leu Pro Glu Gly Leu Gln His Leu Thr Thr Leu Thr Ser Leu Lys
945                 950                 955                 960

Ile Arg Gly Cys Pro Gln Leu Ile Lys Arg Cys Glu Lys Gly Ile Gly
                965                 970                 975

Glu Asp Trp His Lys Ile Ser His Ile Pro Asn Val Asn Ile Tyr Ile
            980                 985                 990
```

```
<210> SEQ ID NO 61
<211> LENGTH: 972
<212> TYPE: PRT
<213> ORGANISM: Artificial Sequence
<220> FEATURE:
<223> OTHER INFORMATION: Description of Artificial Sequence: alignment
      B149-b1b
<220> FEATURE:
<221> NAME/KEY: SITE
<222> LOCATION: (1)..(972)

<400> SEQUENCE: 61

Met Ala Glu Ala Phe Ile Gln Val Leu Leu Asp Asn Leu Thr Phe Phe
 1               5                  10                  15

Ile Gln Gly Glu Leu Gly Leu Val Phe Gly Phe Glu Lys Glu Phe Lys
                20                  25                  30

Lys Leu Ser Ser Met Phe Ser Met Ile Gln Ala Val Leu Glu Asp Ala
            35                  40                  45

Gln Glu Lys Gln Leu Lys Tyr Lys Ala Ile Lys Asn Trp Leu Gln Lys
        50                  55                  60

Leu Asn Val Ala Ala Tyr Glu Val Asp Asp Ile Leu Asp Asp Cys Lys
 65                  70                  75                  80

Thr Glu Ala Ala Arg Phe Lys Gln Ala Val Leu Gly Arg Tyr His Pro
                 85                  90                  95

Arg Thr Ile Thr Phe Cys Tyr Lys Val Gly Lys Arg Met Lys Glu Met
                100                 105                 110

Met Glu Lys Leu Asp Ala Ile Ala Glu Glu Arg Arg Asn Phe His Leu
            115                 120                 125

Asp Glu Arg Ile Ile Glu Arg Gln Ala Ala Arg Arg Gln Thr Gly Phe
        130                 135                 140

Val Leu Thr Glu Pro Lys Val Tyr Gly Arg Glu Lys Glu Glu Asp Glu
145                 150                 155                 160

Ile Val Lys Ile Leu Ile Asn Asn Val Ser Tyr Ser Glu Glu Val Pro
                165                 170                 175

Val Leu Pro Ile Leu Gly Met Gly Gly Leu Gly Lys Thr Thr Leu Ala
            180                 185                 190

Gln Met Val Phe Asn Asp Gln Arg Ile Thr Glu His Phe Asn Leu Lys
        195                 200                 205

Ile Trp Val Cys Val Ser Asp Asp Phe Asp Glu Lys Arg Leu Ile Lys
    210                 215                 220

Ala Ile Val Glu Ser Ile Glu Gly Lys Ser Leu Gly Asp Met Asp Leu
225                 230                 235                 240

Ala Pro Leu Gln Lys Lys Leu Gln Glu Leu Leu Asn Gly Lys Arg Tyr
                245                 250                 255

Phe Leu Val Leu Asp Asp Val Trp Asn Glu Asp Gln Glu Lys Trp Asp
            260                 265                 270

Asn Leu Arg Ala Val Leu Lys Ile Gly Ala Ser Gly Ala Ser Ile Leu
        275                 280                 285

Ile Thr Thr Arg Leu Glu Lys Ile Gly Ser Ile Met Gly Thr Leu Gln
    290                 295                 300

Leu Tyr Gln Leu Ser Asn Leu Ser Gln Glu Asp Cys Trp Leu Leu Phe
305                 310                 315                 320

Lys Gln Arg Ala Phe Cys His Gln Thr Glu Thr Ser Pro Lys Leu Met
                325                 330                 335

Glu Ile Gly Lys Glu Ile Val Lys Cys Gly Gly Val Pro Leu Ala
            340                 345                 350
```

```
Ala Lys Thr Leu Gly Gly Leu Leu Arg Phe Lys Arg Glu Glu Ser Glu
        355                 360                 365

Trp Glu His Val Arg Asp Ser Glu Ile Trp Asn Leu Pro Gln Asp Glu
    370                 375                 380

Asn Ser Val Leu Pro Ala Leu Arg Leu Ser Tyr His His Leu Pro Leu
385                 390                 395                 400

Asp Leu Arg Gln Cys Phe Ala Tyr Cys Ala Val Phe Pro Lys Asp Thr
                405                 410                 415

Lys Ile Glu Lys Glu Tyr Leu Ile Ala Leu Trp Met Ala His Ser Phe
            420                 425                 430

Leu Leu Ser Lys Gly Asn Met Glu Leu Glu Asp Val Gly Asn Glu Val
        435                 440                 445

Trp Asn Glu Leu Tyr Leu Arg Ser Phe Phe Gln Gly Ile Glu Val Lys
    450                 455                 460

Ser Gly Lys Thr Tyr Phe Lys Met His Asp Leu Ile His Asp Leu Ala
465                 470                 475                 480

Thr Ser Met Phe Ser Ala Ser Ala Ser Ser Arg Ser Ile Arg Gln Ile
                485                 490                 495

Asn Val Lys Asp Asp Glu Asp Met Met Phe Ile Val Thr Asn Tyr Lys
            500                 505                 510

Asp Met Met Ser Ile Gly Phe Ser Glu Val Val Ser Ser Tyr Ser Pro
        515                 520                 525

Ser Leu Phe Lys Arg Phe Val Ser Leu Arg Val Leu Asn Leu Ser Asn
    530                 535                 540

Ser Glu Phe Glu Gln Leu Pro Ser Ser Val Gly Asp Leu Val His Leu
545                 550                 555                 560

Arg Tyr Leu Asp Leu Ser Gly Asn Lys Ile Cys Ser Leu Pro Lys Arg
                565                 570                 575

Leu Cys Lys Leu Arg Asn Leu Gln Thr Leu Asp Leu Tyr Asn Cys Gln
            580                 585                 590

Ser Leu Ser Cys Leu Pro Lys Gln Thr Ser Lys Leu Cys Ser Leu Arg
        595                 600                 605

Asn Leu Val Leu Asp His Ser Cys Pro Leu Thr Ser Met Pro Pro Arg
    610                 615                 620

Ile Gly Leu Leu Thr Cys Leu Lys Thr Leu Gly Tyr Phe Val Val Gly
625                 630                 635                 640

Glu Arg Lys Gly Tyr Gln Leu Gly Glu Leu Arg Asn Leu Asn Leu Arg
                645                 650                 655

Gly Ala Ile Ser Ile Thr His Leu Glu Arg Val Lys Asn Asp Met Glu
            660                 665                 670

Ala Lys Glu Ala Asn Leu Ser Ala Lys Ala Asn Leu His Ser Leu Ser
        675                 680                 685

Met Ser Trp Asp Arg Pro Asn Arg Tyr Glu Ser Glu Glu Val Lys Val
    690                 695                 700

Leu Glu Ala Leu Lys Pro His Pro Asn Leu Lys Tyr Leu Glu Ile Ile
705                 710                 715                 720

Asp Phe Cys Gly Phe Cys Leu Pro Asp Trp Met Asn His Ser Val Leu
                725                 730                 735

Lys Asn Val Val Ser Ile Leu Ile Ser Gly Cys Glu Asn Cys Ser Cys
            740                 745                 750

Leu Pro Pro Phe Gly Glu Leu Pro Cys Leu Glu Ser Leu Glu Leu Gln
        755                 760                 765
```

```
Asp Gly Ser Val Glu Val Glu Tyr Val Glu Asp Ser Gly Phe Leu Thr
            770                 775                 780

Arg Arg Arg Phe Pro Ser Leu Arg Lys Leu His Ile Gly Gly Phe Cys
785                 790                 795                 800

Asn Leu Lys Gly Leu Gln Arg Met Lys Gly Ala Glu Gln Phe Pro Val
                805                 810                 815

Leu Glu Glu Met Lys Ile Ser Asp Cys Pro Met Phe Val Phe Pro Thr
                820                 825                 830

Leu Ser Ser Val Lys Lys Leu Glu Ile Trp Gly Glu Ala Asp Ala Gly
                835                 840                 845

Gly Leu Ser Ser Ile Ser Asn Leu Ser Thr Leu Thr Ser Leu Lys Ile
        850                 855                 860

Phe Ser Asn His Thr Val Thr Ser Leu Leu Glu Glu Met Phe Lys Asn
865                 870                 875                 880

Leu Glu Asn Leu Ile Tyr Leu Ser Val Ser Phe Leu Glu Asn Leu Lys
                885                 890                 895

Glu Leu Pro Thr Ser Leu Ala Ser Leu Asn Asn Leu Lys Cys Leu Asp
                900                 905                 910

Ile Arg Tyr Cys Tyr Ala Leu Glu Ser Leu Pro Glu Gly Leu Glu
        915                 920                 925

Gly Leu Ser Ser Leu Thr Glu Leu Phe Val Glu His Cys Asn Met Leu
        930                 935                 940

Lys Cys Leu Pro Glu Gly Leu Gln His Leu Thr Thr Leu Thr Ser Leu
945                 950                 955                 960

Lys Ile Arg Gly Cys Pro Gln Leu Ile Lys Arg Cys
                965                 970

<210> SEQ ID NO 62
<211> LENGTH: 945
<212> TYPE: PRT
<213> ORGANISM: Artificial Sequence
<220> FEATURE:
<223> OTHER INFORMATION: Description of Artificial Sequence: alignment
      SH20-tub
<220> FEATURE:
<221> NAME/KEY: SITE
<222> LOCATION: (1)..(945)

<400> SEQUENCE: 62

Met Ala Glu Ala Phe Ile Gln Val Leu Leu Glu Asn Ile Thr Ser Phe
  1               5                  10                  15

Ile Gln Gly Glu Leu Gly Leu Leu Gly Phe Glu Asn Asp Phe Glu
                 20                  25                  30

Asn Ile Ser Ser Arg Phe Ser Thr Ile Gln Ala Val Leu Glu Asp Ala
         35                  40                  45

Gln Glu Lys Gln Leu Lys Asp Lys Ala Ile Lys Asn Trp Leu Gln Lys
    50                  55                  60

Leu Asn Ala Ala Val Tyr Lys Val Asp Asp Leu Leu Asp Glu Cys Lys
 65                  70                  75                  80

Ala Ala Arg Leu Glu Gln Ser Arg Leu Gly Cys His His Pro Lys Ala
                 85                  90                  95

Ile Val Phe Arg His Lys Ile Gly Lys Arg Ile Lys Glu Met Met Glu
                100                 105                 110

Lys Leu Asp Ala Ile Ala Lys Glu Arg Thr Asp Phe His Leu His Glu
            115                 120                 125

Lys Ile Ile Glu Arg Gln Val Ala Arg Pro Glu Thr Gly Phe Val Leu
        130                 135                 140
```

-continued

```
Thr Glu Pro Gln Val Tyr Gly Arg Asp Lys Glu Glu Asp Glu Ile Val
145                 150                 155                 160

Lys Ile Leu Ile Asn Asn Val Ser Asn Ala Gln Glu Leu Ser Val Leu
                165                 170                 175

Pro Ile Leu Gly Met Gly Leu Gly Lys Thr Thr Leu Ala Gln Met
            180                 185                 190

Val Phe Asn Asp Gln Arg Val Thr Glu His Phe Tyr Pro Lys Ile Trp
            195                 200                 205

Ile Cys Val Ser Asp Asp Phe Asp Glu Lys Arg Leu Ile Glu Asn Ile
            210                 215                 220

Ile Gly Asn Ile Glu Arg Ser Ser Leu Asp Val Lys Asp Leu Ala Ser
225                 230                 235                 240

Phe Gln Lys Lys Leu Gln Gln Leu Leu Asn Gly Lys Arg Tyr Leu Leu
                245                 250                 255

Val Leu Asp Asp Val Trp Asn Glu Asp Gln Gln Lys Trp Asp Asn Leu
            260                 265                 270

Arg Val Val Leu Lys Val Gly Ala Ser Gly Ala Ser Val Leu Thr Thr
            275                 280                 285

Thr Arg Leu Glu Lys Val Gly Ser Ile Met Gly Thr Leu Gln Pro Tyr
290                 295                 300

Gln Leu Ser Asn Leu Ser Gln Asp Asp Cys Trp Leu Leu Phe Ile Gln
305                 310                 315                 320

Arg Ala Phe Arg His Gln Glu Glu Ile Ser Pro Asn Leu Val Ala Ile
                325                 330                 335

Gly Lys Glu Ile Val Lys Lys Ser Gly Gly Val Pro Leu Ala Ala Lys
            340                 345                 350

Thr Leu Gly Gly Leu Leu Arg Phe Lys Arg Glu Lys Arg Glu Trp Glu
            355                 360                 365

His Val Arg Asp Ser Glu Ile Trp Asn Leu Pro Gln Asp Glu Met Ser
370                 375                 380

Ile Leu Pro Ala Leu Arg Leu Ser Tyr His His Leu Pro Leu Ala Leu
385                 390                 395                 400

Arg Gln Cys Phe Ala Tyr Cys Ala Val Phe Pro Lys Asp Thr Lys Met
                405                 410                 415

Glu Lys Lys Lys Val Ile Ser Leu Trp Met Ala His Gly Phe Leu Leu
            420                 425                 430

Ser Arg Arg Asn Leu Glu Leu Glu Asp Val Arg Asn Glu Gly Trp Asn
            435                 440                 445

Glu Leu Tyr Leu Arg Ser Phe Phe Gln Glu Ile Glu Val Arg Tyr Gly
            450                 455                 460

Asn Thr Tyr Phe Lys Met His Asp Leu Ile His Asp Leu Ala Thr Ser
465                 470                 475                 480

Leu Phe Ser Ala Asn Thr Ser Ser Asn Ile Arg Glu Ile Asn Val
                485                 490                 495

Glu Ser Tyr Thr His Met Met Ser Ile Gly Phe Ser Glu Val Val Ser
            500                 505                 510

Ser Tyr Ser Pro Ser Leu Leu Gln Lys Phe Val Ser Leu Arg Val Leu
            515                 520                 525

Asn Leu Ser Tyr Ser Lys Phe Glu Glu Leu Pro Ser Ser Ile Gly Asp
            530                 535                 540

Leu Val His Leu Arg Tyr Met Asp Leu Ser Asn Asn Ile Glu Ile Arg
545                 550                 555                 560
```

```
Ser Leu Pro Lys Gln Leu Cys Lys Leu Gln Asn Leu Gln Thr Leu Asp
            565                 570                 575

Leu Gln Tyr Cys Thr Arg Leu Cys Cys Leu Pro Lys Gln Thr Ser Lys
            580                 585                 590

Leu Gly Ser Leu Arg Asn Leu Leu His Gly Cys His Arg Leu Thr
            595                 600                 605

Arg Thr Pro Pro Arg Ile Gly Ser Leu Thr Cys Leu Lys Thr Leu Gly
            610                 615                 620

Gln Ser Val Val Lys Arg Lys Gly Tyr Gln Leu Gly Glu Leu Gly
625                     630                 635                 640

Ser Leu Asn Leu Tyr Gly Ser Ile Lys Ile Ser His Leu Glu Arg Val
            645                 650                 655

Lys Asn Asp Lys Glu Ala Lys Glu Ala Asn Leu Ser Ala Lys Glu Asn
            660                 665                 670

Leu His Ser Leu Ser Met Lys Trp Asp Asp Glu Pro His Arg Tyr
            675                 680                 685

Glu Ser Glu Glu Val Glu Val Leu Glu Ala Leu Lys Pro His Ser Asn
            690                 695                 700

Leu Thr Cys Leu Lys Ile Ser Gly Phe Arg Gly Ile Arg Leu Pro Asp
705                 710                 715                 720

Trp Met Asn His Ser Val Leu Lys Asn Ile Val Leu Ile Glu Ile Ser
            725                 730                 735

Gly Cys Lys Asn Cys Ser Cys Leu Pro Pro Phe Gly Asp Leu Pro Cys
            740                 745                 750

Leu Glu Ser Leu Glu Leu Tyr Arg Gly Ser Ala Glu Tyr Val Glu Glu
            755                 760                 765

Val Asp Ile Asp Val Asp Ser Gly Phe Pro Thr Arg Ile Arg Leu Pro
            770                 775                 780

Ser Leu Arg Lys Leu Cys Ile Cys Lys Phe Asp Asn Leu Lys Gly Leu
785                 790                 795                 800

Leu Lys Lys Glu Gly Gly Glu Gln Phe Pro Val Leu Glu Glu Met Glu
            805                 810                 815

Ile Arg Tyr Cys Pro Ile Pro Thr Leu Ser Pro Asn Leu Lys Ala Leu
            820                 825                 830

Thr Ser Leu Asn Ile Ser Asp Asn Lys Glu Ala Thr Ser Phe Pro Glu
            835                 840                 845

Glu Met Phe Lys Ser Leu Ala Asn Leu Lys Tyr Leu Asn Ile Ser His
            850                 855                 860

Phe Lys Asn Leu Lys Glu Leu Pro Thr Ser Leu Ala Ser Leu Asn Ala
865                 870                 875                 880

Leu Lys Ser Leu Lys Ile Gln Trp Cys Cys Ala Leu Glu Asn Ile Pro
            885                 890                 895

Lys Glu Gly Val Lys Gly Leu Thr Ser Leu Thr Glu Leu Ile Val Lys
            900                 905                 910

Phe Ser Lys Val Leu Lys Cys Leu Pro Glu Gly Leu His His Leu Thr
            915                 920                 925

Ala Leu Thr Arg Leu Lys Ile Trp Gly Cys Pro Gln Leu Ile Lys Arg
            930                 935                 940

Cys
945

<210> SEQ ID NO 63
<211> LENGTH: 945
<212> TYPE: PRT
```

```
<213> ORGANISM: Artificial Sequence
<220> FEATURE:
<223> OTHER INFORMATION: Description of Artificial Sequence: alignment
      T118-tar
<220> FEATURE:
<221> NAME/KEY: SITE
<222> LOCATION: (1)..(945)

<400> SEQUENCE: 63
```

| | | | | | | | | | | | | | | | |
|---|---|---|---|---|---|---|---|---|---|---|---|---|---|---|---|
|Met|Ala|Glu|Ala|Phe|Ile|Gln|Val|Leu|Leu|Glu|Asn|Ile|Thr|Ser|Phe|
|1| | | |5| | | | |10| | | | |15| |
|Ile|Gln|Gly|Glu|Leu|Gly|Leu|Leu|Gly|Phe|Glu|Asn|Glu|Phe|Glu| |
| | | | |20| | | | |25| | | | |30| |
|Asn|Ile|Ser|Ser|Arg|Phe|Ser|Thr|Ile|Gln|Ala|Val|Leu|Glu|Asp|Ala|
| | | | |35| | | | |40| | | | |45| |
|Gln|Glu|Lys|Gln|Leu|Lys|Asp|Lys|Ala|Ile|Lys|Asn|Trp|Leu|Gln|Lys|
| |50| | | | |55| | | | |60| | | | |
|Leu|Asn|Ala|Ala|Tyr|Lys|Val|Asp|Asp|Leu|Leu|Asp|Glu|Cys|Lys| |
|65| | | |70| | | | |75| | | | |80| |
|Ala|Ala|Arg|Leu|Glu|Gln|Ser|Arg|Leu|Gly|Arg|His|His|Pro|Lys|Ala|
| | | | |85| | | | |90| | | | |95| |
|Ile|Val|Phe|Arg|His|Lys|Ile|Gly|Lys|Arg|Ile|Lys|Glu|Met|Met|Glu|
| | | | |100| | | | |105| | | | |110| |
|Lys|Leu|Asp|Ala|Ile|Ala|Lys|Glu|Arg|Thr|Asp|Phe|His|Leu|His|Glu|
| | | | |115| | | | |120| | | | |125| |
|Lys|Ile|Ile|Glu|Arg|Gln|Val|Ala|Arg|Pro|Glu|Thr|Gly|Pro|Val|Leu|
| | | |130| | | | |135| | | | |140| | |
|Thr|Glu|Pro|Gln|Val|Tyr|Gly|Arg|Asp|Lys|Glu|Glu|Asp|Glu|Ile|Val|
|145| | | | |150| | | | |155| | | | |160|
|Lys|Ile|Leu|Ile|Asn|Asn|Val|Ser|Asn|Ala|Leu|Glu|Leu|Ser|Val|Leu|
| | | | |165| | | | |170| | | | |175| |
|Pro|Ile|Leu|Gly|Met|Gly|Gly|Leu|Gly|Lys|Thr|Thr|Leu|Ala|Gln|Met|
| | | | |180| | | | |185| | | | |190| |
|Val|Phe|Asn|Asp|Gln|Arg|Val|Thr|Glu|His|Phe|Tyr|Pro|Lys|Ile|Trp|
| | | | |195| | | | |200| | | | |205| |
|Ile|Cys|Val|Ser|Asp|Asp|Phe|Asp|Glu|Lys|Arg|Leu|Ile|Glu|Thr|Ile|
| | | |210| | | | |215| | | | |220| | |
|Ile|Gly|Asn|Ile|Glu|Arg|Ser|Ser|Leu|Asp|Val|Lys|Asp|Leu|Ala|Ser|
|225| | | | |230| | | | |235| | | | |240|
|Phe|Gln|Lys|Lys|Leu|Gln|Gln|Leu|Leu|Asn|Gly|Lys|Arg|Tyr|Leu|Leu|
| | | | |245| | | | |250| | | | |255| |
|Val|Leu|Asp|Asp|Val|Trp|Asn|Glu|Asp|Gln|Gln|Lys|Trp|Asp|Asn|Leu|
| | | | |260| | | | |265| | | | |270| |
|Arg|Ala|Val|Leu|Lys|Val|Gly|Ala|Ser|Gly|Ala|Ser|Val|Leu|Thr|Thr|
| | | |275| | | | |280| | | | |285| | |
|Thr|Arg|Leu|Glu|Lys|Val|Gly|Ser|Ile|Met|Gly|Thr|Leu|Gln|Pro|Tyr|
| | | |290| | | | |295| | | | |300| | |
|Gln|Leu|Ser|Asn|Leu|Ser|Gln|Asp|Asp|Cys|Trp|Leu|Leu|Phe|Ile|Gln|
|305| | | | |310| | | | |315| | | | |320|
|Arg|Ala|Tyr|Arg|His|Gln|Glu|Glu|Ile|Ser|Pro|Asn|Leu|Val|Ala|Ile|
| | | | |325| | | | |330| | | | |335| |
|Gly|Lys|Glu|Ile|Val|Lys|Ser|Gly|Gly|Val|Pro|Leu|Ala|Ala|Lys| |
| | | | |340| | | | |345| | | | |350| |
|Thr|Leu|Gly|Gly|Leu|Leu|Arg|Phe|Lys|Arg|Glu|Lys|Arg|Glu|Trp|Glu|
| | | |355| | | | |360| | | | |365| | |

-continued

```
His Val Arg Asp Ser Glu Ile Trp Asn Leu Pro Gln Asp Glu Met Ser
    370                 375                 380

Ile Leu Pro Val Leu Arg Leu Ser Tyr His His Leu Pro Leu Asp Leu
385                 390                 395                 400

Arg Gln Cys Phe Ala Tyr Cys Ala Val Phe Pro Lys Asp Thr Lys Met
                405                 410                 415

Glu Lys Lys Lys Val Ile Ser Leu Trp Met Ala His Gly Phe Leu Leu
            420                 425                 430

Ser Arg Arg Asn Leu Glu Leu Glu Asp Val Gly Asn Glu Val Trp Asn
        435                 440                 445

Glu Leu Tyr Leu Arg Ser Phe Phe Gln Glu Ile Glu Val Arg Tyr Gly
    450                 455                 460

Asn Thr Tyr Phe Lys Met His Asp Leu Ile His Asp Leu Ala Thr Ser
465                 470                 475                 480

Leu Phe Ser Ala Asn Thr Ser Ser Asn Ile Arg Glu Ile Asn Val
                485                 490                 495

Glu Ser Tyr Thr His Met Met Ser Ile Gly Phe Ser Glu Val Val Ser
                500                 505                 510

Ser Tyr Ser Pro Ser Leu Leu Gln Lys Phe Val Ser Leu Arg Val Leu
        515                 520                 525

Asn Leu Ser Tyr Ser Lys Phe Glu Glu Leu Pro Ser Ser Ile Gly Asp
    530                 535                 540

Leu Val His Leu Arg Tyr Met Asp Leu Ser Asn Asn Ile Glu Ile Arg
545                 550                 555                 560

Ser Leu Pro Lys Gln Leu Cys Lys Leu Gln Asn Leu Gln Thr Leu Asp
                565                 570                 575

Leu Gln Tyr Cys Thr Arg Leu Cys Cys Leu Pro Lys Gln Thr Ser Lys
            580                 585                 590

Leu Gly Ser Leu Arg Asn Leu Leu His Gly Cys His Arg Leu Thr
        595                 600                 605

Arg Thr Pro Pro Arg Ile Gly Ser Leu Thr Cys Leu Lys Thr Leu Gly
    610                 615                 620

Gln Phe Val Val Gly Arg Lys Lys Gly Tyr Gln Leu Gly Glu Leu Gly
625                 630                 635                 640

Ser Leu Asn Leu Tyr Gly Ser Ile Lys Ile Ser His Leu Glu Arg Val
                645                 650                 655

Lys Asn Asp Lys Glu Ala Lys Glu Ala Asn Leu Ser Ala Lys Glu Asn
            660                 665                 670

Leu His Ser Leu Ser Met Lys Trp Asp Asp Glu Pro His Arg Tyr
        675                 680                 685

Glu Ser Glu Glu Val Glu Val Leu Glu Ala Leu Lys Pro His Ser Asn
    690                 695                 700

Leu Thr Cys Leu Thr Ile Ser Gly Phe Arg Gly Ile Arg Leu Pro Asp
705                 710                 715                 720

Trp Met Asn His Ser Val Leu Lys Asn Ile Val Leu Ile Glu Ile Ser
                725                 730                 735

Gly Cys Lys Asn Cys Ser Cys Leu Pro Pro Phe Gly Asp Leu Pro Cys
            740                 745                 750

Leu Glu Ser Leu Gln Leu Tyr Arg Gly Ser Ala Glu Tyr Val Glu Glu
        755                 760                 765

Val Asp Ile Asp Val Asp Ser Gly Phe Pro Thr Arg Ile Arg Phe Pro
    770                 775                 780

Ser Leu Arg Lys Leu Cys Ile Cys Lys Phe Asp Asn Leu Lys Gly Leu
```

```
-continued
785                 790                 795                 800
Val Lys Lys Glu Gly Gly Glu Gln Phe Pro Val Leu Glu Glu Met Glu
                805                 810                 815

Ile Arg Tyr Cys Pro Ile Pro Thr Leu Ser Ser Asn Leu Lys Ala Leu
                820                 825                 830

Thr Ser Leu Asn Ile Ser Asp Asn Lys Glu Ala Thr Ser Phe Pro Glu
            835                 840                 845

Glu Met Phe Lys Ser Leu Ala Asn Leu Lys Tyr Leu Asn Ile Ser His
        850                 855                 860

Phe Lys Asn Leu Lys Glu Leu Pro Thr Ser Leu Ala Ser Leu Asn Ala
865                 870                 875                 880

Leu Lys Ser Leu Lys Ile Gln Trp Cys Cys Ala Leu Glu Ser Ile Pro
                885                 890                 895

Glu Glu Gly Val Lys Gly Leu Thr Ser Leu Thr Glu Leu Ile Val Lys
                900                 905                 910

Phe Cys Lys Met Leu Lys Cys Leu Pro Glu Gly Leu Gln His Leu Thr
            915                 920                 925

Ala Leu Thr Arg Val Lys Ile Trp Gly Cys Pro Gln Leu Ile Lys Arg
        930                 935                 940

Cys
945
```